(12) United States Patent
Manash et al.

(10) Patent No.: US 11,083,571 B2
(45) Date of Patent: Aug. 10, 2021

(54) FRAME FOR PROSTHETIC HEART VALVE

(71) Applicant: Edwards Lifesciences Corporation, Irvine, CA (US)

(72) Inventors: Boaz Manash, Givat Ada (IL); Khen Perlmutter, Binyamina (IL); Adi Carmi, Ganei Tikva (IL); Noa Axelrod, Netanya (IL); Nikolay Gurovich, Hadera (IL)

(73) Assignee: Edwards Lifesciences Corporation, Irvine, CA (US)

( * ) Notice: Subject to any disclaimer, the term of this patent is extended or adjusted under 35 U.S.C. 154(b) by 87 days.

(21) Appl. No.: 16/442,165

(22) Filed: Jun. 14, 2019

(65) Prior Publication Data

US 2020/0000579 A1    Jan. 2, 2020

Related U.S. Application Data

(60) Provisional application No. 62/690,481, filed on Jun. 27, 2018.

(51) Int. Cl.
*A61F 2/24*    (2006.01)

(52) U.S. Cl.
CPC .......... *A61F 2/2409* (2013.01); *A61F 2/2418* (2013.01); *A61F 2/2427* (2013.01); *A61F 2230/0093* (2013.01)

(58) Field of Classification Search
CPC .................. A61F 2/24; A61F 2/2415
USPC .................. 623/2.1–2.19
See application file for complete search history.

(56) References Cited

U.S. PATENT DOCUMENTS

| | | | |
|---|---|---|---|
| 5,411,522 | A | 5/1995 | Trott |
| 5,591,197 | A | 1/1997 | Orth et al. |
| 5,843,167 | A | 12/1998 | Dwyer et al. |
| 6,425,916 | B1 | 7/2002 | Garrison et al. |
| 6,730,118 | B2 | 5/2004 | Spenser et al. |
| 7,815,673 | B2 | 10/2010 | Bloom et al. |
| 8,652,202 | B2 | 2/2014 | Alon et al. |
| 9,155,619 | B2 | 10/2015 | Liu et al. |

(Continued)

FOREIGN PATENT DOCUMENTS

| | | |
|---|---|---|
| EP | 0732088 A2 | 9/1996 |
| EP | 2802290 B1 | 11/2014 |

(Continued)

*Primary Examiner* — Suzette J Gherbi
(74) *Attorney, Agent, or Firm* — Klarquist Sparkman LLP

(57) ABSTRACT

A prosthetic heart valve is radially collapsible to a collapsed configuration and radially expandable to an expanded configuration. The heart valve includes an annular inner frame formed with a plurality of angled first strut members, the inner frame being configured to foreshorten from a first length corresponding to the collapsed configuration to a second length corresponding to the expanded configuration. A leaflet structure is situated at least partially within the inner frame. An outer frame is disposed radially outward of the inner frame and coupled to the inner frame. The outer frame is configured to collapse with the inner frame and radially expand with the inner frame, and includes a plurality of second strut members. Portions of the second strut members are configured to bend radially outwardly into a curved shape as the inner frame and the outer frame move from the collapsed configuration to the expanded configuration.

20 Claims, 32 Drawing Sheets

(56) References Cited

U.S. PATENT DOCUMENTS

| | | | |
|---|---|---|---|
| 9,724,121 B2 | 8/2017 | Hefer | |
| 9,867,700 B2 | 1/2018 | Bakis et al. | |
| 10,828,153 B2* | 11/2020 | Noe | A61F 2/2445 |
| 2008/0262593 A1 | 10/2008 | Ryan et al. | |
| 2012/0123529 A1 | 5/2012 | Levi et al. | |
| 2015/0142104 A1 | 5/2015 | Braido | |
| 2017/0079790 A1 | 3/2017 | Vidlund et al. | |
| 2018/0028310 A1 | 2/2018 | Gurovich et al. | |
| 2018/0153687 A1 | 6/2018 | Hariton et al. | |
| 2018/0153689 A1 | 6/2018 | Maimon et al. | |
| 2018/0206983 A1* | 7/2018 | Noe | A61F 2/2445 |
| 2018/0296341 A1* | 10/2018 | Noe | A61F 2/2418 |
| 2019/0038404 A1* | 2/2019 | Iamberger | A61F 2/2412 |
| 2020/0237507 A1* | 7/2020 | Noe | A61F 2/2418 |
| 2020/0261223 A1* | 8/2020 | Quadri | A61F 2/2409 |

FOREIGN PATENT DOCUMENTS

| | | |
|---|---|---|
| EP | 3107496 B1 | 7/2018 |
| KR | 101804079 B1 | 12/2017 |
| WO | 2013059747 A1 | 4/2013 |
| WO | 2018040244 A1 | 3/2018 |

\* cited by examiner

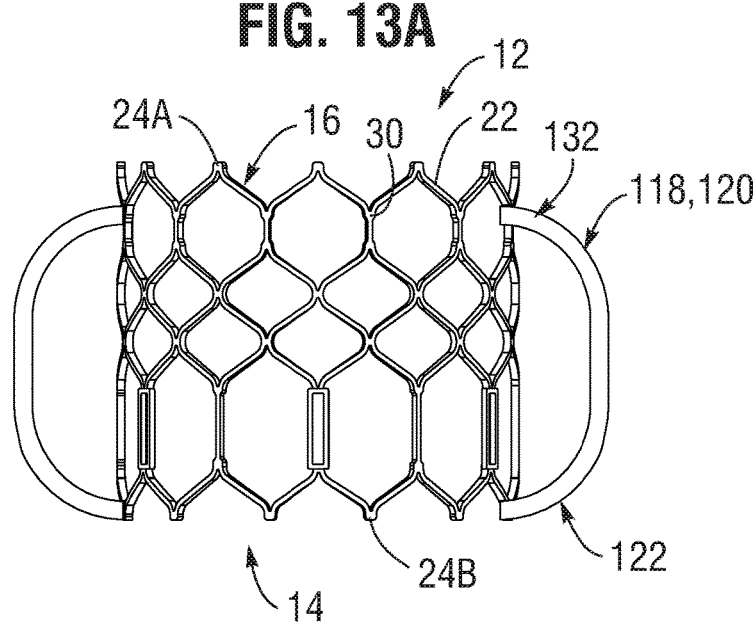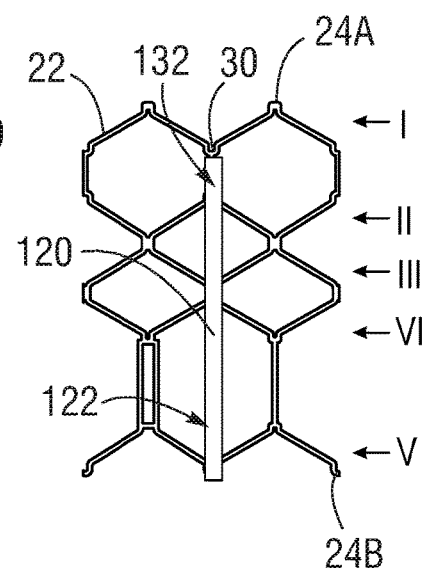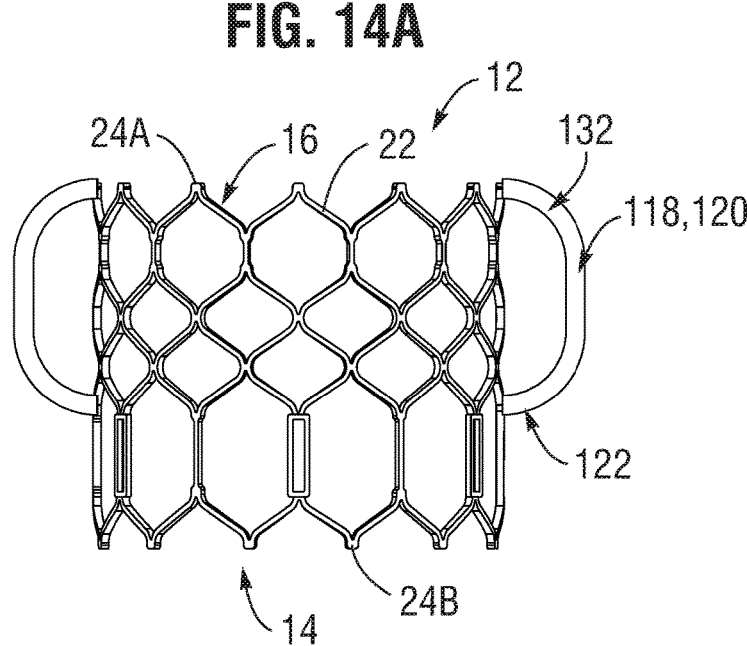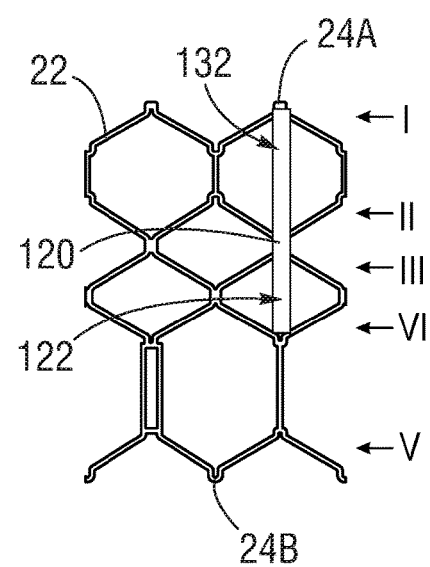

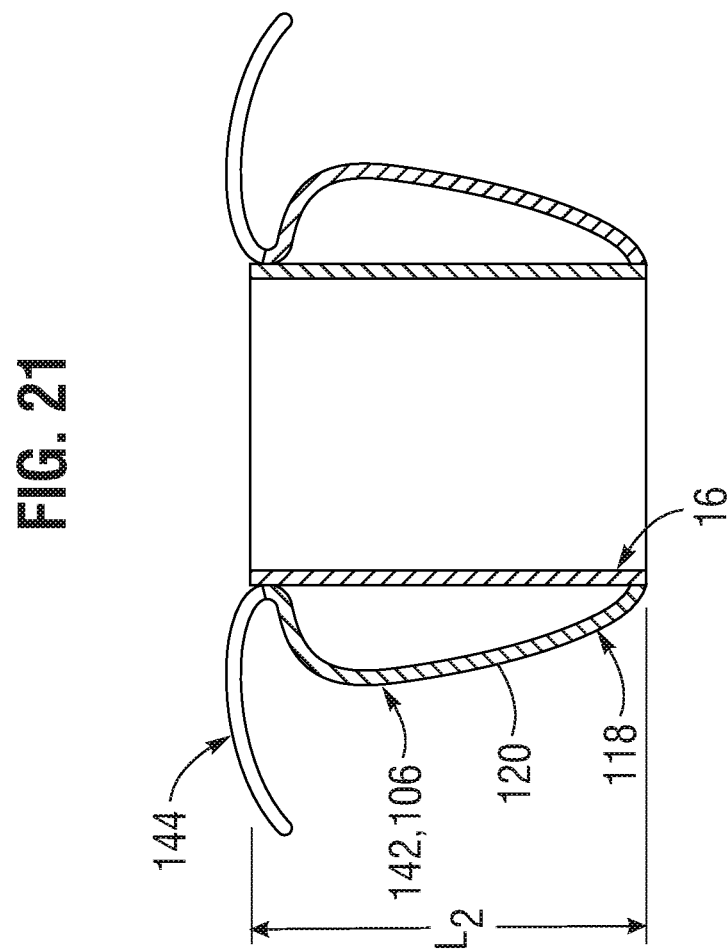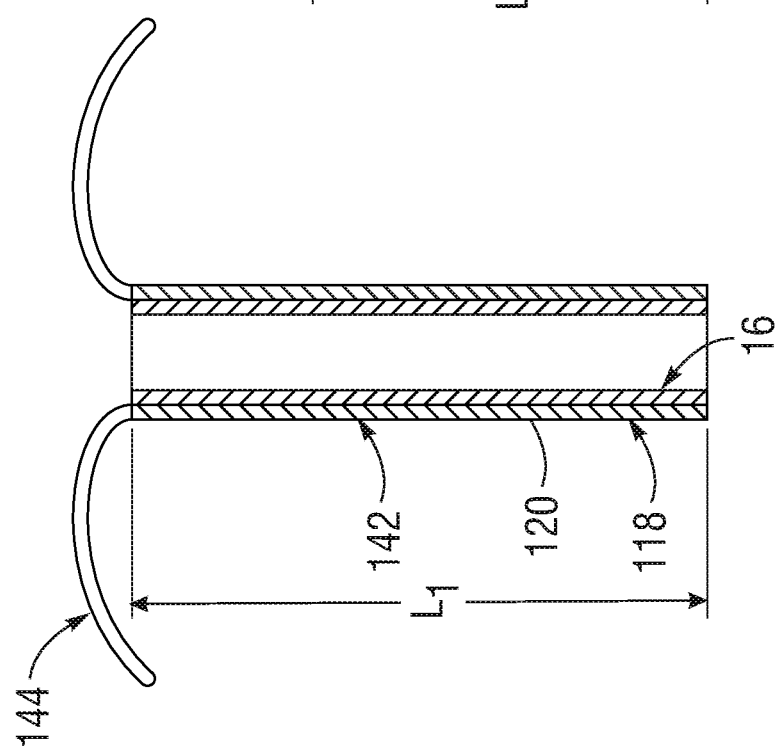

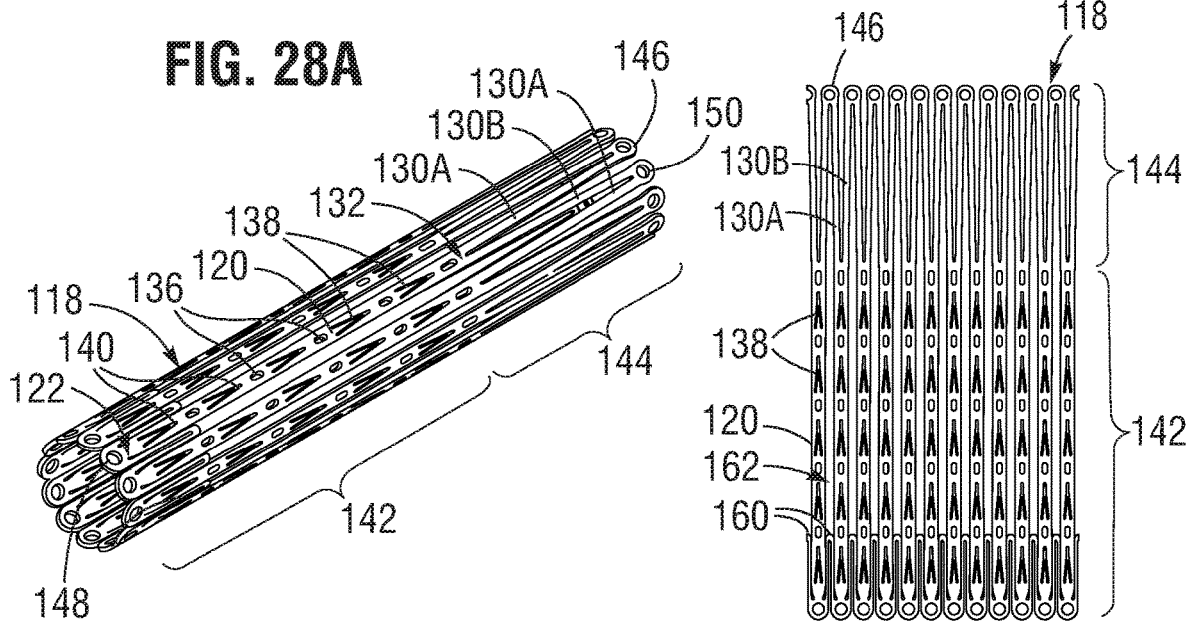
FIG. 28A
FIG. 28B
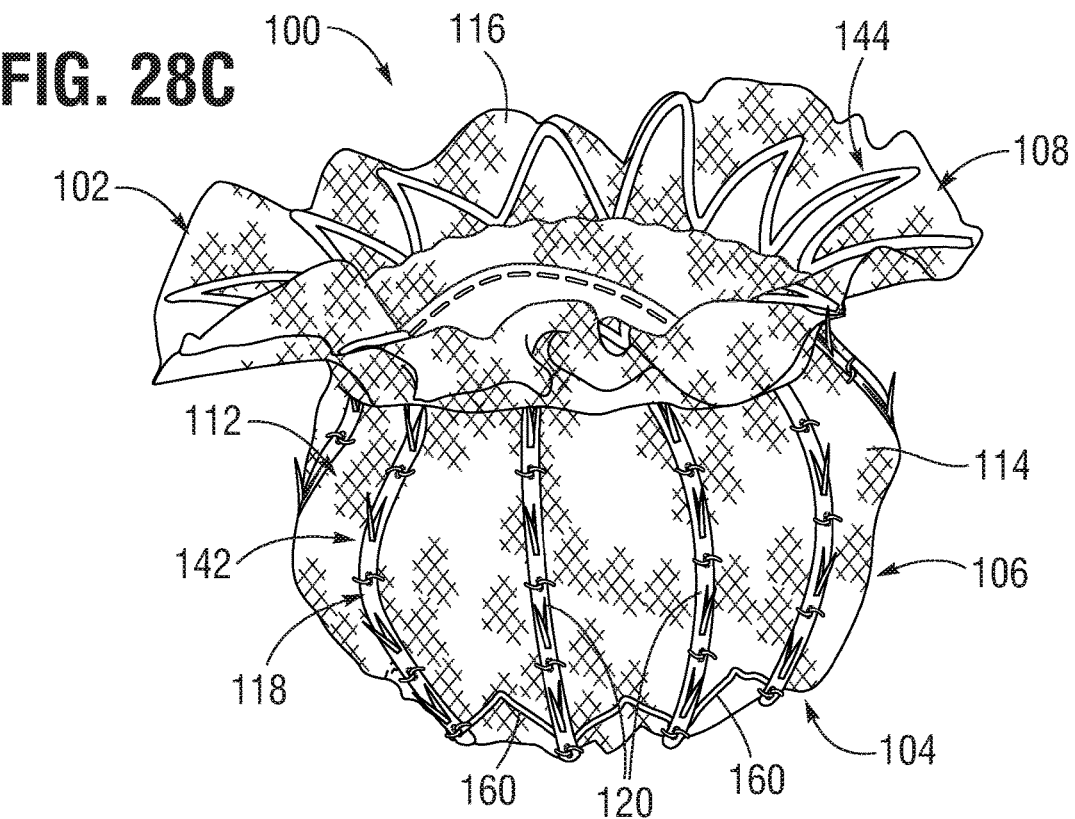
FIG. 28C

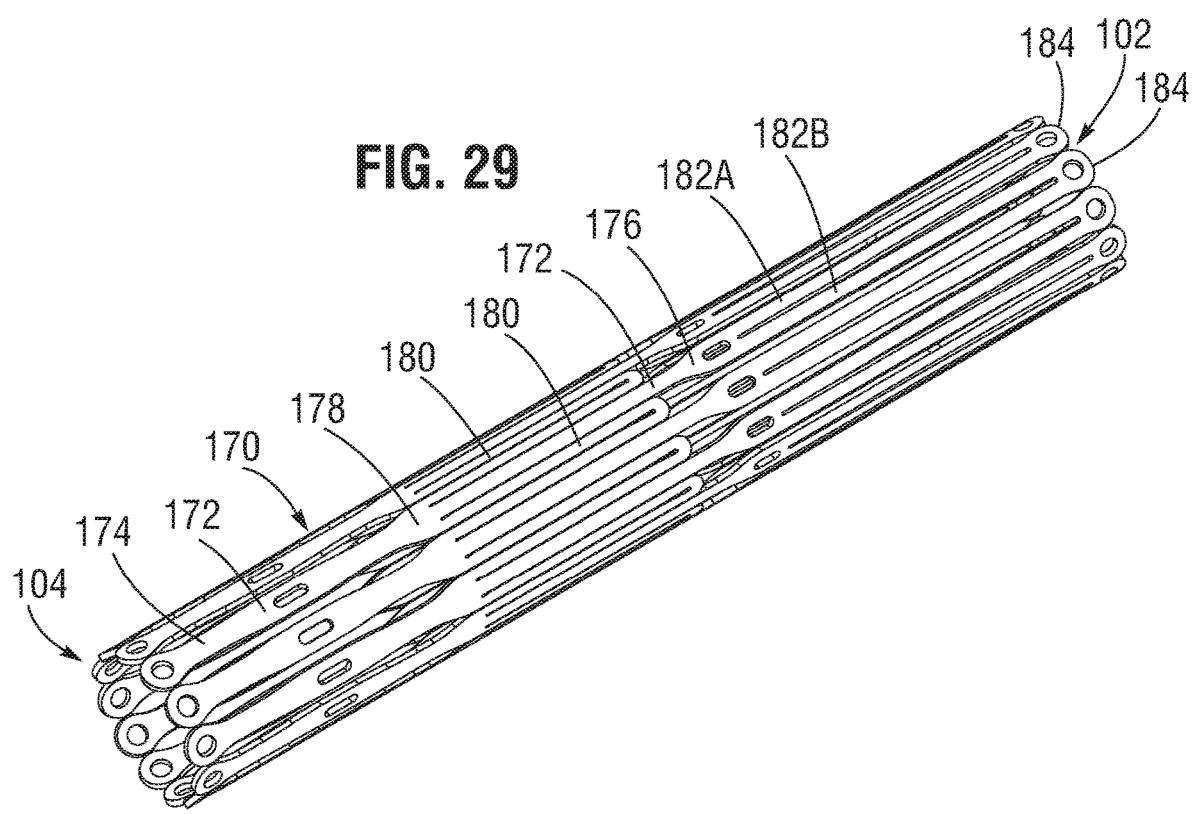

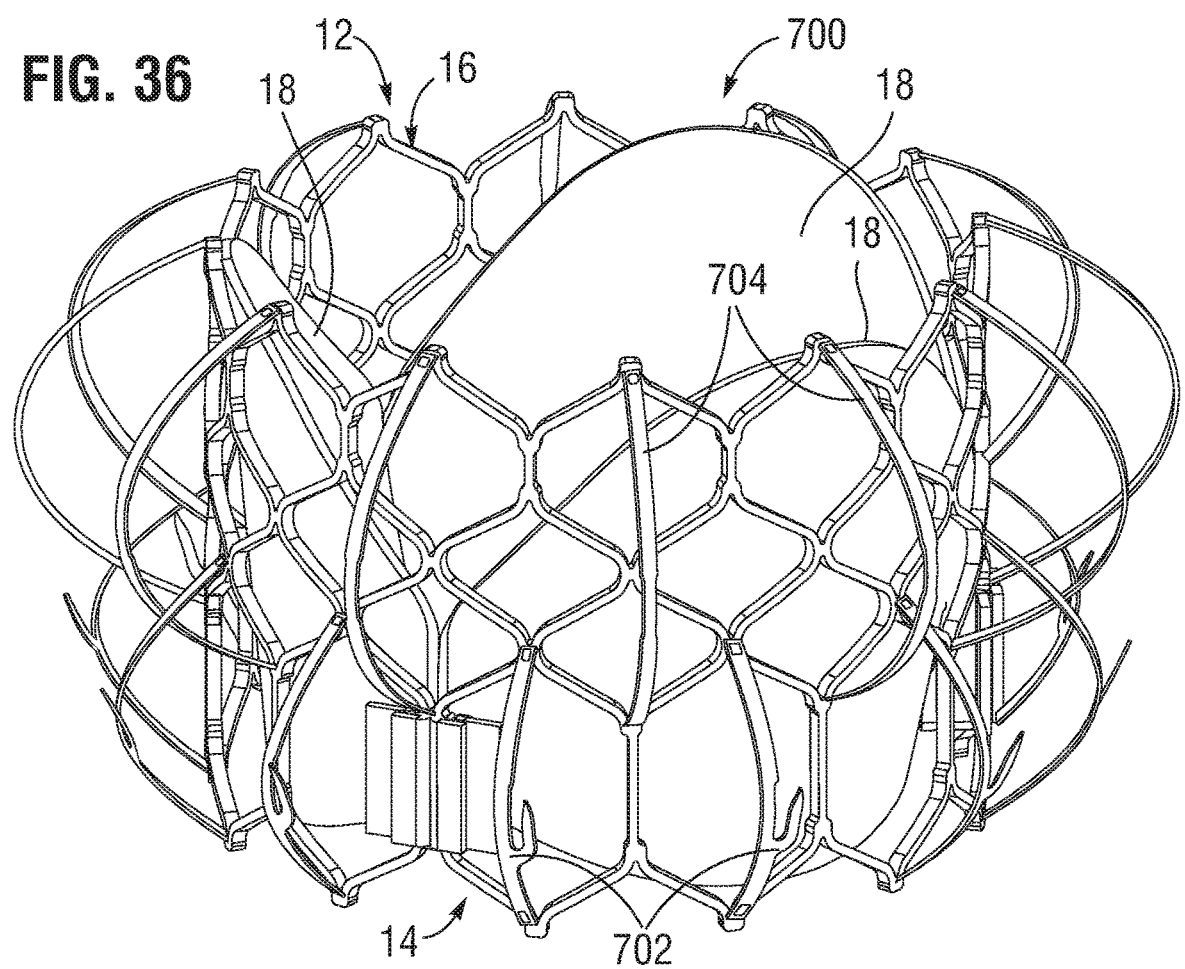
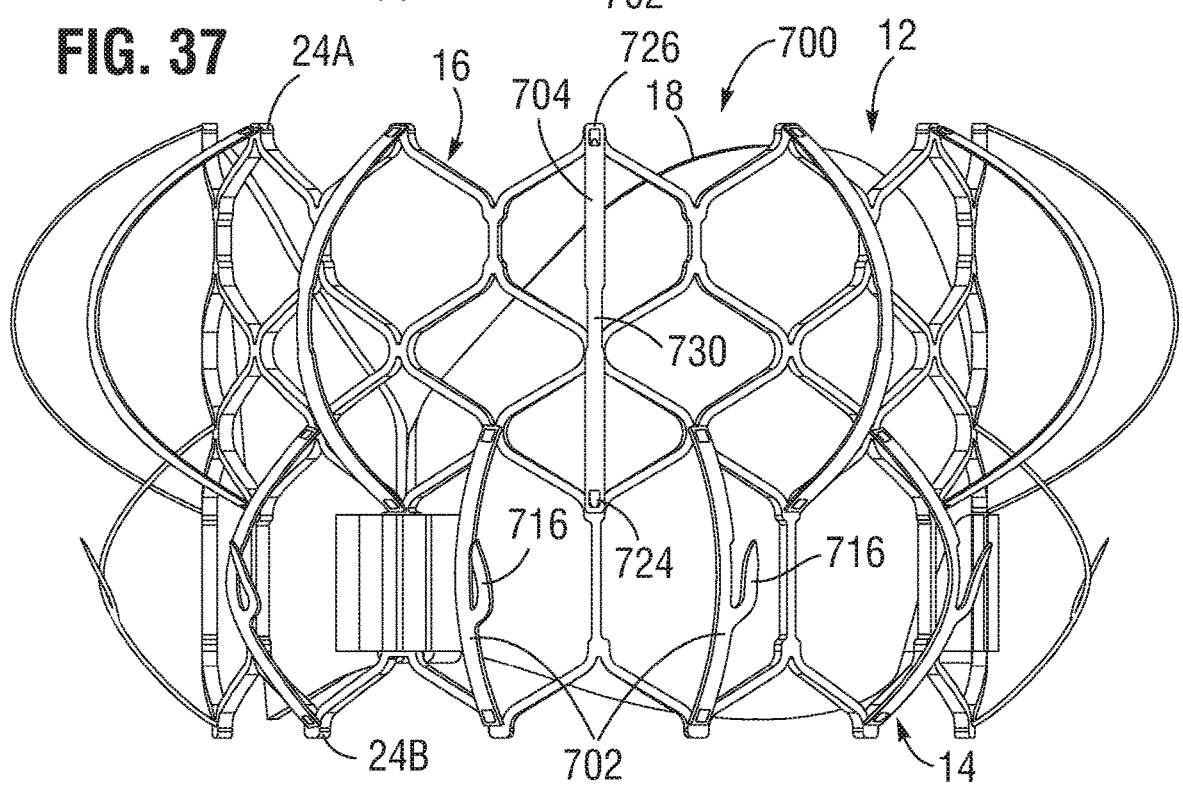

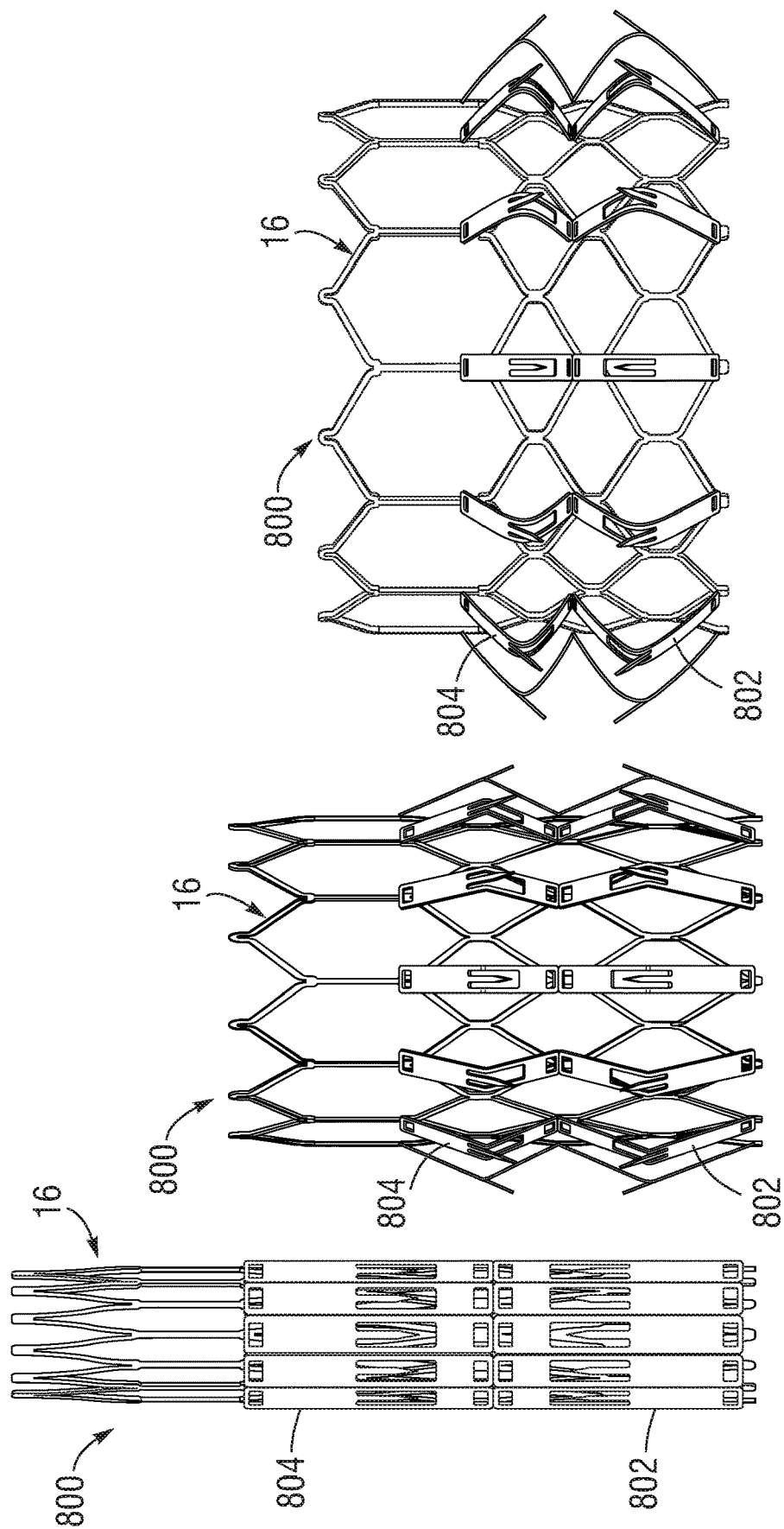

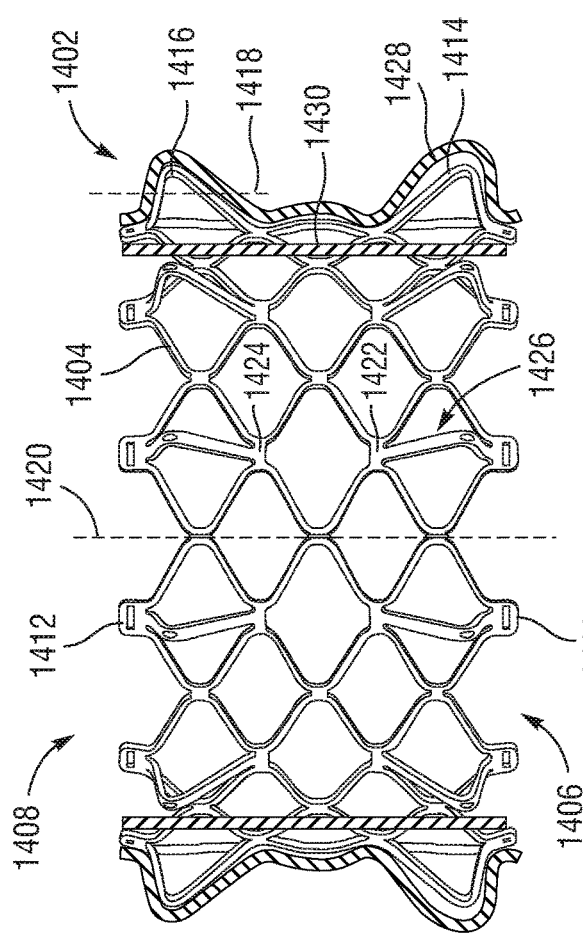
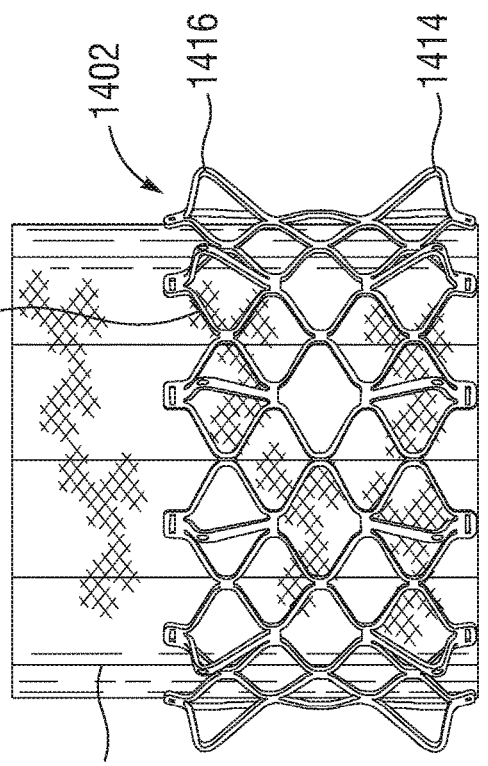
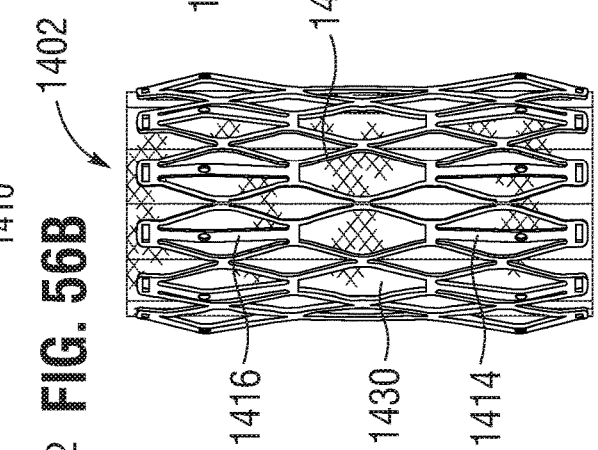
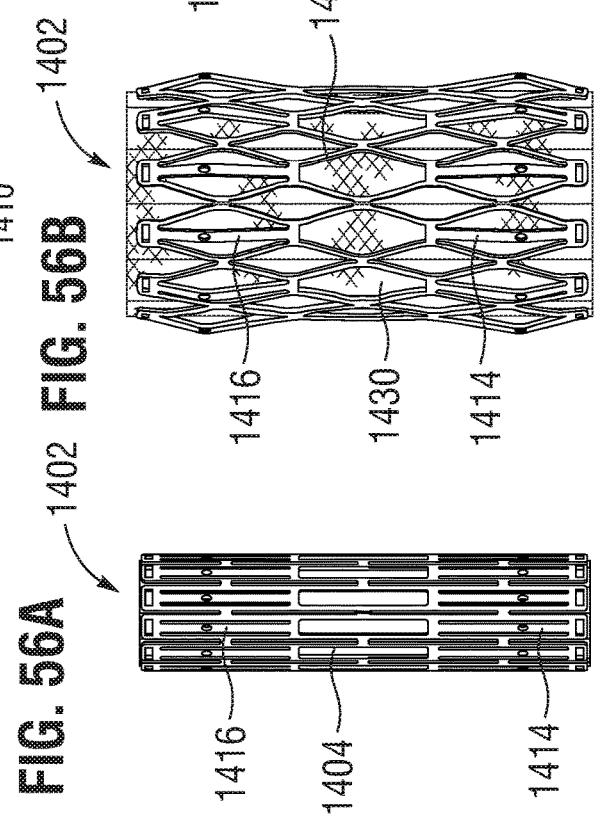
FIG. 55
FIG. 56A
FIG. 56B
FIG. 56C

FRAME FOR PROSTHETIC HEART VALVE

CROSS REFERENCE TO RELATED APPLICATION

The present application claims the benefit of U.S. Provisional Application No. 62/690,481, filed Jun. 27, 2018. The entire disclosure of U.S. Provisional Application No. 62/690,481 is incorporated herein by reference.

FIELD

The present application relates to prosthetic implants, such as prosthetic heart valves, including a frame having struts that curve outwardly from the frame when the frame expands to engage tissue surrounding the prosthetic heart valve.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are becoming commonplace for patients too frail to withstand the procedure to implant a surgical device. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

In cases of mitral valve stenosis, the non-circular shape of the mitral valve orifice, as well as the chordae tendineae connected to the ventricular sides of the mitral valve leaflets, can complicate placement and retention of a prosthetic valve in the native mitral valve. Many existing prosthetic valves are generally cylindrically-shaped and, thus, perivalvular leakage past the prosthetic valve during ventricular systole can be a concern when such valves are implanted in the native mitral valve. Left ventricular outflow tract (LVOT) obstruction can also be associated with existing prosthetic valves when implanted in the native mitral valve. Moreover, many existing prosthetic valves rely on a retention feature that is separate from the prosthetic valve, such as an anchoring device, in order to hold the prosthetic valve in place in the mitral annulus. These systems require a two-step implantation process, in which the anchoring device is first implanted in the mitral annulus, followed by implanting the prosthetic valve within the anchoring device. Accordingly, there is a need for improvements to prosthetic heart valves for implantation in the native mitral valve.

SUMMARY

The present disclosure pertains to prosthetic implants, such as prosthetic heart valves, including a frame having struts that curve outwardly from the frame when the frame expands to engage tissue surrounding the prosthetic heart valve. In a representative embodiment, a prosthetic heart valve that is radially collapsible to a collapsed configuration and radially expandable to an expanded configuration comprises an annular inner frame comprising a plurality of angled first strut members. The inner frame is configured to foreshorten from a first length corresponding to the collapsed configuration to a second length corresponding to the expanded configuration when the prosthetic heart valve is expanded to the expanded configuration. A leaflet structure is situated at least partially within the inner frame. An outer frame is disposed radially outward of the inner frame and coupled to the inner frame, the outer frame being configured to collapse with the inner frame to the collapsed configuration and expand with the inner frame to the expanded configuration. The outer frame comprises a plurality of second strut members. At least respective portions of the second strut members are configured to bend radially outwardly into a curved shape as the inner frame and the outer frame move from the collapsed configuration to the expanded configuration.

In any or all of the disclosed embodiments, the second strut members comprise first and second end portions, and the first and second end portions of the second strut members are coupled to the outer frame such that the first and second end portions move toward each other as the outer frame expands to bend the second strut members into the curved shape.

In any or all of the disclosed embodiments, the inner frame comprises an inflow end and an outflow end, and the second strut members extend from the inflow end of the inner frame to the outflow end.

In any or all of disclosed embodiments, the outer frame further comprises circumferentially-extending strut members that interconnect the second strut members.

In any or all of the disclosed embodiments, the inner frame comprises an inflow end and an outflow end, the second strut members are situated around the inner frame, and each of the second strut members branches into two third strut members adjacent the inflow end of the inner frame.

In any or all of the disclosed embodiments, the third strut members extending from a given second strut member curve radially away from the inner frame and are coupled to third strut members of adjacent second strut members.

In any or all of the disclosed embodiments, when the prosthetic heart valve is in the expanded configuration, the second strut members form a first portion of the outer frame having a convex exterior surface, and the third strut members form a second portion of the outer frame comprising an annular flange.

In any or all of the disclosed embodiments, the second strut members comprise apices spaced radially away from the inner frame when the prosthetic heart valve is in the expanded configuration.

In any or all of the disclosed embodiment, the prosthetic heart valve further comprises a skirt member disposed between the second strut members and the inner frame and secured to the second strut members.

In any or all of the disclosed embodiments, the prosthetic heart valve further comprises a skirt member secured to the third strut members.

In any or all of the disclosed embodiments, the second strut members comprise tissue-engaging members configured to extend radially outwardly from the second strut members when the second strut members are in the curved shape.

In another representative embodiment, a method comprises introducing a prosthetic heart valve of any of the disclosed embodiments into a patient's vasculature in the radially collapsed state, advancing the prosthetic heart valve to a treatment site, and radially expanding the prosthetic heart valve such that the inner frame foreshortens and the second strut members of the outer frame bend into the curved shape.

In another representative embodiment, a prosthetic heart valve that is radially collapsible to a collapsed configuration and radially expandable to an expanded configuration comprises an annular frame comprising a plurality of angled first strut members, the frame being configured to foreshorten from a first length corresponding to the collapsed configuration to a second length corresponding to the expanded configuration when the prosthetic heart valve is expanded to the expanded configuration. A leaflet structure is situated at least partially within the frame, and a plurality of second strut members extend longitudinally along at least a portion of the frame and are coupled to the frame. The second strut members are configured to bend radially outwardly as the frame moves from the collapsed configuration to the expanded configuration such that at least one of the second strut members forms a plurality of apices spaced radially outwardly from the frame when the prosthetic heart valve is in the expanded configuration.

In any or all of the disclosed embodiments, at least a portion of the plurality of second strut members comprise tissue-engaging members configured to extend away from the second strut members when the prosthetic heart valve is in the expanded configuration.

In any or all of the disclosed embodiments, the tissue-engaging members extend from apices of the second strut members.

In any or all of the disclosed embodiments, the second strut members comprise a first apex and a second apex when the prosthetic heart valve is in the expanded configuration, and the second apex is spaced radially outwardly from the frame by a greater distance than the first apex.

In another representative embodiment, a prosthetic heart valve that is radially collapsible to a collapsed configuration and radially expandable to an expanded configuration comprises an annular frame comprising a plurality of angled first strut members, the frame being configured to foreshorten from a first length corresponding to the collapsed configuration to a second length corresponding to the expanded configuration when the prosthetic heart valve is expanded to the expanded configuration. A leaflet structure is situated at least partially within the frame, and a plurality of second strut members extend longitudinally along at least a portion of the frame and are coupled to the frame. The second strut members are arranged circumferentially around the frame in a first row and configured to bend radially outwardly form the frame into a curved shape as the frame moves from the collapsed configuration to the expanded configuration. A plurality of third strut members extend longitudinally along at least a portion of the frame and are coupled to the frame. The third strut members are arranged circumferentially around the frame in a second row and are configured to bend radially outwardly form the frame into a curved shape as the frame moves from the collapsed configuration to the expanded configuration. The second strut members of the first row are circumferentially offset from the third strut members of the second row.

In any or all of the disclosed embodiments, the second strut members at least partially overlap with the third strut members in an axial direction when the prosthetic heart valve is in the expanded configuration.

In any or all of the disclosed embodiments, the third strut members comprise reduced width portions configured to induce bending of the third strut members at the reduced width portions.

In any or all of the disclosed embodiments, at least a portion of the plurality of second strut members comprise tissue-engaging members configured to extend away from the second strut members when the prosthetic heart valve is in the expanded configuration.

In another representative embodiment, a prosthetic heart valve that is radially collapsible to a collapsed configuration and radially expandable to an expanded configuration comprises an annular frame comprising a plurality of angled first strut members, the frame being configured to foreshorten from a first length corresponding to the collapsed configuration to a second length corresponding to the expanded configuration when the prosthetic heart valve is expanded to the expanded configuration. A leaflet structure is situated at least partially within the frame, and a plurality of second strut members are coupled to the frame and extend longitudinally along at least a portion of the frame. The second strut members are configured to bend radially outwardly into a curved shape as the frame moves from the collapsed configuration to the expanded configuration. A sealing member extends circumferentially around the frame and is coupled to the second strut members. The sealing member comprises first and second circumferential edges, the second circumferential edge being radially outward of the first circumferential edge when the prosthetic heart valve is in the expanded configuration.

In any or all of the disclosed embodiments, the prosthetic heart valve further comprises a plurality of longitudinally-oriented third strut members coupled to the frame, the third strut members being longitudinally offset from the second strut members along the frame and configured to bend into a curved shape as the frame moves from the collapsed configuration to the expanded configuration.

In any or all of the disclosed embodiments, the sealing member coupled to the second strut members is a first sealing member, and the prosthetic heart valve further comprises a second sealing member extending circumferentially around the frame and coupled to the third strut members.

In any or all of the disclosed embodiments, the first sealing member is angled toward an outflow end of the frame, and the second sealing member is angled toward an inflow end of the frame.

In any or all of the disclosed embodiments, the second strut members comprise tissue-engaging members oriented toward the outflow end of the frame, and the third strut members comprise tissue-engaging members oriented toward the inflow end of the frame.

In any or all of the disclosed embodiments, the first and second sealing members are disposed between the second strut members and the third strut members.

In any or all of the disclosed embodiments, the frame comprises an inflow end and an outflow end, and the prosthetic heart valve further comprises a conduit coupled to the outflow end of the frame and extending in an upstream direction from the frame.

In any or all of the disclosed embodiments, the conduit comprises a sealing member downstream of the prosthetic heart valve, and when the prosthetic heart valve is implanted in a native aortic valve, the sealing member is configured to form a seal in an ascending aorta, and the prosthetic heart valve is configured such that a portion of the blood flow through the prosthetic heart valve enters the conduit, and a portion of the blood flow through the prosthetic heart valve exits the prosthetic heart valve upstream of the sealing member and perfuses coronary arteries of the native aortic valve.

In any or all of the disclosed embodiments, the conduit comprises a stent frame coupled to the frame of the prosthetic heart valve, the stent frame being radially collapsible to a collapsed configuration and radially expandable to an expanded configuration independently of the frame of the prosthetic heart valve.

In any or all of the disclosed embodiments, the conduit comprises a covering, the covering comprising a sealing member comprising a first circumferential edge coupled to the covering and a free second circumferential edge.

In any or all of the disclosed embodiments, the stent frame comprises a plurality of strut members configured to bend radially outwardly from the stent frame into a curved shape when the stent frame is expanded to the expanded configuration.

In any or all of the disclosed embodiments, the stent frame is coupled to the frame of the prosthetic heart valve with a flexible coupling.

In another representative embodiment, a prosthetic heart valve that is radially collapsible to a collapsed configuration and radially expandable to an expanded configuration comprises an annular frame comprising a plurality of angled first strut members, the frame being configured to foreshorten from a first length corresponding to the collapsed configuration to a second length corresponding to the expanded configuration when the prosthetic heart valve is expanded to the expanded configuration. A leaflet structure is situated at least partially within the frame, and a plurality of second strut members extend longitudinally along at least a portion of the frame and are coupled to the frame. At least a portion of the second strut members comprise tissue-engaging members. At least respective portions of the second strut members are configured to bend radially outwardly into a curved shape as the frame moves from the collapsed configuration to the expanded configuration such that the tissue-engaging members extend outwardly from the second strut members.

In another representative embodiment, a prosthetic implant comprises a prosthetic heart valve that is radially collapsible to a collapsed configuration and radially expandable to an expanded configuration. The prosthetic heart valve comprises an annular frame comprising a plurality of angled first strut members, the frame being configured to foreshorten from a first length corresponding to the collapsed configuration to a second length corresponding to the expanded configuration when the prosthetic heart valve is expanded to the expanded configuration, the frame comprising an inflow end and an outflow end. A leaflet structure is situated at least partially within the frame, and a plurality of second strut members extend longitudinally along at least a portion of the frame and are coupled to the frame. At least respective portions of the second strut members are configured to bend radially outwardly into a curved shape as the frame moves from the collapsed configuration to the expanded configuration. A conduit is coupled to the outflow end of the frame and extends in an upstream direction from the frame.

In any or all of the disclosed embodiments, the prosthetic heart valve further comprises a plurality of longitudinally-oriented third strut members coupled to the frame, the third strut members being longitudinally offset from the second strut members along the frame and configured to bend into a curved shape as the frame moves from the collapsed configuration to the expanded configuration.

In any or all of the disclosed embodiments, the prosthetic heart valve further comprises a first sealing member extending circumferentially around the frame and coupled to the second strut members, the first sealing member being angled toward the outflow end of the frame. The prosthetic heart valve further comprises a second sealing member extending circumferentially around the frame and coupled to the third strut members, the second sealing member being angled toward the inflow end of the frame.

In any or all of the disclosed embodiments, the conduit further comprises a stent frame coupled to the frame of the prosthetic heart valve, the stent frame being radially collapsible to a collapsed configuration and radially expandable to an expanded configuration. The stent frame comprises a plurality of strut members configured to bend radially outwardly from the stent frame into a curved shape when the stent frame is expanded to the expanded configuration.

In another representative embodiment, a method comprises advancing the prosthetic implant of any of the disclosed embodiments to a treatment site in the radially collapsed state, inflating an inflatable expansion device to radially expand the prosthetic heart valve such that the frame foreshortens and the second strut members bend into the curved shape, deflating the inflatable expansion device, positioning the inflatable expansion device within the conduit, and inflating the inflatable expansion device within the conduit to at least partially expand the conduit.

The foregoing and other objects, features, and advantages of the disclosed technology will become more apparent from the following detailed description, which proceeds with reference to the accompanying figures.

BRIEF DESCRIPTION OF THE DRAWINGS

FIGS. 11A-14B illustrate various configurations of an exterior frame and locations where the exterior frame may be mounted an inner frame.

FIG. 13A is a side elevation view of the inner frame of FIG. 6 schematically illustrating the shape and coupling locations of struts of the exterior frame, according to another embodiment.

FIG. 13B illustrates the coupling locations of a strut member of the exterior frame on a laid-flat portion of the inner frame according to the embodiment of FIG. 13A.

FIG. 14A is a side elevation view of the inner frame of FIG. 6 schematically illustrating the shape and coupling locations of struts of the exterior frame, according to another embodiment.

FIG. 14B illustrates the coupling locations of a strut member of the exterior frame on a laid-flat portion of the inner frame according to the embodiment of FIG. 14A.

FIGS. 20 and 21 are schematic cross-sectional views of the prosthetic valve of FIGS. 6-10 illustrating radial expansion and axial shortening of the inner frame and corresponding radial expansion of the exterior frame.

FIG. 28A is a perspective view of another embodiment of an external frame in the collapsed configuration.

FIG. 28B illustrates the external frame of FIG. 28A in a laid-flat configuration.

FIG. 28C is a perspective view of a prosthetic heart valve including the external frame of FIGS. 28A and 28B.

FIG. 29 is a perspective view illustrating another embodiment of an external frame.

FIG. 36 is a perspective view of another embodiment of a prosthetic heart valve including an inner frame and a plurality of strut members coupled to the exterior of the frame.

FIG. 37 is a side elevation view of the prosthetic heart valve of FIG. 36.

FIGS. 47A-47C are side elevation views expansion of the inner frame and the exterior strut members of the prosthetic heart valve of FIG. 41.

FIG. 55 is a cross-sectional view of a frame of the conduit of the prosthetic implant of FIG. 54, according to one embodiment.

FIGS. 56A-56C are side elevation views illustrating radial expansion of the frame of FIG. 55.

DETAILED DESCRIPTION

The present disclosure concerns embodiments of prosthetic heart valves, and prosthetic devices or implants including such prosthetic valves, which include an inner frame and a plurality of strut members configured to bow, arch, or curve radially outwardly from the inner frame as the inner frame moves from a collapsed configuration to an expanded configuration. The outwardly curved strut members can aid in anchoring the prosthetic heart valve in a body lumen without substantially increasing the crimped profile of the implant. In certain embodiments, the strut members can be configured to bow or curve radially outwardly from the frame as the frame foreshortens from a relatively longer collapsed state to a relatively shorter expanded state. In certain embodiments, the strut members can be coupled or secured to the exterior of the frame, or can be integrally formed with the frame and configured to buckle outwardly as the frame expands and foreshortens. The struts can have a variety of lengths and configurations, depending upon the particular requirements of the implant. The struts can extend along the entire length of the valve, or a portion thereof. The prosthetic valves can comprise multiple sets of struts arrayed circumferentially around the inner frame of the valve, and longitudinally and/or circumferentially offset from each other. The struts can be coupled together to form an external frame that can be situated around the inner frame and coupled thereto. The external frame can be configured to form a barrel-shaped portion around the inner frame and a flange-shaped portion extending from one end of the inner frame.

The prosthetic heart valves described herein can also be incorporated into a variety of prosthetic implants, such as graft conduits. In certain configurations, the graft conduits can also include frames having strut members configured to bow or curve radially outwardly as the frame(s) of the conduit expand. Such implants can be useful for bypassing diseased portions of a blood vessel, such as aneurysms. In certain embodiments, the frame(s) of such conduits can be independently expandable such that the prosthetic valve frame and the conduit frame(s) can be expanded in a sequence using existing delivery systems, and need not require specially sized or shaped expansion mechanisms. Incorporating a plurality of such frames can allow the conduits to have any specified length.

Figure 1:
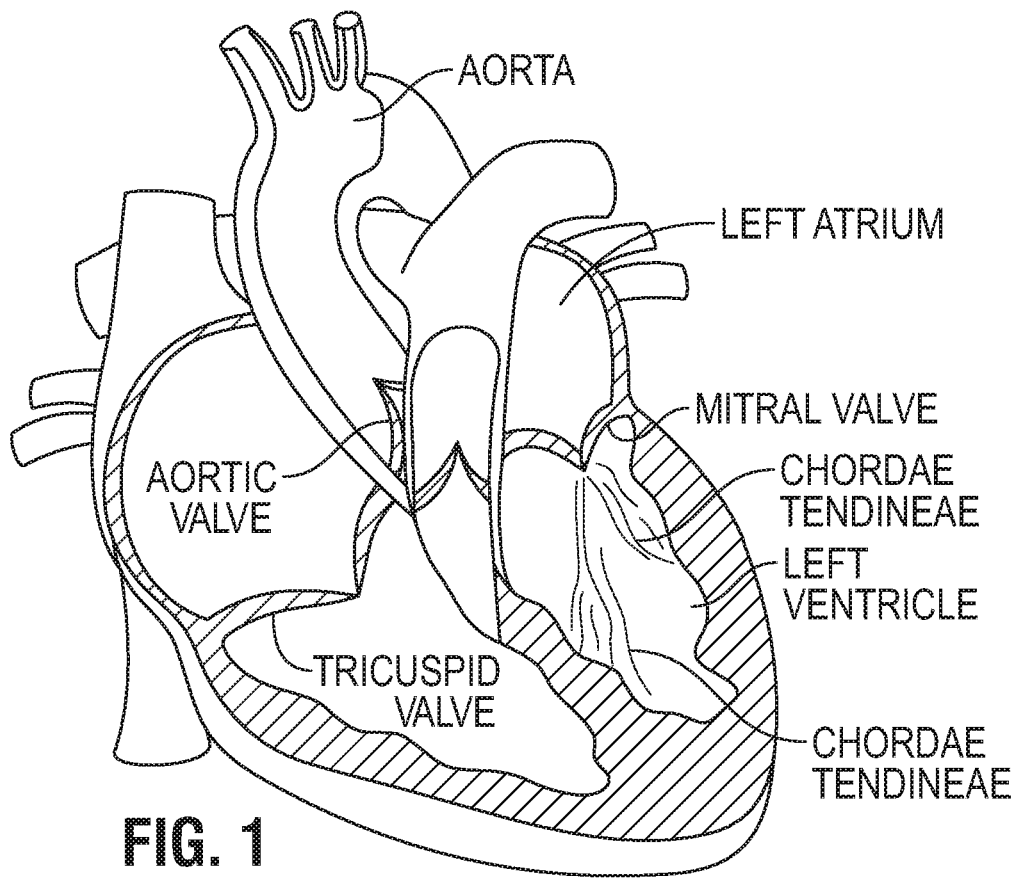
FIG. 1 shows a schematic cross-sectional view of a human heart.
Figure 2:
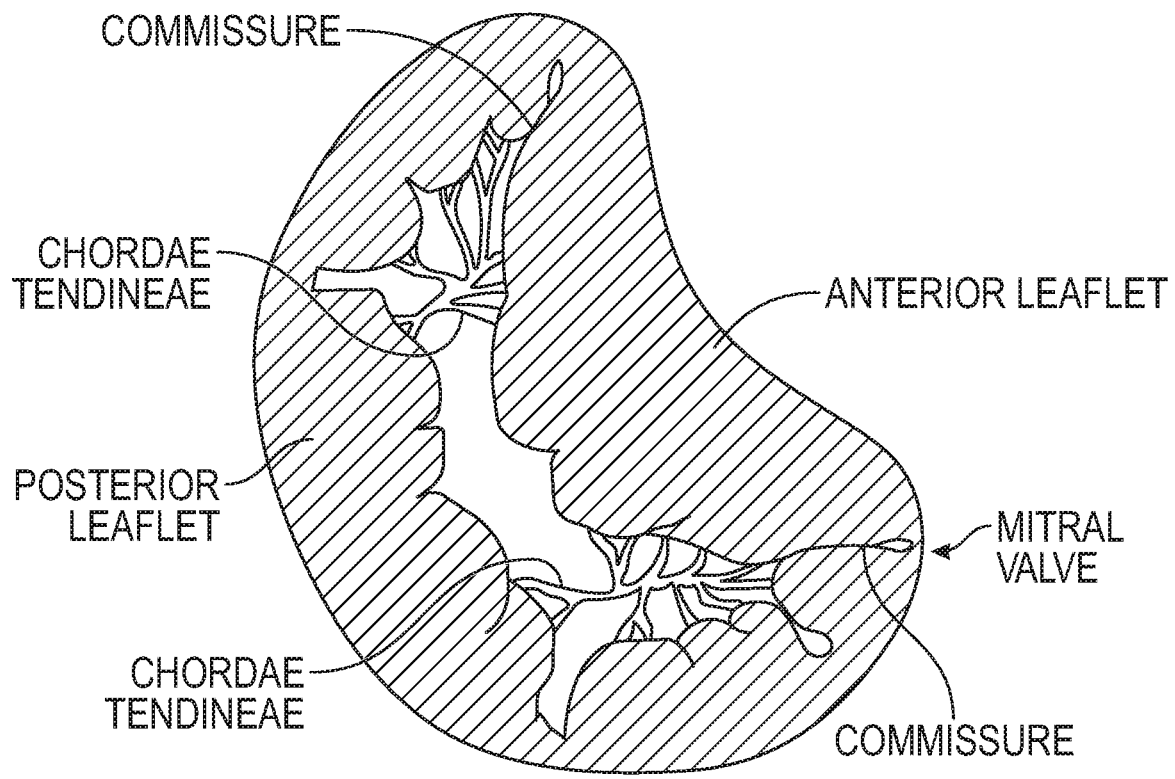
FIG. 2 shows a schematic top view of a mitral valve annulus of a heart.

Embodiments of the disclosed prosthetic heart valves can be configured for implantation at various locations within the heart (the native aortic, mitral, pulmonary, or tricuspid valves). A representative example is a prosthetic heart valve for replacing the function of the native mitral valve. FIGS. 1 and 2 illustrate the mitral valve of the human heart. The mitral valve controls the flow of blood between the left atrium and the left ventricle. After the left atrium receives oxygenated blood from the lungs via the pulmonary veins, the mitral valve permits the flow of the oxygenated blood from the left atrium into the left ventricle. When the left ventricle contracts, the oxygenated blood that was held in the left ventricle is delivered through the aortic valve and the aorta to the rest of the body. Meanwhile, the mitral valve closes during ventricular contraction to prevent blood from flowing back into the left atrium.

When the left ventricle contracts, the blood pressure in the left ventricle increases substantially, which urges the mitral valve closed. Due to the large pressure differential between the left ventricle and the left atrium during this time, a possibility of prolapse, or eversion of the leaflets of the mitral valve back into the atrium, arises. A series of chordae tendineae therefore connect the leaflets of the mitral valve to papillary muscles located on the walls of the left ventricle, where both the chordae tendineae and the papillary muscles are tensioned during ventricular contraction to hold the leaflets in the closed position and to prevent them from extending back towards the left atrium. This generally prevents backflow of oxygenated blood back into the left atrium. The chordae tendineae are schematically illustrated in both the heart cross-section of FIG. 1 and the top view of the mitral valve of FIG. 2.

A general shape of the mitral valve and its leaflets as viewed from the left atrium is shown in FIG. 2. Various complications of the mitral valve can potentially cause fatal heart failure. One form of valvular heart disease is mitral valve leak or mitral regurgitation, characterized by abnormal leaking of blood from the left ventricle through the mitral valve back into the left atrium. This can be caused by, for example, dilation of the left ventricle, which can cause incomplete coaptation of the native mitral leaflets resulting in leakage through the valve. Mitral valve regurgitation can also be caused by damage to the native leaflets. Another form of valvular heart disease is mitral valve stenosis, in which the passage through the mitral valve is narrowed due to, for example, calcium deposits or calcification around the mitral valve annulus, resulting in reduced blood from the left atrium into the ventricle during diastole. In these circumstances, it may be desirable to repair the mitral valve, or to replace the functionality of the mitral valve with that of a prosthetic heart valve, such as a transcatheter heart valve.

Figure 3:
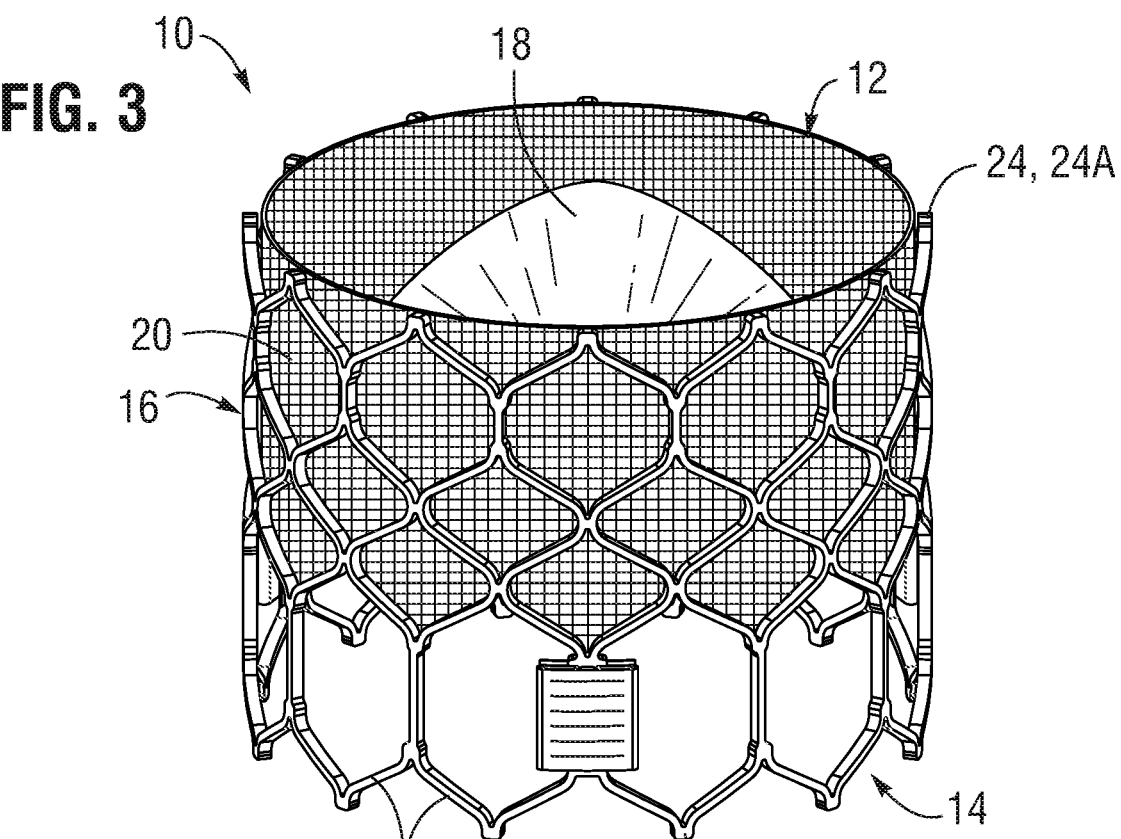
FIG. 3 is a perspective view of a prosthetic heart valve oriented with the inflow end up in the position for implantation in the mitral valve, according to one embodiment.
Figure 4:
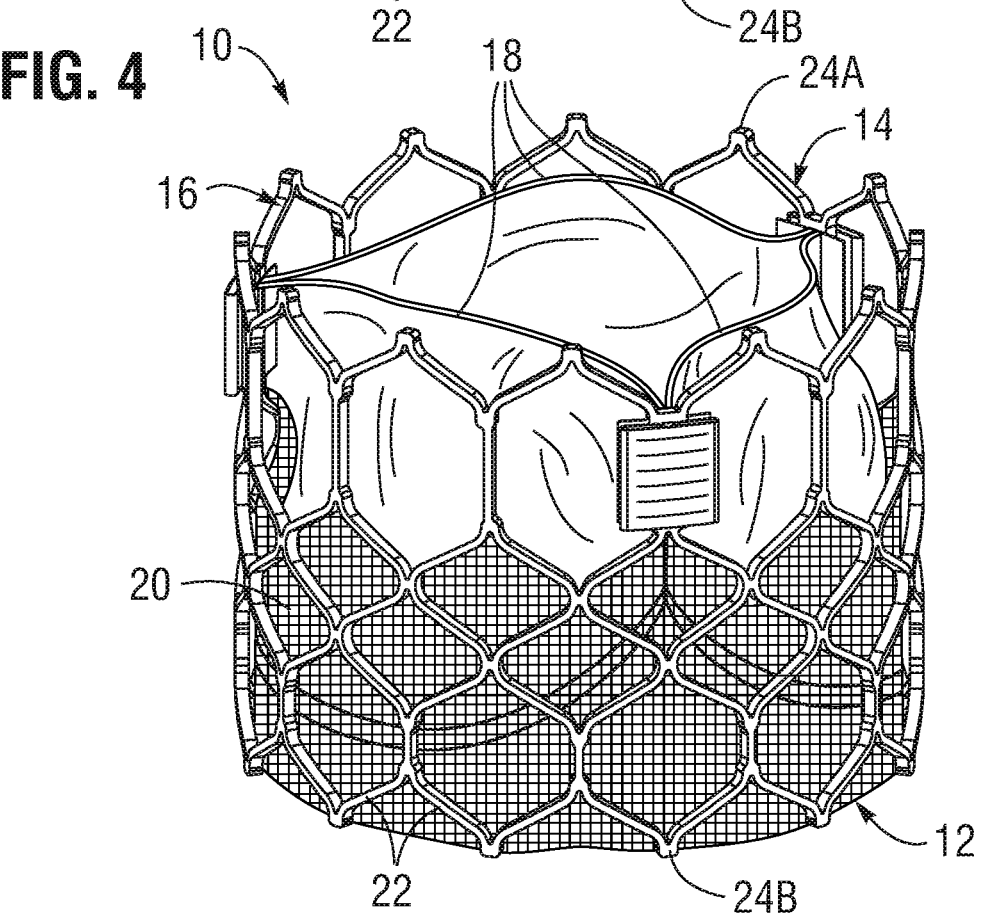
FIG. 4 is a perspective view of a portion of the frame of the prosthetic heart valve of FIG. 3 with the outflow end up.

Some transcatheter heart valves are designed to be radially crimped or compressed to facilitate endovascular delivery to an implant site at a patient's heart. Once positioned at a native valve annulus, the replacement valve is then expanded to an operational state, for example, by an expansion balloon, such that a leaflet structure of the prosthetic heart valve regulates blood flow through the native valve annulus. In other cases, the prosthetic valve can be mechanically expanded to the operational state, or can radially self-expand from a compressed delivery state under its own resiliency when released from a delivery sheath. One embodiment of a prosthetic heart valve is illustrated in FIGS. 3 and 4. A transcatheter heart valve with a valve profile and construction similar to the prosthetic valve shown in FIGS. 3 and 4 is the Edwards Lifesciences SAPIEN 3™ valve, which is described in detail in U.S. Publication No. 2012/0123529, which is incorporated herein by reference.

FIG. 3 is a top perspective view of the prosthetic valve 10 in the orientation in which it is intended to be implanted in the mitral valve, and FIG. 4 is a bottom perspective view. The prosthetic valve 10 in FIGS. 3 and 4 has an inflow end 12 and an outflow end 14, includes a frame or stent 16, and a leaflet structure comprising a plurality of leaflets 18 supported inside the frame 16. In the illustrated embodiment, the leaflet structure includes three leaflets 18 configured to collapse in a tricuspid arrangement (FIG. 4) similar to the native aortic valve, although the prosthetic valve can also include two leaflets configured to collapse in a bicuspid arrangement in the manner of the native mitral valve, or more than three leaflets, as desired. In some embodiments, a skirt 20 can be attached to an inner surface of the frame 10 to serve as an attachment surface for the valve leaflets 18.

Figure 5:
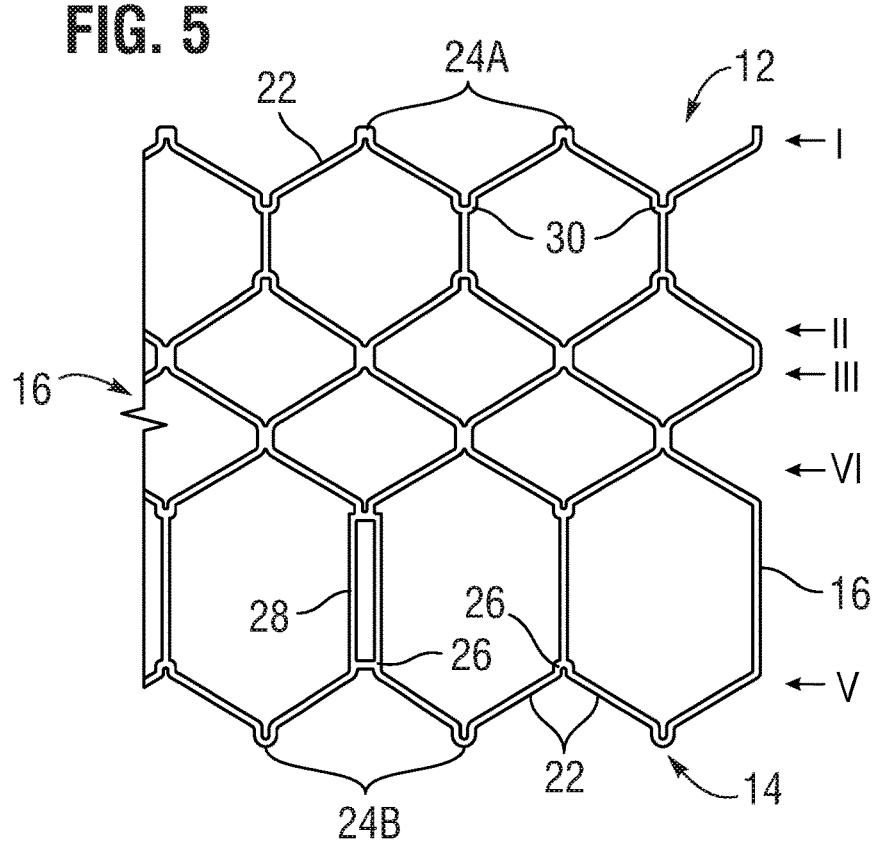
FIG. 5 illustrates a portion of a frame of the prosthetic heart valve of FIG. 3 in laid-flat configuration for purposes of illustration.

The frame 16 can be formed by a plurality of angled strut members 22, which can form a plurality of apices 24 arranged around the inflow and outflow ends of the frame. More specifically, the struts 22 can form a plurality of inflow apices 24A at the inflow end 12 of the frame, and a plurality of outflow apices 24B at the outflow end 14 of the frame. FIG. 5 illustrates a portion of the frame 16 in a laid-flat configuration for purposes of illustration. The strut members 22 can be arranged end-to-end to form a plurality of rows or rungs of strut members that extend circumferentially around the frame 16. For example, with reference to FIG. 5, the frame 16 can comprise a first or lower row I of angled strut members forming the inflow end 12 of the frame; a second row II of strut members beneath the first row; a third row III of strut members beneath the second row; a fourth row IV of strut members beneath the third row, and a fifth row V of strut members beneath the fourth row and forming the outflow end 14 of the frame.

At the outflow end 14 of the frame, the strut members 22 of the fifth row V can be arranged at alternating angles in a zig-zag pattern. The strut members 22 of the fifth row V can be joined together at their distal ends (relative to the direction of implantation in the mitral valve) to form the outflow apices 24B, and joined together at their proximal ends at junctions 26. The frame 16 can also comprise a plurality of commissure windows 28 formed between the fourth row IV and the fifth row V of strut members 22. The commissure windows 28 can be angularly spaced apart from each other around the circumference of the frame 16, and can be configured to receive portions (e.g., commissure tabs) of the leaflets 18 therein to allow the leaflets 18 to coapt with each other and form commissures. In certain embodiments, the junctions 26 may form part of the commissure windows 28. Additional structure and characteristics of the rows I-V of strut members 22 are described in greater detail in U.S. Publication No. 2012/0123529, incorporated by reference above.

The frame 16 can be made of any bio-compatible expandable material that permits both crimping to a radially collapsed state and expansion back to the expanded functional state illustrated in FIGS. 3 and 4. For example, in embodiments where the prosthetic valve is a self-expandable prosthetic valve that expands to its functional size under its own resiliency, the frame 16 can be made of Nitinol or another self-expanding material. In other embodiments, the prosthetic valve can be a plastically expandable valve that is expanded to its functional size by a balloon or another expansion device, in which case the frame can be made of a plastically expandable material, such as stainless steel or a cobalt-chromium alloy. Other suitable materials can also be used.

FIGS. 6-9 illustrate another embodiment of a prosthetic heart valve 100 that is radially collapsible to a collapsed configuration and radially expandable to an expanded configuration. The prosthetic valve 100 can include an inflow end generally indicated at 102, and an outflow end generally indicated at 104. The prosthetic valve can further include a ventricular portion 106, a lower portion of which forms part of the outflow end 14, and an atrial portion 108 located at the inflow end 102 of the prosthetic valve. The ventricular portion 106 can comprise a covering or skirt 114, and the atrial portion 108 can comprise a covering or skirt 116. The skirts 114 and 116 are discussed in greater detail below with reference to FIGS. 22 and 23.

Figure 7:
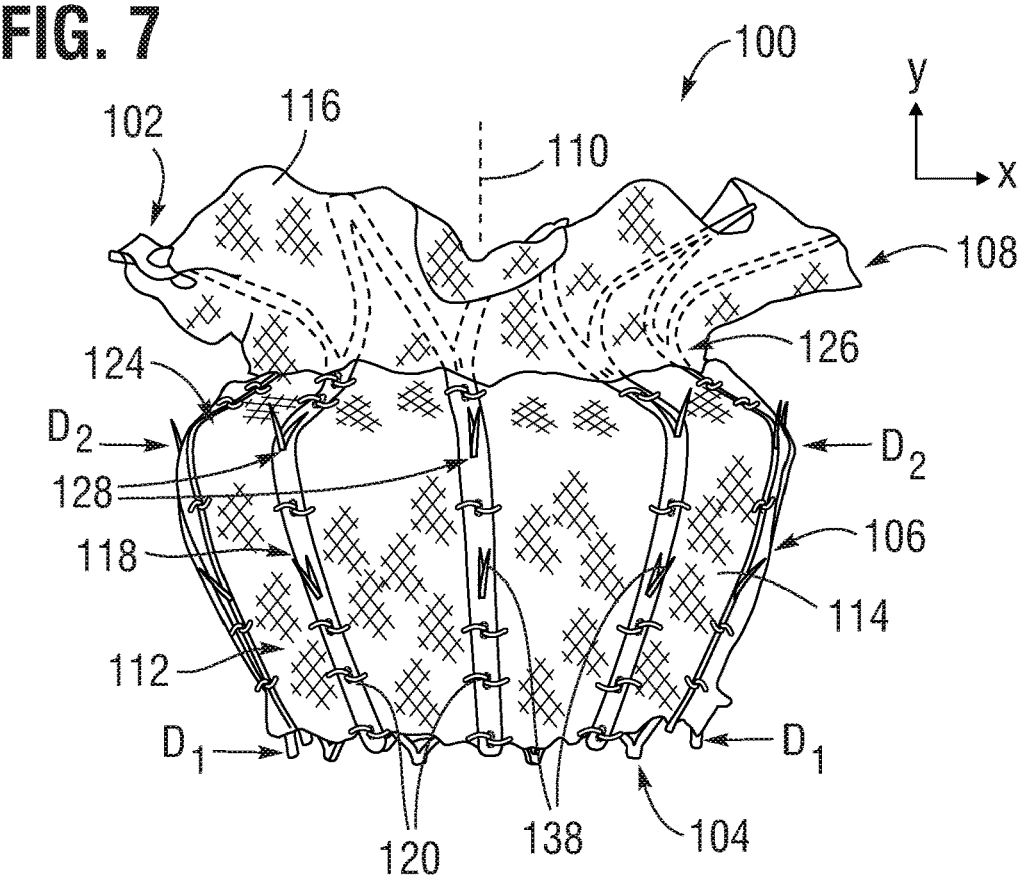
FIG. 7 is a side elevation view of the prosthetic heart valve of FIG. 6.

Referring to FIG. 7, in the expanded configuration the ventricular portion 106 can curve, bow, arch, or bulge radially outwardly relative to a longitudinal axis 110 of the prosthetic valve such that an exterior surface 112 of the ventricular portion 106 is convex. For example, in the illustrated embodiment the prosthetic valve can be shaped like a vase, wherein the ventricular portion 106 has a diameter $D_1$ at the outflow end 14 that increases in a direction toward the inflow end 102 along the positive y-axis (note Cartesian coordinate axes shown) to a maximum diameter $D_2$ at a shoulder 124. Continuing in a direction along the positive y-axis, the diameter of the ventricular portion 106 can decrease from the diameter $D_2$ back to approximately the diameter $D_1$ at a neck portion 126 that denotes the transition from the ventricular portion 106 to the atrial portion 108. In other embodiments, the diameter of the neck portion 126 can be larger or smaller than the diameter $D_1$ at the outflow end 14.

Figure 8:
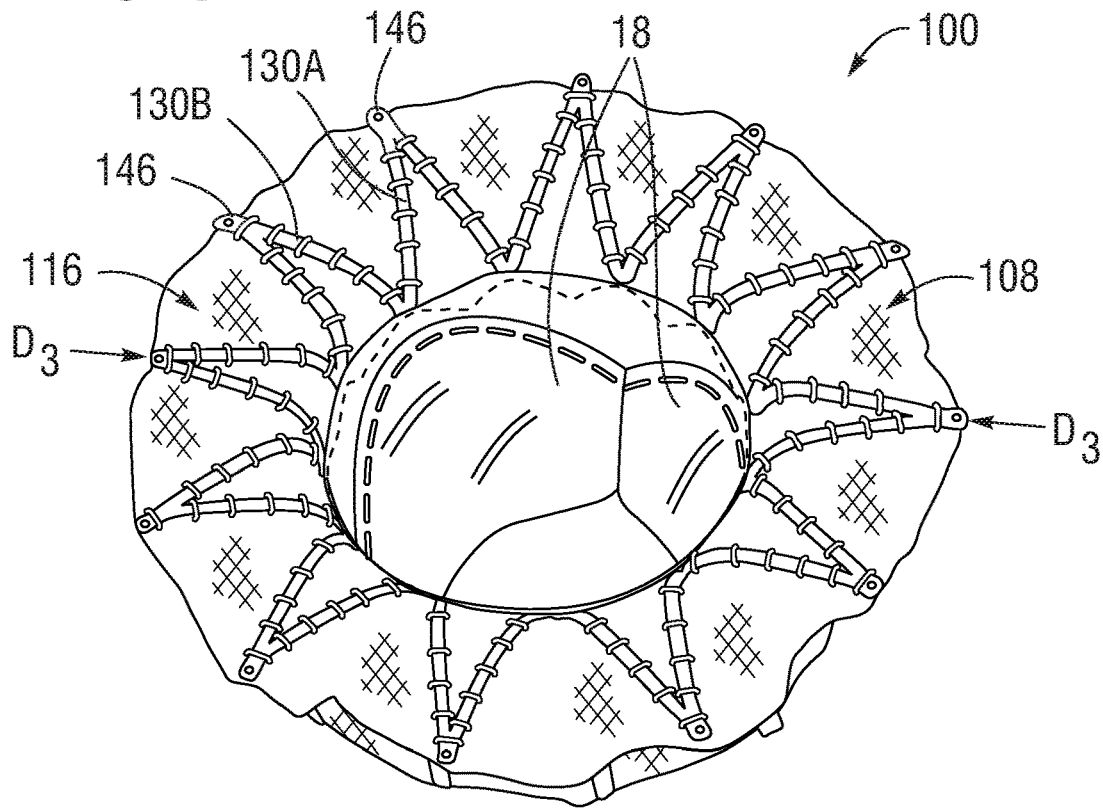
FIG. 8 is a top perspective view of the prosthetic heart valve of FIG. 6.

The atrial portion 104 can comprise an annular flange-like structure extending upwardly (e.g., proximally) and/or radially outwardly from the neck portion 126 proximate the inflow end 102 of the prosthetic valve. With reference to FIG. 8, in the illustrated embodiment the atrial portion 104 can have a diameter $D_3$ measured at diametrically opposite points on the edge of the atrial skirt member 116. In certain embodiments, the diameter $D_3$ of the atrial portion 108 can be greater than the diameter $D_2$ of the shoulder 124 of the ventricular portion.

Figure 9:
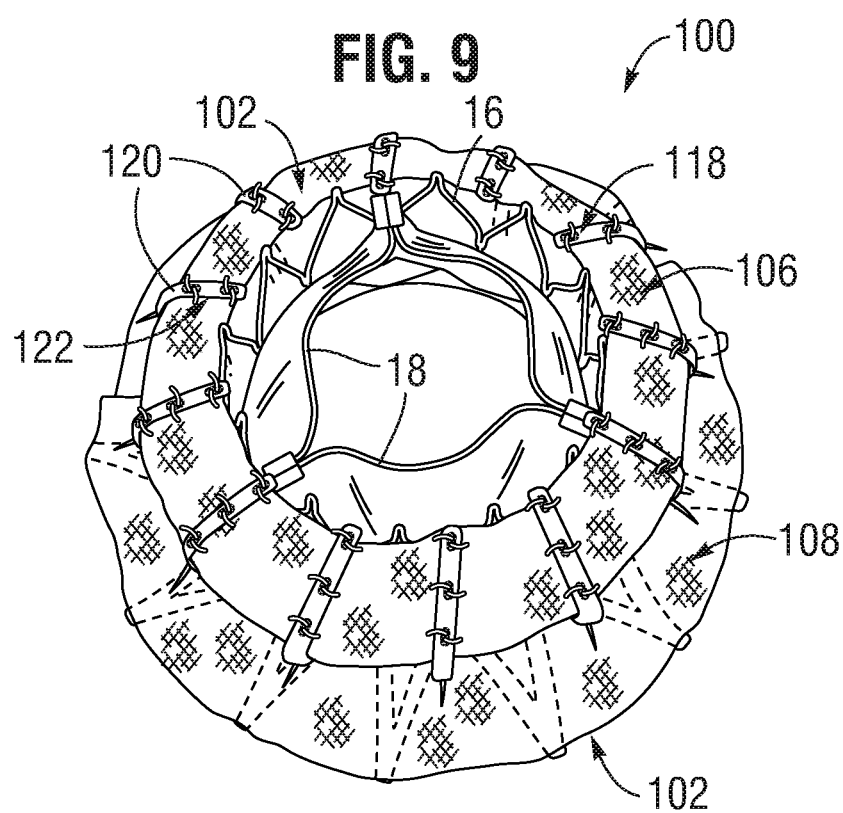
FIG. 9 is a bottom perspective view of the prosthetic heart valve of FIG. 6.
Figure 10:
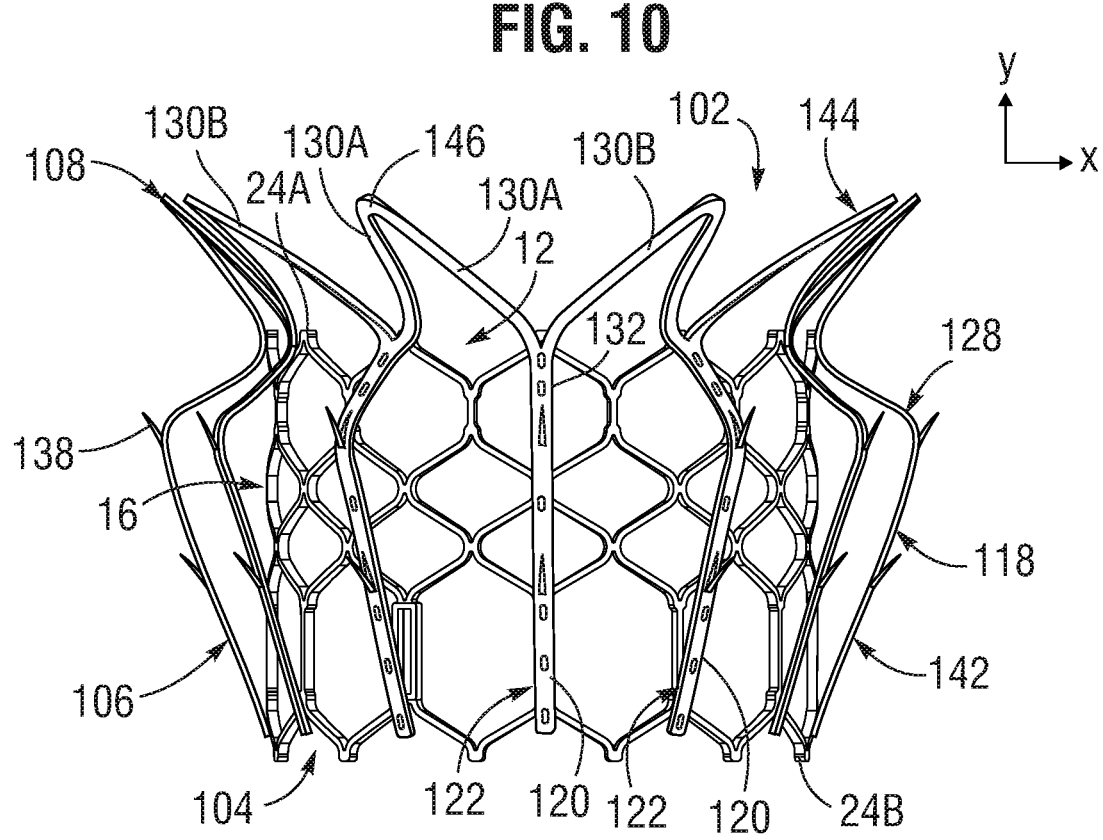
FIG. 10 is a side elevation view of the inner and outer frames of the prosthetic heart valve of FIG. 6.

FIG. 10 illustrates the prosthetic valve 100 with the skirts 114 and 116 removed for purposes of illustration. As illustrated in FIG. 10, the prosthetic valve 100 can comprise an inner frame configured as the frame 16 of the prosthetic valve 10 of FIGS. 3-5. As shown in FIGS. 8 and 9, the frame 16 can include the leaflets 18, the skirt 20, etc. (these components are removed from the frame in FIG. 10 for purposes of illustration). Referring again to FIG. 10, the prosthetic valve 100 can further comprise an outer frame 118 coupled to the inner frame 16, and configured to form the ventricular portion 106 and the atrial portion 108. The frame 118 can also be configured to move between the radially collapsed configuration and the radially expanded configuration together with the inner frame 16.

Figure 11A:
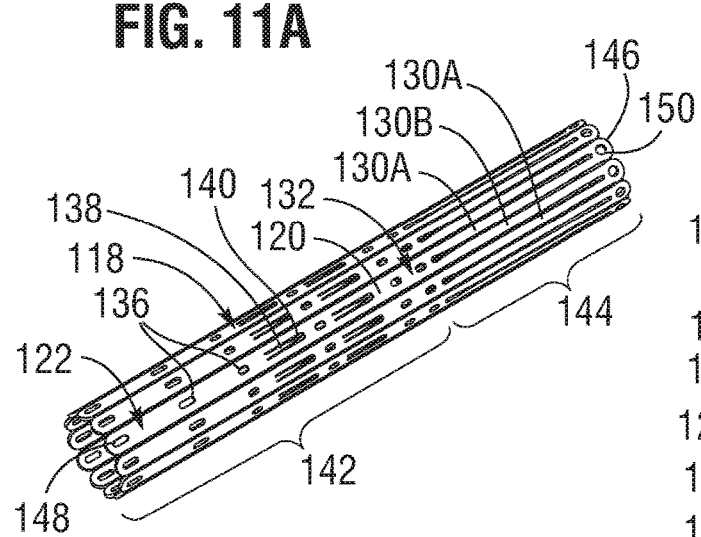
FIG. 11A is a perspective view of the exterior frame of the prosthetic heart valve of FIG. 6 is a radially collapsed state.

The outer frame 118 can comprise a plurality of strut members 120 circumferentially spaced apart from each other around the inner frame 16. The strut members 120 can be configured such that the outer frame 118 comprises a ventricular portion 142 corresponding to the ventricular portion 106 of the prosthetic valve 100, and an atrial portion 144 corresponding to the atrial portion 108 of the prosthetic valve 100. FIG. 11A illustrates a representative embodiment of the outer frame 118 in a radially collapsed configuration, and FIG. 11B illustrates a portion of the outer frame 118 of FIG. 11A in a laid-flat configuration for purposes of illustration.

Figure 6:
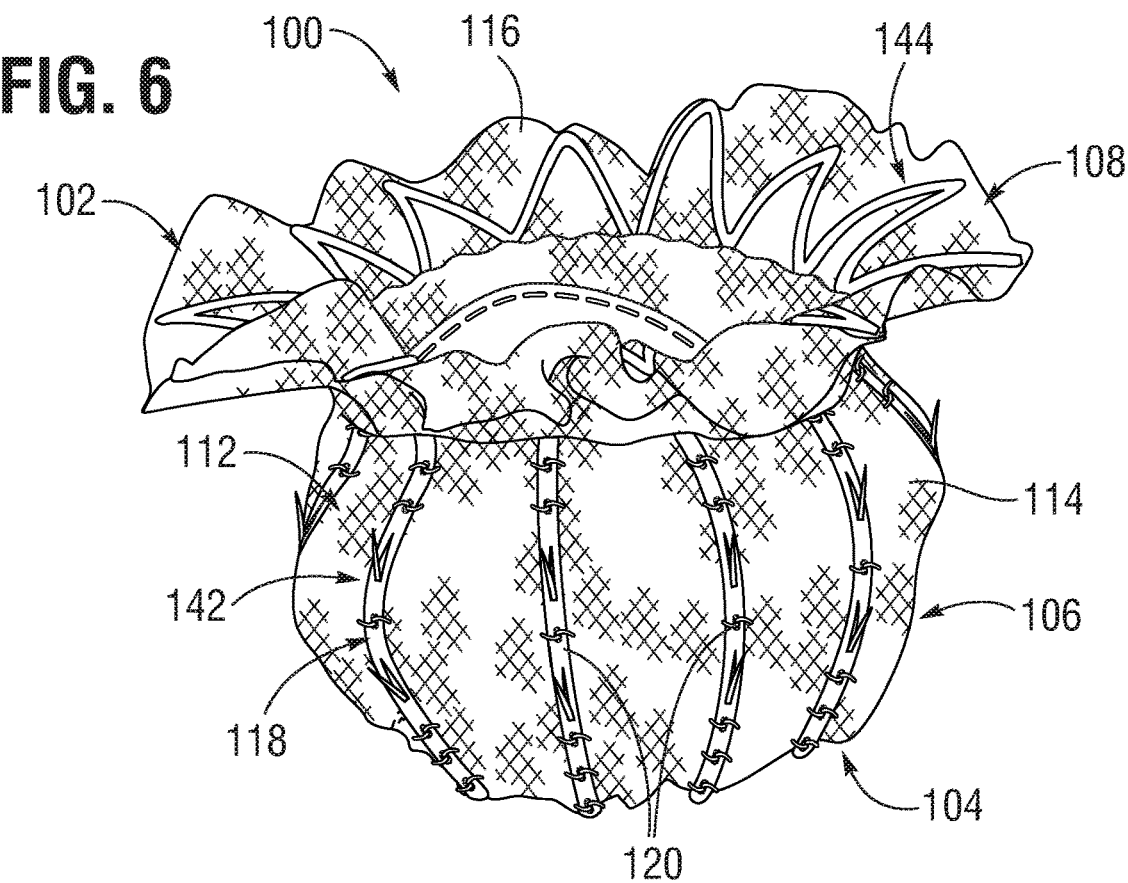
FIG. 6 is a perspective view illustrating another embodiment of a prosthetic heart valve including an exterior frame coupled to an inner frame.

Referring to FIGS. 7, 10, 11A, and 11B, the strut members 120 can comprise first end portions 122 and second end portions 132. With reference to FIGS. 12A and 12B (which schematically show the struts 120 coupled to the inner frame 16 for purposes of illustration), the first end portions 122 can be coupled to the fifth rung V of strut members 22 of the inner frame 16 at, for example, the junctions 26 between the outflow apices 24B. The second end portions 132 can be coupled to the inner frame 16 at the first rung I of strut members 22 at, for example, the inflow apices 24A. With reference to FIGS. 6 and 7, in the illustrated embodiment the first end portions 122 and the second end portions 132 of the struts 120 are coupled to the struts 22 by suturing, although the struts may also be coupled together by welding, brazing, adhesive, any combination thereof, and/or or other coupling means.

Referring to FIG. 7, in the expanded configuration, the strut members 120 can comprise apices or shoulders 128 corresponding to the shoulder 124 of the ventricular portion 106. The portions of the struts 120 between the first end portions 122 and the apices 128 can be angled away from the central axis 110 (FIG. 7) of the prosthetic valve such that the apices 128 are spaced radially apart from the inner frame 16. Moving in a direction along the positive y-axis from the apices 128 toward the inflow end 102, the strut members 120 can curve radially inwardly toward the inner frame 16 to the second end portions 132. The second end portions 132 can be configured as apices as well, and can be offset radially inwardly from the apices 128 and in a direction toward the inflow end 102 (e.g., proximally).

Figure 11B:
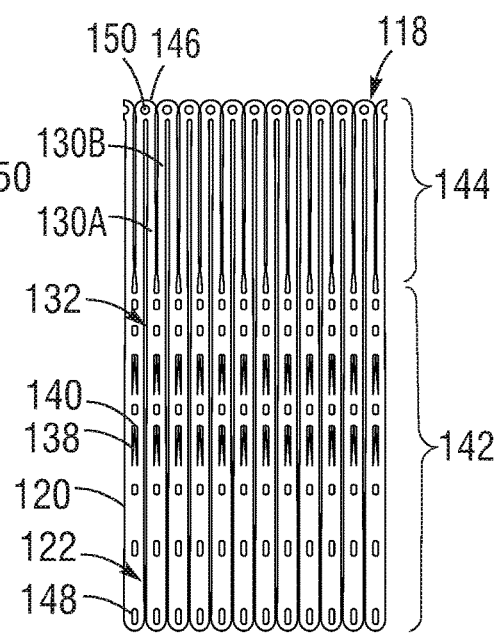
FIG. 11B illustrates a portion of the exterior frame of FIG. 11A in a laid-flat configuration.
Figure 12A:
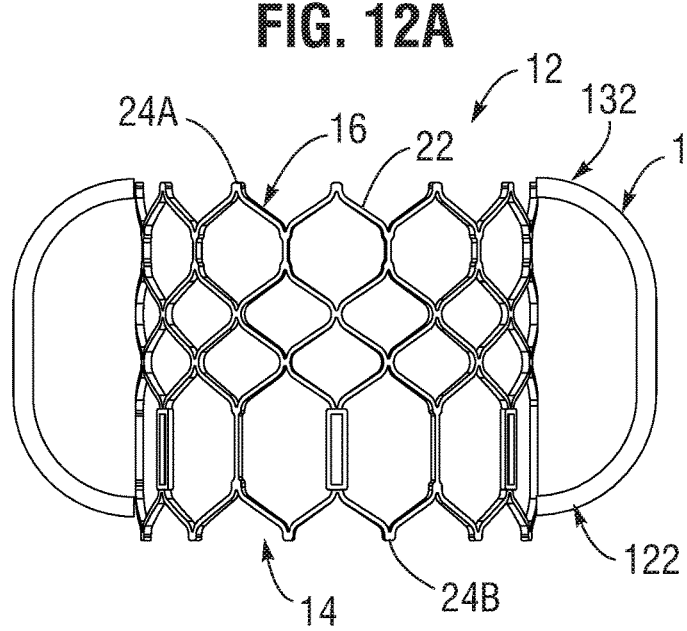
FIG. 12A is a side elevation view of the inner frame of FIG. 6 schematically illustrating the shape and coupling locations of struts of the exterior frame, according to one embodiment.
Figure 12B:
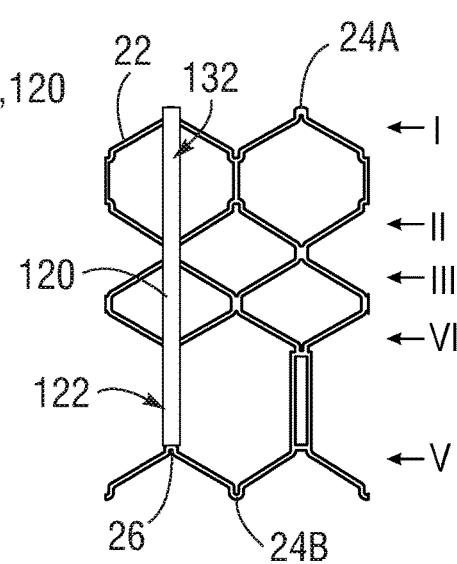
FIG. 12B illustrates the coupling locations of a strut member of the exterior frame on a laid-flat portion of the inner frame according to the embodiment of FIG. 12A.

Referring to FIGS. 10, 11A, and 11B, at or proximate to the second end portions 132, each of the strut members 120 can split or divide into two strut members 130A and 130B, which are collectively referred to herein as "atrial strut members." In the illustrated embodiment, in the expanded configuration the atrial strut members 130A and 130B of each strut member 120 can diverge circumferentially from each other beginning at the second end portions 132. The atrial strut members 130A, 130B can then merge with the adjacent strut member 130A or 130B of the adjacent strut member 120 to form proximal apices 146 at the inflow end 102 of the prosthetic valve. In the embodiment illustrated in FIGS. 6-12B, the second end portions 132 of the struts 120 are adjacent or contacting the inflow end 12 of the inner frame 16. Referring to FIG. 10, moving in the direction of the positive y-axis (e.g., in the proximal or upstream direction), the struts 130A and 130B can curve radially outwardly from their origins at the second end portions 132 such that the proximal apices 146 are spaced radially outward from the inflow end 12 of the inner frame 16 to form the atrial portion 108.

FIG. 11A illustrates the outer frame 118 in a radially collapsed state. The strut members 120 can comprise a plurality of openings 136 spaced axially along the length of the struts 120. The openings 136 can provide locations for suture attachment between the inner frame 16 and the outer frame 118, and/or between the strut members 120 and the ventricular skirt 114. More specifically, the first end portions 122 of the struts 120 can comprise round or circular atraumatic suture openings 148, and the apices 146 formed by the respective pairs of atrial strut members 130A and 130B can comprise round or circular atraumatic suture openings 150.

The strut members 120 can also comprise a plurality of tissue-engaging elements configured as pointed prongs or barbs 138. The barbs 138 can be situated within respective openings 140 defined in the strut members 120. In certain embodiments, the barbs 138 can be configured such that they are positioned within their respective opening 140 when the outer frame 118 is in the radially collapsed state (FIG. 11A), and can point outwardly from the openings 140 when the frame 118 is in the expanded state to engage surrounding tissue (FIGS. 7 and 10). In the configuration illustrated in FIGS. 11A and 11B, the frame comprises two rows of barbs 138 located between the first end portions 122 and the second end portions 132 of the struts 120. However, the frame can comprise a single row of barbs, more than two rows of barbs (see FIGS. 28A-28C), or no barbs (FIG. 29), depending upon the particular application.

The ventricular strut members 120 and/or the atrial strut members 130A, 130B of the outer frame 118 can be coupled to the inner frame 16 at any of various locations on the inner frame 16. For example, FIGS. 12A-12B schematically illustrate the first end portions 122 of the strut members 120 of the outer frame 118 coupled to the junctions 26 of the fifth row V of strut members 22 of the inner frame 16. In this configuration, the second end portions 132 of the strut members 120 can be coupled to the inflow apices 24A and/or at the first row I of strut members 22 of the inner frame 16. In FIGS. 12A-12B, along with FIGS. 13A-13B and 14A-14B discussed below, the atrial strut members 130A and 130B are omitted for ease of illustration, but can be present in any of the disclosed embodiments. Referring to FIGS. 13A and 13B, the first end portions 122 of the struts 120 may also be coupled to the outflow apices 24B of the inner frame, and the second end portions 132 can be coupled to junctions 30 of the strut members 22 of the first row I opposite the inflow apices 24A. Referring to FIGS. 14A and 14B, in another embodiment the first end portions 122 can be coupled to the fourth row IV of strut members 22, and the second end portions 132 can be coupled to the inflow apices 24A. In the configuration shown in FIGS. 14A and 14B, the strut members 120 can be shorter than in the previous, although in other embodiments the struts can be configured to extend outwardly from the frame by a greater distance than in the configurations shown in FIGS. 12A-12B and 13A-13B. Varying the length and attachment points of the strut members 120 can vary the size and shape of the resulting ventricular portion 106 of the prosthetic valve when the prosthetic valve is expanded.

In certain embodiments, the outer frame 118 can be made from self-expanding materials such as Nitinol, or from plastically expandable materials such as stainless steel or a cobalt-chromium alloy. In certain embodiments, the outer frame 118 can be laser cut from metal tube in a pattern similar to that shown in FIG. 11A. In other embodiments, the struts of the outer frame 118 can be separately formed and attached to each other by, for example, welding or brazing.

Figure 15:
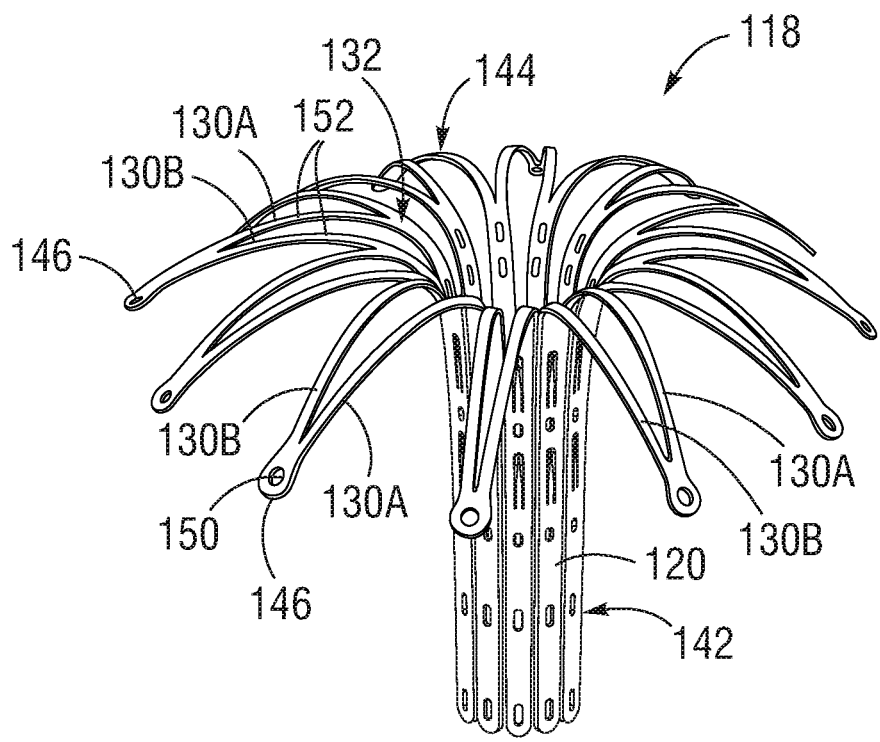
FIG. 15 is a perspective view of the exterior frame of the prosthetic heart valve of FIG. 6 with the ventricular portion in the collapsed configuration and the atrial portion shape set into a flange shape.

In certain embodiments, the atrial strut members 130A and 130B can be shape-set to have a curved, outwardly-extending shape prior to assembly of the outer frame 118 on to the inner frame 16. FIG. 15 illustrates the outer frame 118 in the radially collapsed state with the atrial strut members 130A and 130B shape-set such that they curve upwardly and radially outwardly from the second end portions 132 of the ventricular strut members 120 and form an umbrella-shaped array about the longitudinal axis of the outer frame 118. Starting from the second end portions 132 of the struts 120 and moving along the struts 130A and 130B toward the apices 146, the struts 130A and 130B can initially extend upwardly, proximally, or upstream to apices generally indicated at 152, before curving downwardly or distally to the apices 146.

As noted above, in certain embodiments the atrial portion 104 can form a flange extending around the inflow end of the frame 16. The flange formed by the atrial portion 104 can be flat or planar, or can be curved with respect to one or more planes. For example, the flange formed by the atrial portion 104 in the illustrated embodiment can comprise a curving, wavy, or frilled radially outward edge where the covering 116 is draped between strut members 130A and 130B. The atrial portion 104 can be curved, crowned, or cambered radially outward and toward the outflow end of the inner frame (e.g., downwardly as in FIG. 15), or can curve or extend radially away from the inflow end similar to FIG. 10.

Figure 16:
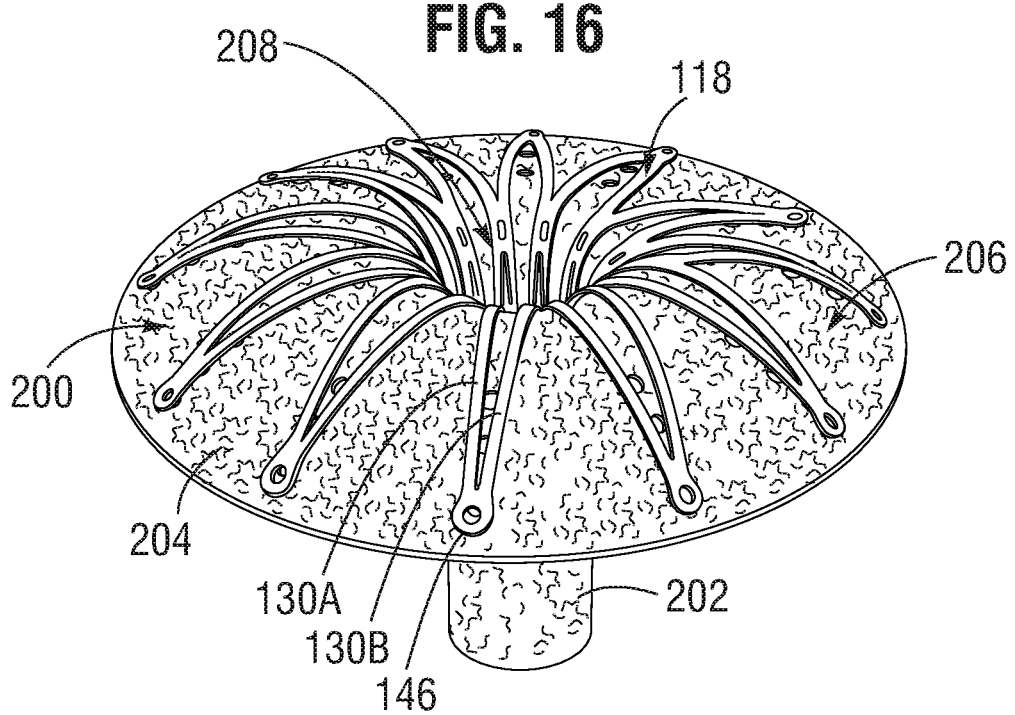
FIG. 16 illustrates the exterior frame of FIG. 15 situated in a mandrel, according to one embodiment.
Figure 17A:
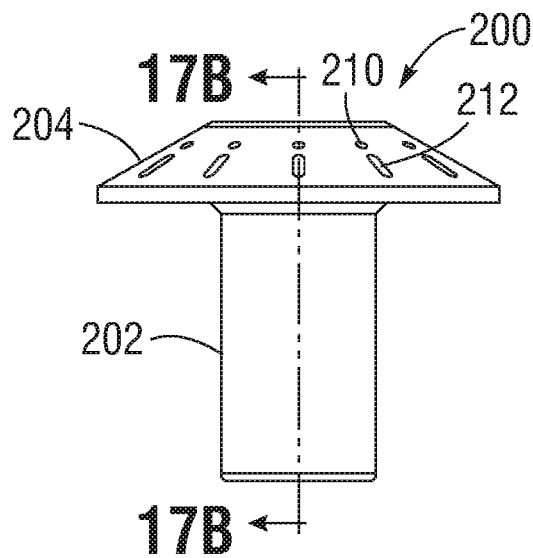
FIGS. 17A-17C are a side elevation view, a cross-sectional view, and a top plan view of the mandrel of FIG. 16.
Figure 17B:
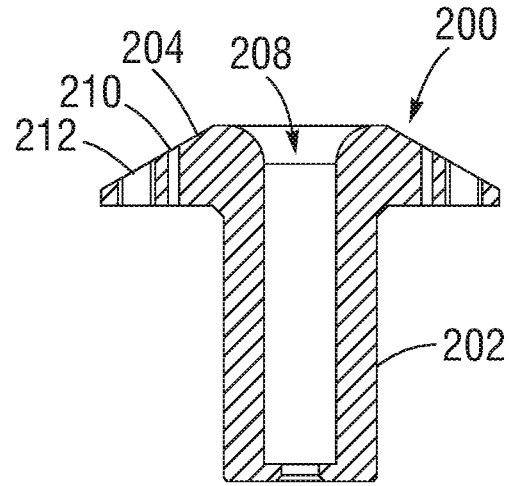
Figure 17C:
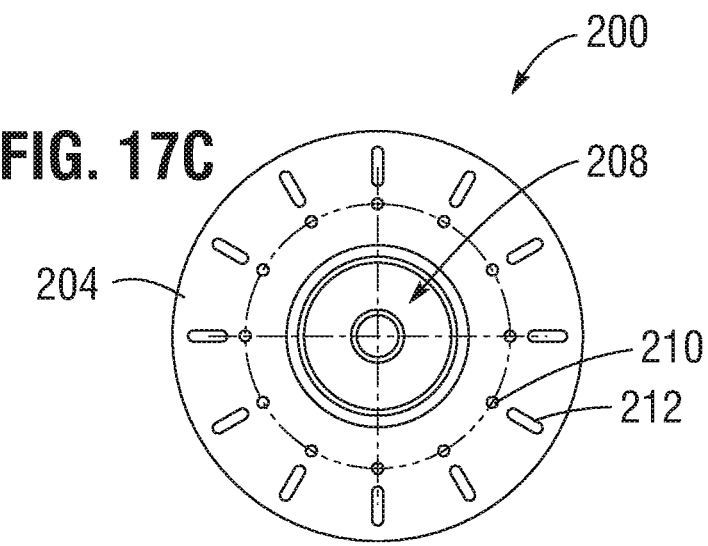

In certain embodiments, the curved shape of the atrial struts 130A, 130B can be obtained using a correspondingly shaped mandrel. FIG. 16 illustrates the outer frame 118 situated in a representative embodiment of a mandrel 200 that can be used to shape-set the atrial strut members 130A and 130B into the desired configuration. FIGS. 17A-17C illustrate the mandrel 200 in greater detail. The mandrel 200 can comprise a cylindrical first portion 202 and a second domed portion 204 extending radially outwardly from the first portion 202 and having a curved exterior surface 206. Referring to FIG. 17B, the first portion 202 of the mandrel can comprise a passage or lumen 208 extending along the length of the first portion 202 and configured to receive the cylindrically arranged struts 120. In certain embodiments, the atrial struts 130A and 130B of the outer frame 118 can be coupled or fastened to the second portion 204 (e.g., by tying with wire or suture) such that the struts 130A and 130B conform to the shape of the surface 206 and acquire a curved shape corresponding to the shape of the surface 206. For example, in the illustrated embodiment the second portion 204 of the mandrel can comprise a series of circumferentially arranged openings 210 and 212 through which suture, loops, or thread can be inserted to secure the struts 130A, 130B to the mandrel. In certain embodiments, the mandrel 200 can comprise a metal or metal alloy, and/or a high-temperature polymeric material such that the frame 118 can be shape set by application of heat.

Figure 18:
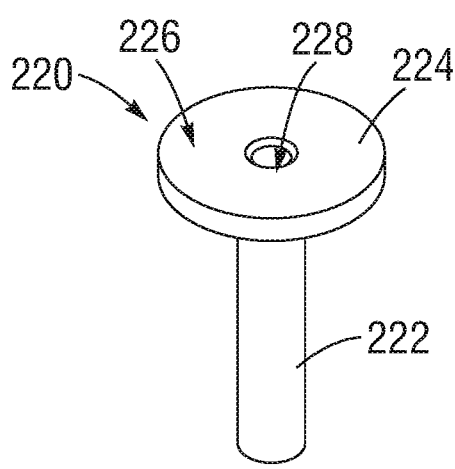
FIG. 18 is a perspective view of another embodiment of a mandrel.
Figure 19:
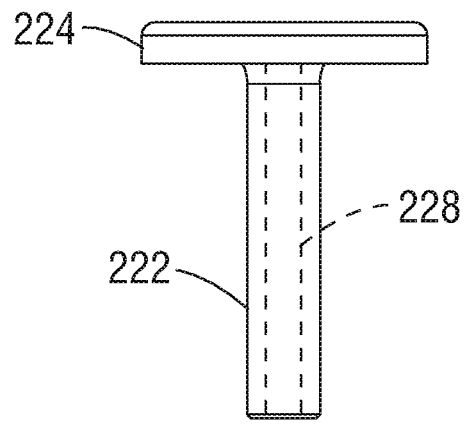
FIG. 19 is a side elevation view of another embodiment of a mandrel.

FIGS. 18 and 19 illustrate additional embodiments of mandrels that can be used to prepare or shape set the outer frame 118. The mandrel 220 in FIG. 18 comprises a cylindrical first portion 222, a cylindrical second portion 224 having a greater diameter than the first portion 222, and comprising a flat upper surface 226. A lumen 228 extends from the upper surface of the second portion 224 through the first portion 222. FIG. 19 illustrates another configuration in which the second portion 224 comprises a beveled edge.

In certain embodiments, the struts 120 can be shape-set to have a curved shape, such as by heat treatment, optionally in combination with a correspondingly-shaped mandrel.

FIG. 20 schematically illustrates the frame 16 and the frame 118 in the collapsed configuration. In the collapsed configuration, the ventricular strut members 120 of the frame 118 can be straight or nearly straight, and can be situated adjacent or against the exterior of the inner frame 16. In the collapsed configuration, the frame 16 can have a first length $L_1$. When the frame 16 is expanded to its functional size, the frame 16 can foreshorten as the angles between the strut members increase and the cells in the frame open. Thus, with reference to FIG. 21, when the frame assembly is expanded to the expanded configuration, the length of the frame 16 can shorten to a second length $L_2$. The reduction in length of the frame 16 can cause the ventricular strut members 120 of the frame 118 to bow or arch such that the struts 120 curve radially outwardly from the inner frame 16 to form the ventricular portion 106 of the prosthetic valve. Thus, in particular embodiments, by virtue of the attachment of the opposing end portions of the struts 120 to the inner frame 16 and the foreshortening of the inner frame, opposed axial forces are applied to the opposite ends of the struts 120, causing them to buckle outwardly and away from the inner frame 16. In embodiments in which the outer frame 118 comprises a self-expanding material, foreshortening of the inner frame 16 can resiliently flex or bend the struts 120. In embodiments in which the struts 120 are shape-set to a curved shape, foreshortening of the frame 16 can allow the struts to return to the shape-set curved shape.

The prosthetic valve 100 can be assembled by at least partially expanding a pre-assembled prosthetic valve 10 including a frame 16 and a leaflet structure, and expanding an outer frame 118 by a corresponding amount. The outer frame 118 can be situated around the frame 16, and the ventricular strut members 120 can be attached to the strut members 22 of the frame 16, as described above. The ventricular skirt 114 can be secured to the ventricular strut members 120 of the outer frame 118, and the atrial skirt 116 can be secured to the atrial strut members 130A, 130B of the outer frame.

Figure 22:
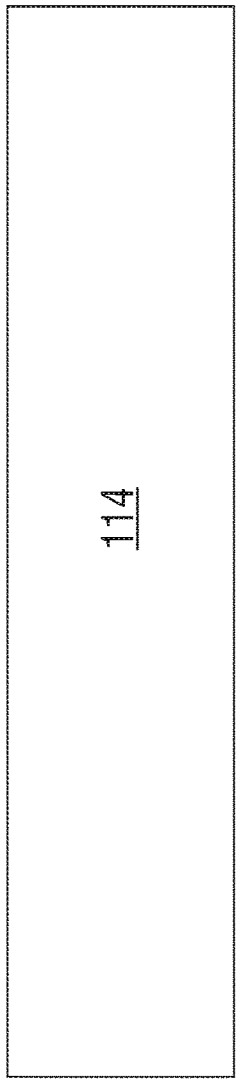
FIGS. 22 and 23 are top plan views of embodiments of skirts.

FIG. 22 illustrates the ventricular skirt 114 in greater detail. In the illustrated embodiment, the ventricular skirt 114 can comprise a rectangular piece of material. In certain embodiments, the ventricular skirt 114 can comprise for example, any of various woven fabrics, such as gauze, polyethylene terephthalate (PET) fabric (e.g., Dacron), polyester fabric, polyamide fabric, or any of various non-woven fabrics, such as felt. In certain embodiments, the ventricular skirt can also comprise a film including any of a variety of crystalline or semi-crystalline polymeric materials, such as polytetrafluoroethylene (PTFE), PET, polypropylene, polyamide, polyetheretherketone (PEEK), etc. As the prosthetic valve expands, the struts 120 can pull the skirt 114 into the barrel or convex shape shown in FIGS. 6 and 28C.

Figure 23:
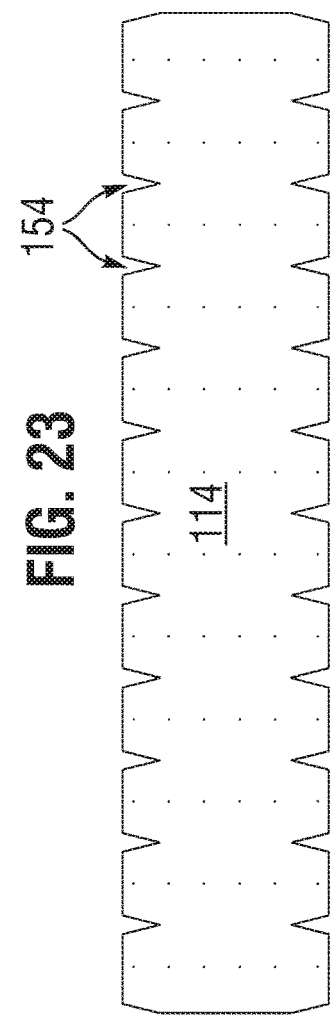

Another embodiment of the ventricular skirt 114 is illustrated in FIG. 23, in which the skirt includes recesses or notches 154. In certain embodiments, the notches 154 can allow the skirt 114 to accommodate the struts 120 at their various connections to the inner frame 16.

Figure 24:
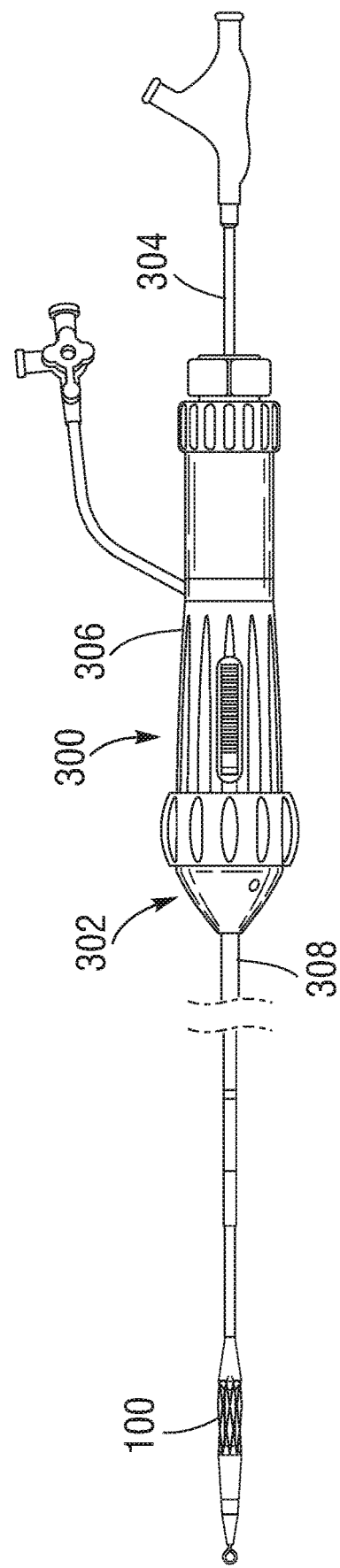
FIG. 24 is a side elevation view of a delivery apparatus, according to one embodiment.

In use, the prosthetic valve 100 can be crimped onto a delivery apparatus for delivery to the treatment site. FIG. 24 illustrates a representative embodiment of a delivery apparatus 300 that can be used to deliver a prosthetic heart valve to a patient. The delivery apparatus 300 is exemplary only, and can be used in combination with any of the prosthetic heart valve embodiments described herein. Likewise, the prosthetic heart valves disclosed herein can be used in combination with any of various known delivery apparatuses. The delivery apparatus 300 illustrated can generally include a steerable guide catheter 302 and a balloon catheter 304 extending through the guide catheter 302. A prosthetic device, such as a prosthetic heart valve shown schematically at 100, can be positioned on the distal end of the balloon catheter 304. The guide catheter 302 and the balloon catheter 304 can be adapted to slide longitudinally relative to each other to facilitate delivery and positioning of the prosthetic heart valve 100 at an implantation site in a patient's body. The guide catheter 302 includes a handle portion 306 and an elongated guide tube or shaft 308 extending from the handle portion 306.

Figure 25:
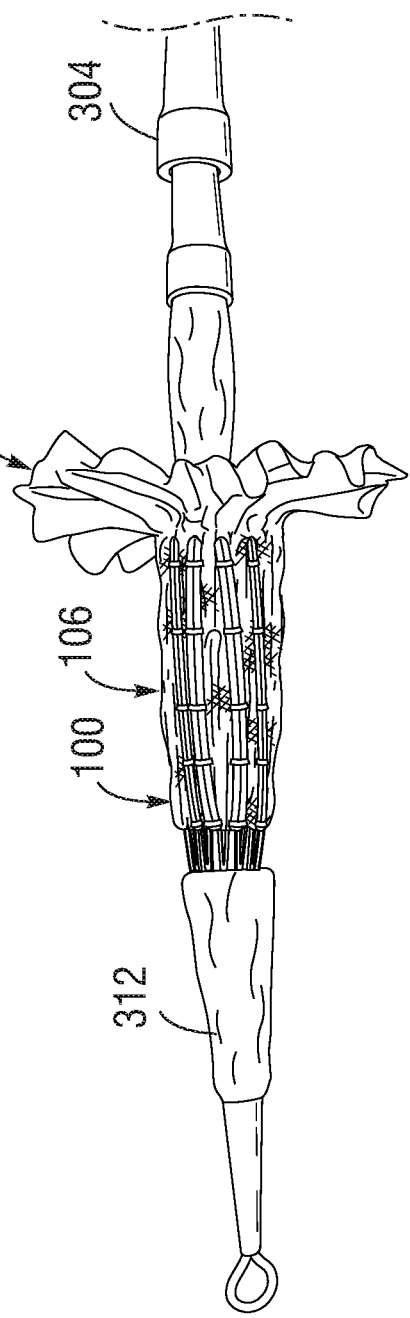
FIG. 25 is perspective view illustrating the prosthetic heart valve of FIGS. 6-10 crimped on an end portion of the delivery apparatus of FIG. 24.

FIG. 25 illustrates the prosthetic valve 100 crimped on a balloon 312 on the distal end portion of the balloon catheter 304. Due to the shape-set of the outer frame 118, the struts 130A and 130B of the atrial portion 108 can bend and extend radially away the collapsed ventricular portion 106.

Figure 26:
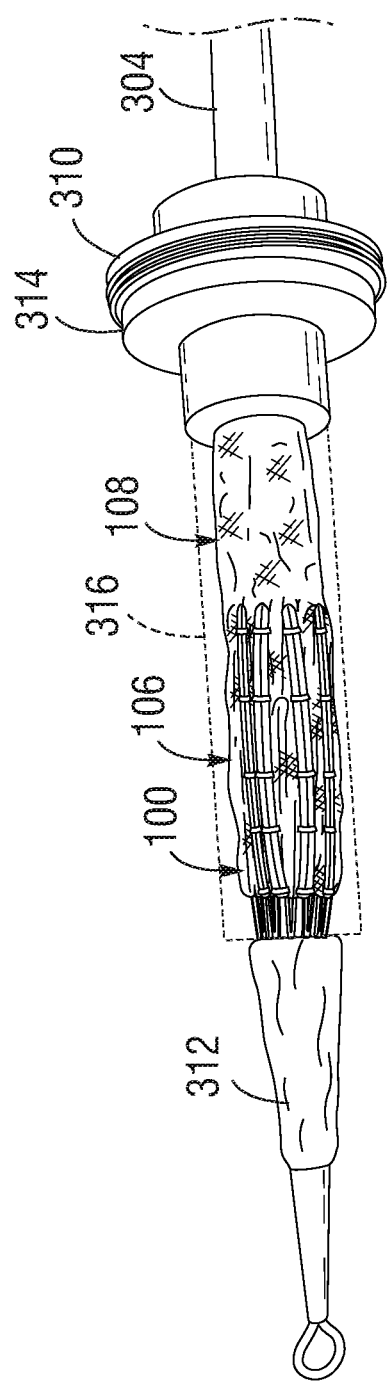
FIG. 26 is a perspective view illustrating the prosthetic heart valve of FIGS. 6-10 on the end portion of the delivery apparatus and enclosed within a sheath loader.

FIG. 26 illustrates the prosthetic valve 100 enclosed within a cap, capsule, or sheath loader 310 on the distal end of the balloon catheter 304. The loader 310 includes a first portion 314 shown in solid lines and a second portion 316 shown in dashed lines. The second portion 316 is configured as a sheath to receive the prosthetic valve 100 crimped around the balloon 312. The atrial portion 108 can be folded proximally such that it lies against the balloon 312 and/or against the balloon catheter 304, and is held in place by the loader 310.

Figure 27:
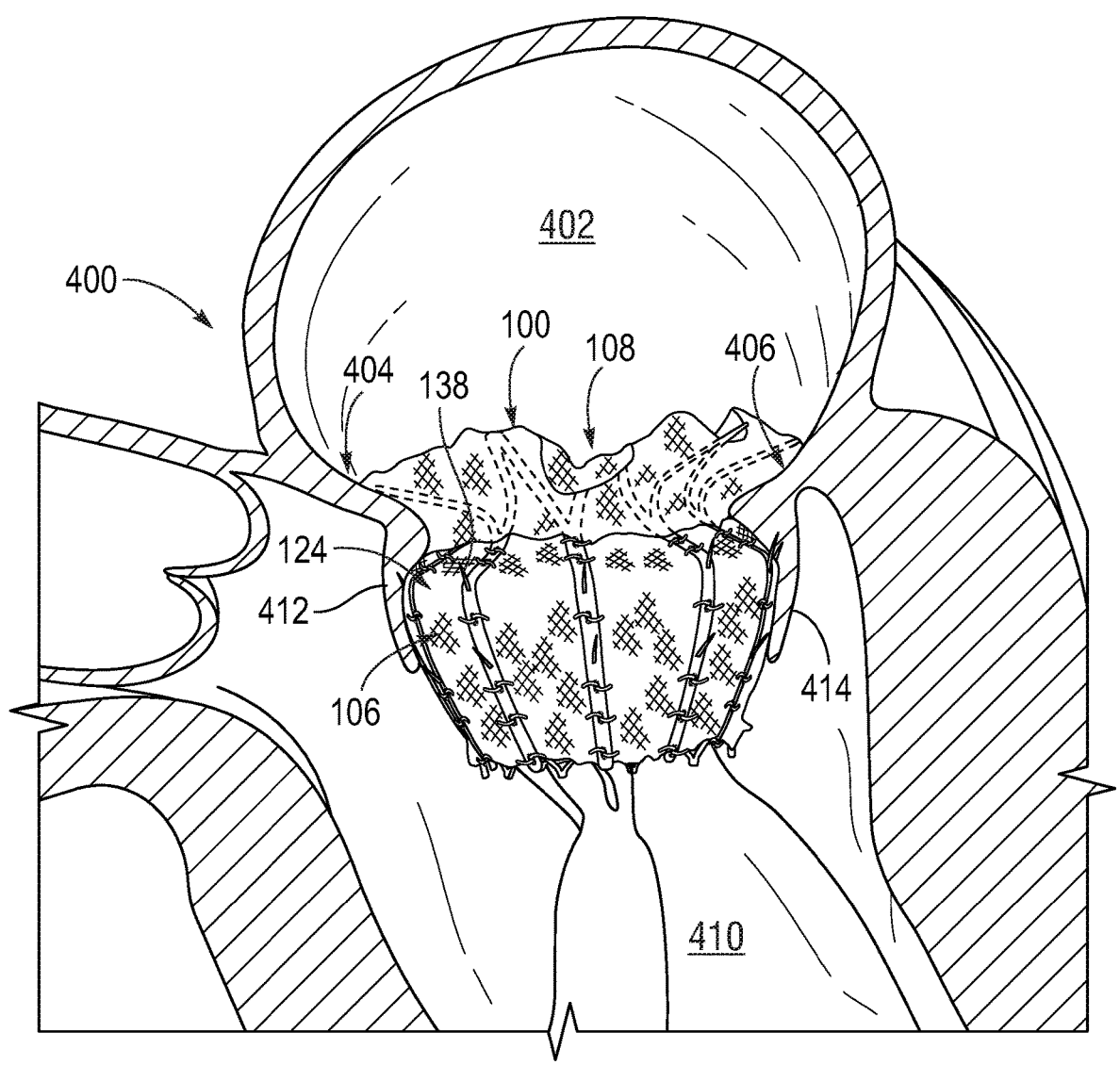
FIG. 27 is a cross-sectional view of the left atrium and the left ventricle illustrating the prosthetic valve of FIGS. 6-10 implanted in the mitral valve.

The prosthetic valve 100 can be implanted in the mitral valve using a trans-septal technique, which can comprise inserting a catheter into the right femoral vein, up the inferior vena cava and into the right atrium. The septum is then punctured and the catheter passed into the left atrium. Once located in the mitral valve, the prosthetic valve 100 can be expanded to its functional size to regulate the flow of blood from the left atrium into the left ventricle. FIG. 27 illustrates the prosthetic valve 100 implanted within a native mitral valve 400. The native mitral valve 400 can comprise an anterior leaflet 412 and a posterior leaflet 414 extending from a mitral valve annulus 406. The left atrium is illustrated at 402, and the left ventricle is illustrated at 410. The prosthetic valve 100 can be deployed in the mitral valve 400 such that the atrial portion 108 is located in the left atrium 402. In certain embodiments, the atrial portion 108 can contact the lower surface or floor 404 of the left atrium 402 around the mitral annulus 406 to provide stability.

Meanwhile, the ventricular portion 106 of the prosthetic valve can extend through the native mitral valve between the leaflets 412 and 414 such that the ventricular portion 106 is at least partially disposed in the left ventricle 410. In certain embodiments, the shoulder 124 of the ventricular portion 106 can be larger than the orifice of the mitral valve 400 such that the shoulder 124 engages the leaflets 412, 414 and/or the walls of the left ventricle 410 below the mitral valve. This can help to prevent the prosthetic valve 100 from becoming dislodged (e.g., into the left atrium 402) during ventricular systole. Additionally, the native leaflets 412 and 414 can lie against the exterior surface of the ventricular portion 106, and may be engaged by the tissue-engaging elements 138 to aid in retaining the prosthetic valve 100 in position. In certain embodiments, the external frame 118 can allow the prosthetic valve 100 to be implanted in the mitral valve annulus without separate fixation or anchoring devices.

FIGS. 28A, 28B, and 29 illustrate other embodiments of the outer frame 118. FIGS. 28A and 28B illustrate another configuration of the outer frame 118. In the embodiment of FIGS. 28A and 28B, the outer frame 118 comprises five rows of tissue-engaging members 138. The first end portions 122 of the struts 120 are also interconnected and spaced apart by U-shaped members 160. The members 160 originate from the first end portion 122 of a given strut 120, extend toward the second end portion 132 in a space or gap 162 between adjacent struts, curve around at an apex, and extend back to toward the first end portion 122 and connect to the adjacent strut 120. The gap 162 can be enclosed by atrial struts 130B and 130A of adjacent ventricular struts 120. When the frame 118 is expanded, the members 160 can extend or expand circumferentially between the struts 120 to interconnect the struts at the outflow end of the frame, as shown in FIG. 28C.

FIG. 29 illustrates another embodiment of an outer frame 170 that can be used in combination with the inner frame 16, or any of the other frames described herein. The frame 170 can comprise a plurality of first strut members configured as main struts or ventricular struts 172. The ventricular struts 172 can comprise first end portions 174 corresponding to the outflow end 14 of the assembled valve (see FIG. 7), and second end portions or junctions 176 offset from the first end portions toward the inflow end 102. The ventricular struts 172 can branch at a first junction 178 to form curved members 180 that extend toward the inflow end 102 before doubling back toward the outflow end 14 and connected to the junction 178 of an adjacent strut 172 to interconnect the struts 172. When expanded, the members 180 can interconnect adjacent ventricular struts 172, similar to the members 160 above. The struts 172 can divide or branch again at the junctions 176 to form atrial struts 182A and 182B. The atrial strut 182A of a given ventricular strut 172 can be coupled to the atrial strut 182B of an adjacent ventricular strut 172 to form apices 184, similar to the embodiments described above. In the illustrated configuration, the outer frame 170 does not include barbs or other tissue-engaging members, although in other embodiments the outer frame can include any number of tissue-engaging members arranged in any selected configuration.

Figure 30:
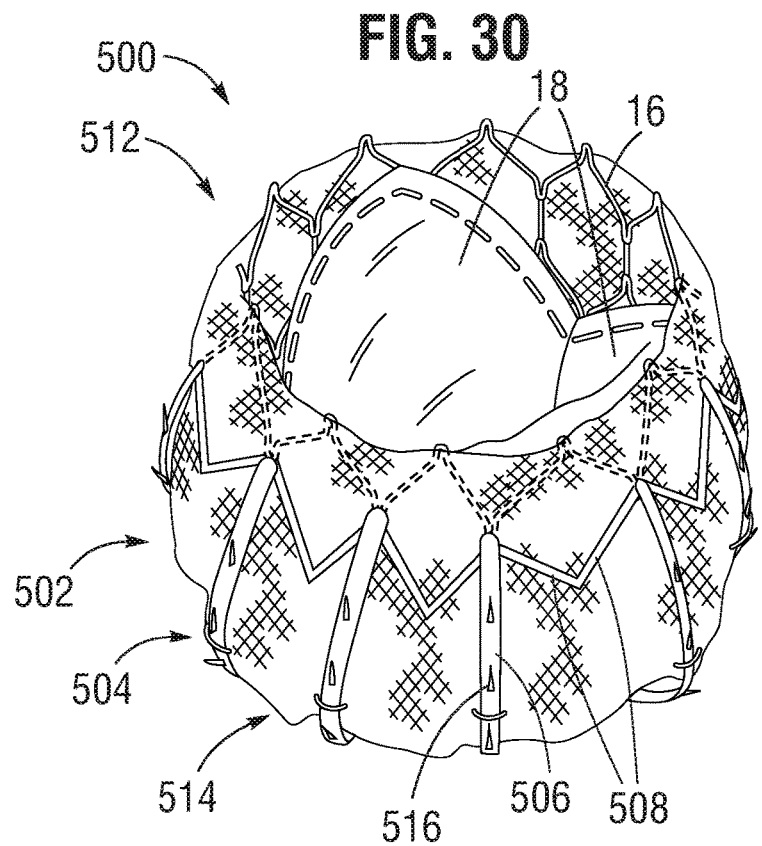
FIG. 30 is a perspective view of another embodiment of a prosthetic heart valve including an exterior frame without an atrial portion.
Figure 31A:
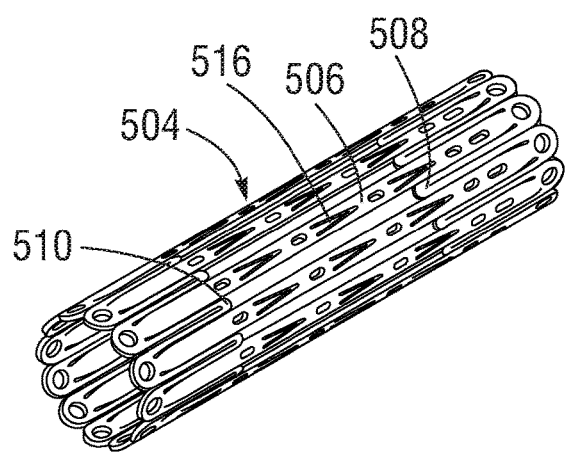
FIGS. 31A and 31B illustrate the external frame of valve of FIG. 30 in a collapsed configuration and a laid-flat configuration, respectively.
Figure 31B:
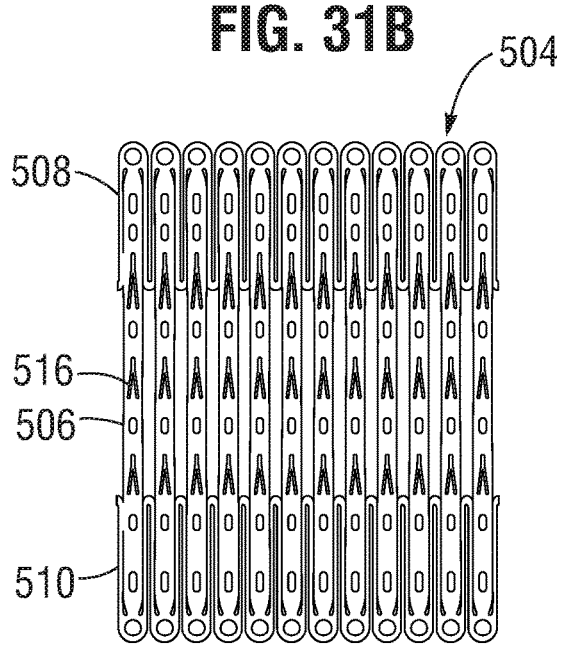

FIG. 30 illustrates another embodiment of a prosthetic heart valve 500 including a ventricular portion 502 similar to the prosthetic valve 100, but without an atrial portion. The prosthetic valve 500 can include an outer frame 504 situated about or around the outside of an inner frame configured as the frame 16 of FIGS. 3-5. The outer frame 504 can comprise a plurality of first strut members 506 extending longitudinally between an inflow end 512 and an outflow end 514. The strut members 506 can be interconnected at their inflow ends by circumferentially extending, zig-zagging second strut members 508, and at their outflow ends by similarly configured third struts 510. FIG. 31A illustrates the frame 504 in the radially collapsed configuration, and FIG. 31B illustrates the outer frame 504 in a laid-flat configuration for purposes of illustration. In the illustrated configuration, the outer frame 504 can comprise three rows of barbs 516, although the frame can include any number of rows of barbs, including no barbs. When implanted at the mitral valve, the prosthetic valve 500 can be located at least partially within the left ventricle. In certain embodiments, the diameter of the prosthetic valve 500 (e.g., of the outer frame 504 can be larger than the orifice of the mitral valve such that the frame 504 engages the leaflets and/or the walls of the left ventricle below the mitral valve to keep the prosthetic valve in place. The native leaflets of the mitral valve may also lie against the exterior surface of the ventricular portion 502, and may be engaged by the barbs 516.

Figure 32:
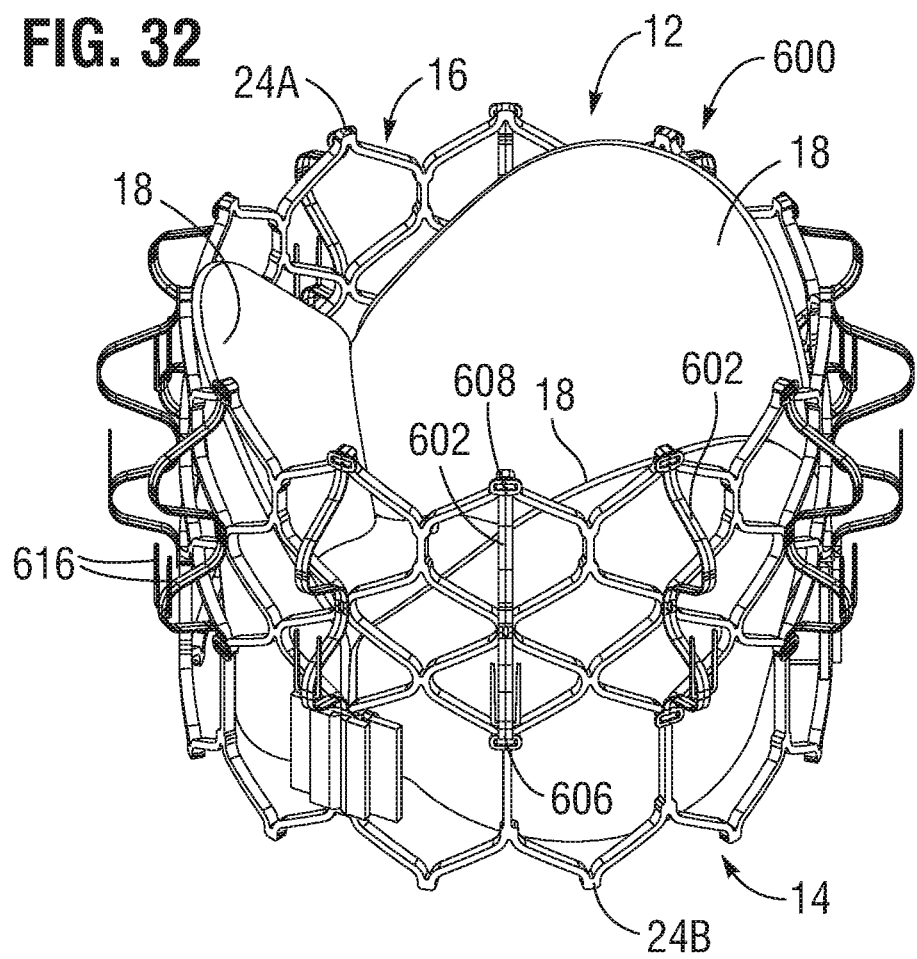
FIG. 32 is a perspective view of another embodiment of a prosthetic heart valve including an inner frame and a plurality of strut members coupled to the inner frame.
Figure 33:
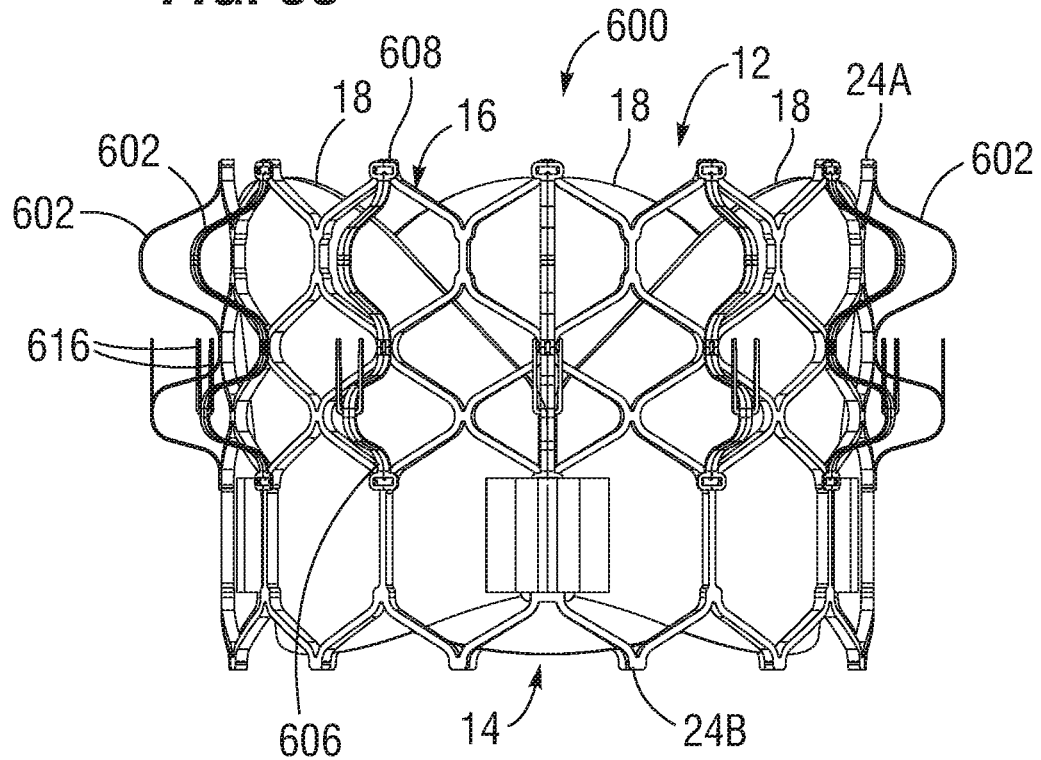
FIG. 33 is a side elevation view of the prosthetic heart valve of FIG. 32.
Figure 34:
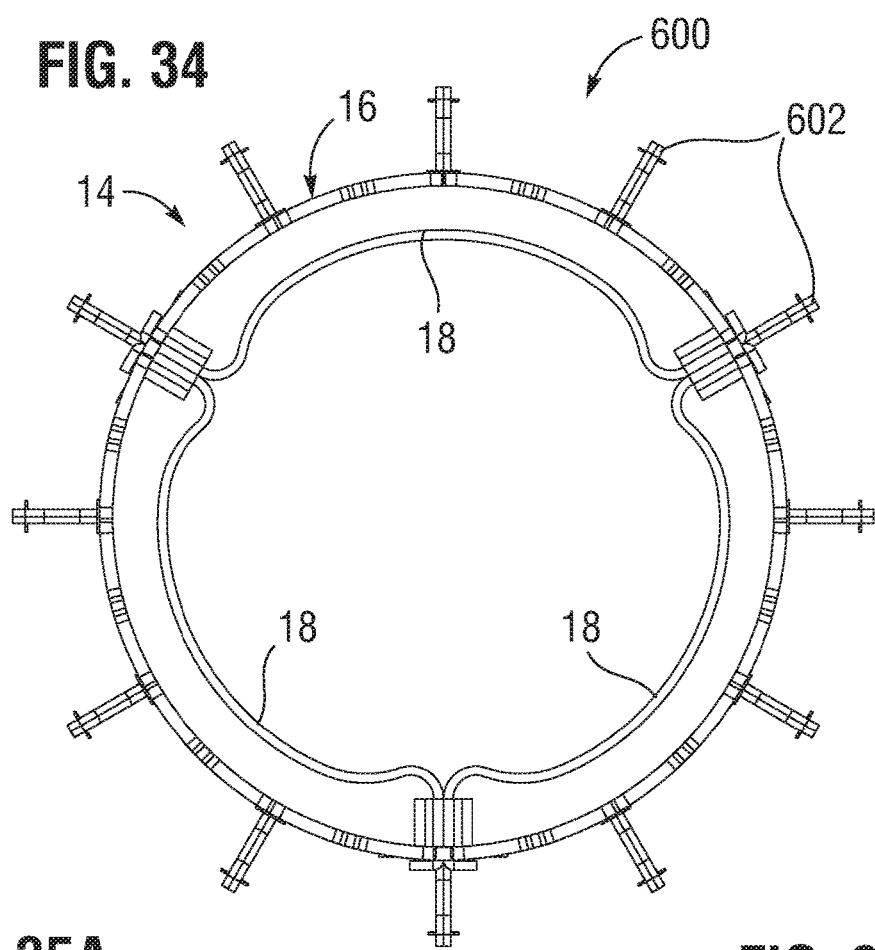
FIG. 34 is a bottom plan view illustrating the outflow end of the prosthetic heart valve of FIG. 32.
Figure 35A:
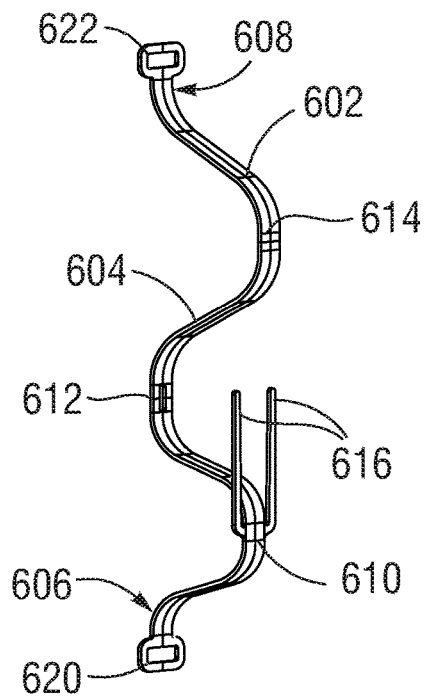
FIG. 35A is a perspective view of a representative exterior strut member of the prosthetic heart valve of FIG. 32, according to one embodiment.
Figure 35B:
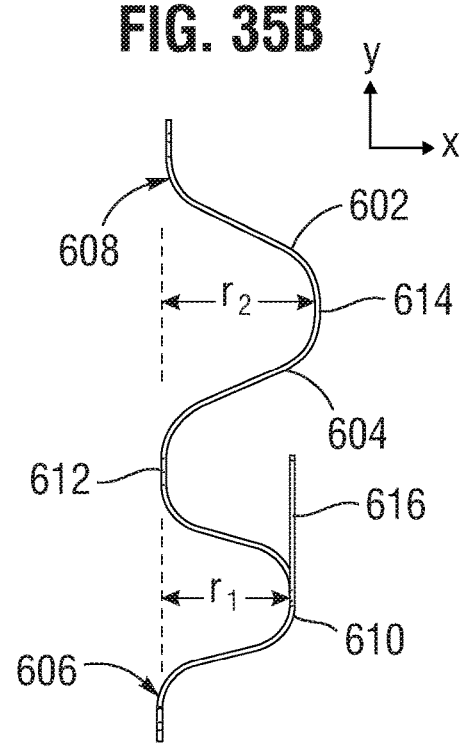
FIG. 35B is a side elevation view of the exterior strut member of FIG. 35A.

FIGS. 32-34 illustrate another embodiment of a prosthetic heart valve 600 including an inner frame configured as the frame 16 of FIG. 3. The prosthetic valve 600 is shown configured for implantation in the mitral valve, but can also be configured for implantation in other heart valve such as the aortic valve. The inflow end 12 of the inner frame 16 is shown at the top of the figure in FIGS. 32 and 33, and FIG. 34 illustrates a plan view of the prosthetic heart valve looking toward the outflow end 14. The prosthetic valve 600 can further comprise a plurality of strut members 602 disposed around the exterior of the frame 16. With reference to FIGS. 35A and 35B, each of the strut members 602 can comprise a main body 604 having a first end portion 606 and a second end portion 608. The main body 604 can have a repeatedly curving or undulating shape in the manner of a sine wave. For example, beginning from the first end portion 606 and moving in a direction along the positive y-axis, the main body 604 can comprise a first apex or crest 610 located radially outward of the first end portion 606 (e.g., spaced from the first end portion 606 along the positive x-axis). Continuing in the positive y-direction, the main body 604 can then curve radially inwardly toward a second apex or trough 612, then radially outward to a third apex configured as a crest 614, and then radially inward to the second end portion 608. In the illustrated embodiment, the strut members 602 can comprise a pair of tissue-engaging members configured as barbs or tines 616 coupled to the crest 610 and extending along the positive y-axis in the direction of the inflow end of the prosthetic valve 600.

Referring to FIGS. 32 and 33, the first end portions 606 of the strut members 602 can be coupled to the fourth row IV of struts 22 of the inner frame 16 (see FIG. 5), and the second end portions 608 can be coupled to the first rung I of struts 22 at, for example, the inflow apices 24A. The tissue-engaging members 616 of the struts 602 can extend in the positive y-direction (e.g., in the proximal or upstream direction) to engage the surrounding tissue when the prosthetic valve is implanted. Referring to FIG. 35A, the first end portions 606 can define openings 620, and the second end portions 608 can define openings 622. In certain embodiments, the struts 602 can be coupled to the frame 16 by sutures, loops, fasteners, or other securing means extending through the openings 620 and 622. The struts 602 can also be coupled to the frame 16 by adhesive, or heat bonding such as by welding. In yet other embodiments, the struts 602 can be integrally formed with the frame 16. As used herein, the terms "unitary construction" and "integrally formed" refer to a construction that does not include any stitches, sutures, welds or bonds, fasteners, or other means for securing separately formed pieces of material to each other.

Referring again to FIG. 35B, the trough-to-peak radial distance $r_1$ between the trough 612 and the crest 610, and the trough-to-peak radial distance $r_2$ between the trough 612 and the crest 614, can each be configured such that when the prosthetic valve 600 is crimped to the collapsed configuration, the main body 604 of each strut straightens and lengthens along with the frame 16 and lies flat against the exterior of the frame 16. When the prosthetic valve 600 is expanded to its functional size, each of the struts 602 can assume the undulating shape illustrated in FIGS. 32-35.

The struts 602 can be formed from any of various self-expandable materials such as Nitinol, or plastically-expandable materials such as stainless steel or cobalt chromium alloys. In other embodiments, the struts 602 can comprise polymeric materials. In certain embodiments, the struts 602 can be shape-set into the configuration shown in FIGS. 32-35B.

In other embodiments, the struts 602 can extend between any two rows of struts of the inner frame 16, and can comprise any number of crests and troughs, including a single crest (e.g., such that the struts 602 are bow-shaped), or more than two crests. The struts 602 also need not be coupled to each apex 24A of the inner frame 16, but can be coupled to every other apex 24A, or to select apices 24A with a selected angular spacing (e.g., three struts 602 circumferentially spaced apart around the frame 16 by 120°). In yet other embodiments, different configurations of struts 602 of having varying shapes and/or lengths can be coupled to the frame 16, depending upon the particular application.

When implanted in the native mitral valve, the prosthetic valve 600 can be disposed at least partially in the left ventricle. The struts 602 and/or the barbs 616 can engage the surrounding tissue and hold the prosthetic valve in place. In certain embodiments, the prosthetic valve can be positioned in the mitral annulus such that the mitral annulus is received in the troughs defined by the second apices 612 of the struts 602. In this manner, the tissue of the annulus and/or the mitral valve leaflets can be received or engaged between the apices 610 and 614, and/or engaged by the barbs 616.

Figure 38:
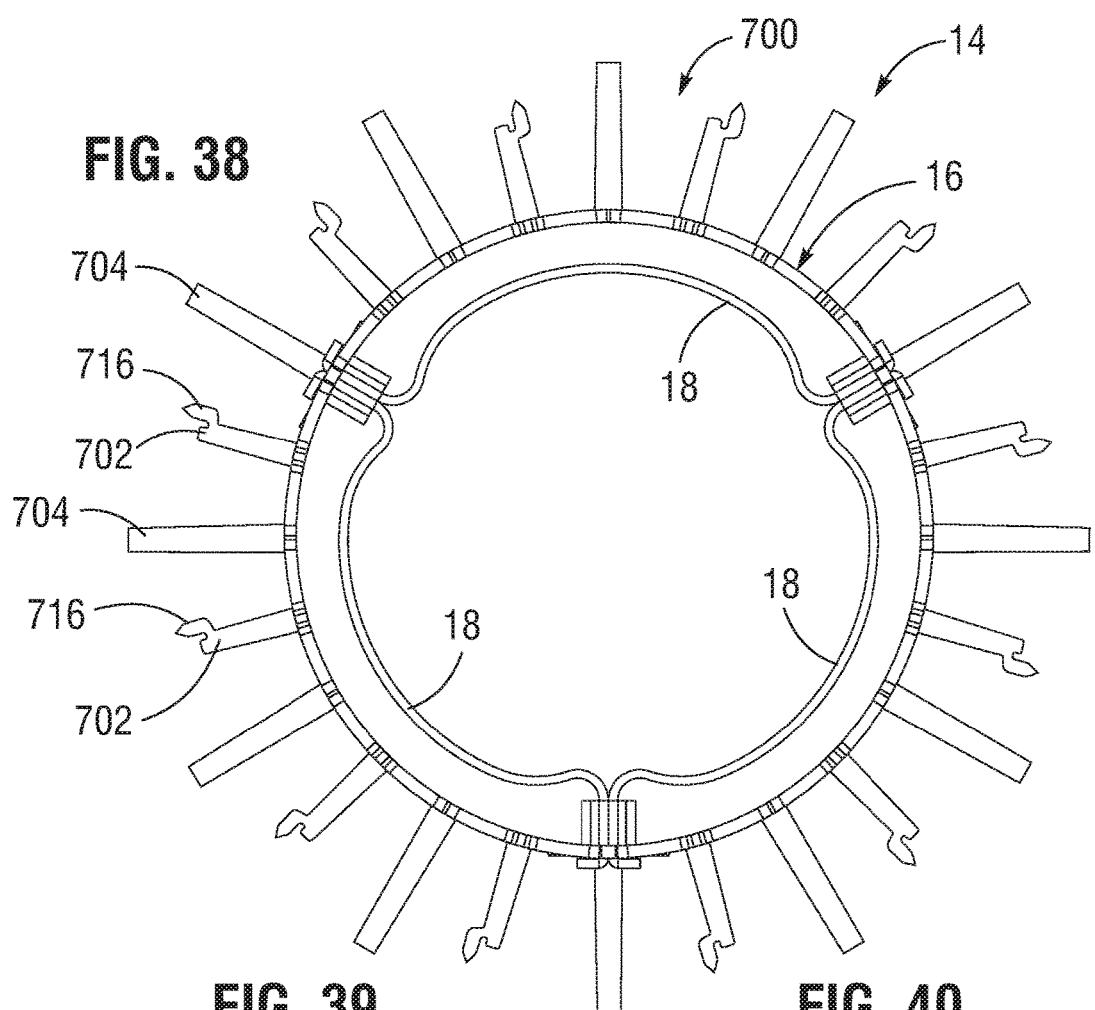
FIG. 38 is a bottom plan view illustrating the outflow end of the prosthetic heart valve of FIG. 36.
Figure 39:
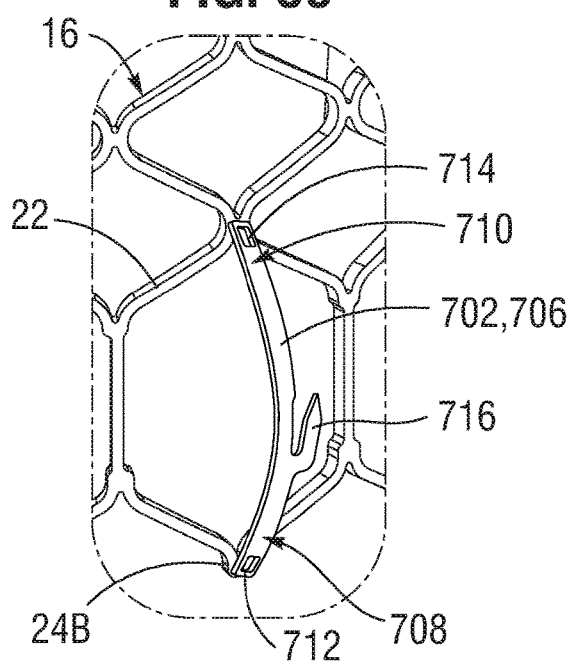
FIG. 39 is a magnified perspective view of a portion of the prosthetic heart valve of FIG. 36 illustrating an exterior strut member according to a first embodiment.

FIGS. 36-38 illustrate another embodiment of a prosthetic heart valve 700 including an inner frame configured as the frame 16 of FIG. 3, and including the leaflets 18. The prosthetic valve 700 can further comprise a plurality of first strut members 702 disposed around the exterior of the frame 16 adjacent or closer to the outflow end 14 of the frame 16, and a plurality of second strut members 704 disposed around the exterior of the frame 16 adjacent or closer to the inflow end 12 of the frame 16. FIG. 39 illustrates the first strut members 702 in greater detail. The strut members 702 can comprise a main body 706 having a first or outflow end portion 708 and a second or inflow end portion 710. The first end portion 708 can comprise an opening 712, and the second end portion 710 can comprise an opening 714. The openings 712 and 714 can facilitate attachment of the strut members 702 to the frame 16 by, for example, suturing. The first struts 702 can comprise a tissue-engaging member configured as a barb 716 coupled to the main body 706 and offset circumferentially from the main body. In certain embodiments, the main bodies of the struts 702 can comprise a reduced width portion adjacent the barbs 716, which can facilitate bending of the struts 702 at the reduced width portion. In the illustrated embodiment, the first strut members 702 can extend from the outflow apices 24B of the fifth row V of struts 22 (FIG. 5) of the frame 16 to the junction between the third rung III and the fourth rung IV of struts 22. The struts 702 can have a length configured such that when the prosthetic valve 700 is in the expanded configuration, the struts 702 bow outwardly from the frame 16 as shown, and can lie flat against the frame 16 when the prosthetic valve is in the collapsed configuration. As the struts 702 curve outwardly from the frame 16, the barbs 716 can form an angle with the struts 702, and can extend outwardly or away from the struts 702. In other embodiments, the barbs 716 can be received in openings defined in the main bodies of the struts 702, and can extend outwardly from the struts (e.g., in the proximal direction) when the frame is expanded, similar to the barbs 138 described above.

Figure 40:
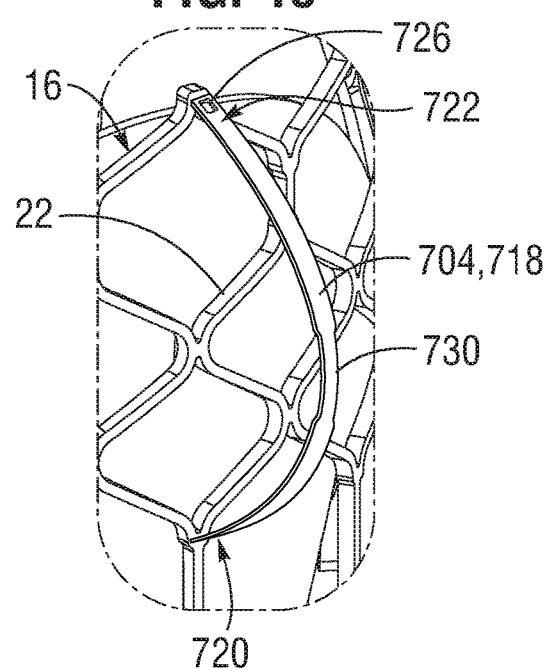
FIG. 40 is a magnified perspective view of a portion of the prosthetic heart valve of FIG. 36 illustrating an exterior strut member according to a second embodiment.

Referring to FIG. 40, each second strut member 704 can comprise a main body 718 having a first end portion 720 and a second end portion 722. The first and second end portions 720 and 722 can comprise respective openings 724 (FIG. 37) and 726 for attachment to the frame 16, similar to the first struts 702 described above. In the illustrated embodiment, the second strut members 704 can extend between the fourth rung IV of struts 22 of the frame 16 and the inflow apices 24A of the first rung I struts (FIG. 5) of the frame 16 such that that the struts 702 and 704 are spaced apart in the axial direction but at least partially overlap in the axial direction. The second struts 704 can have a length configured such that when the prosthetic valve 700 is in the expanded configuration, the struts 704 bow outwardly from the frame 16 as shown, and lie flat against the frame 16 when the prosthetic valve is in the collapsed configuration. The second struts 704 can also comprise a central portion 730 with a reduced width dimension. In certain embodiments, the struts 704 can be induced to bend about the central portion 730 such that the central portion 730 defines an apex of the curved struts in the expanded configuration, as shown in FIG. 37. In other embodiments, the reduced width portion can be located elsewhere along the length of the strut 704 in order to induce flexing about other points. In yet other embodiments, the struts 704 can also comprise tissue-engaging members, such as any of the tissue-engaging member embodiments described herein. In other embodiments, the struts 702 and 704 need not overlap in the axial direction.

In the illustrated embodiment, the first struts 702 and the second struts 704 can be arranged alternatingly around the circumference of the frame 16 such that, moving in a circumferential direction around the frame 16, each strut member 702 is disposed between two struts 704 and vice versa. Stated differently, the first struts 702 (also referred to as second strut members) are circumferentially offset from the second struts 704 (also referred to as third strut members). In other embodiments, the struts 702 and 704 can be arranged in any pattern, and can have any length. The struts 702 and 704 can also extend between any two rows of struts I-V of the inner frame 16. Certain embodiments may also include more first struts 702 than second struts 704, or vice versa, with any angular spacing, depending upon the particular application.

The struts 702 and 704 can comprise any biocompatible self-expandable or plastically expandable materials, as described above. In certain embodiments, the struts 702 and/or 704 can be sutured to the frame 16, but may also be adhered, welded, etc., or any combination thereof. The struts 702 and/or the struts 704 may also be integrally formed with the frame 16.

When implanted in the mitral valve, the prosthetic valve 700 can be positioned such that the mitral annulus is disposed at about the level of the fourth row IV of struts of the inner frame 16 (see FIG. 5). In other words, the mitral annulus can be disposed between, and/or engaged by, the second end portions 710 of the struts 702 and the first end portions 720 of the struts 704. The barbs 716 can also engage the native leaflets of the mitral valve (e.g., the ventricular surfaces of the leaflets) and/or the surrounding tissue of the valve annulus to hold the prosthetic valve 700 in place.

FIGS. 41-46B illustrate another embodiment of a prosthetic heart valve 800 including the frame 16 of FIG. 3 and the leaflets 18. In the illustrated embodiment, the prosthetic heart valve 800 is configured for implantation in the native aortic valve (e.g., to treat aortic insufficiency), but can be implanted within the other native heart valves in other embodiments. Thus, with reference to FIG. 41, the prosthetic valve 800 is shown in an orientation suitable for implantation in the aortic valve in which the lower portion of the prosthetic valve 800 in the figure is configured as the inflow end 818 and the upper portion of the valve is configured as the outflow end 820.

Figure 46A:
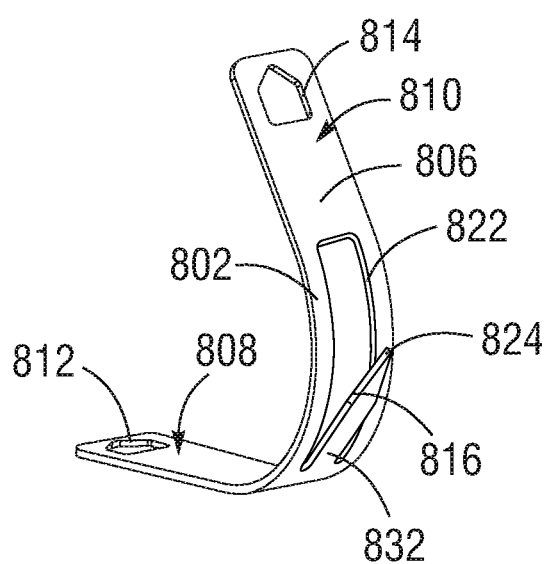
FIG. 46A is a perspective view of an exterior strut member of the prosthetic heart valve of FIG. 41, according to one embodiment.
Figure 46B:
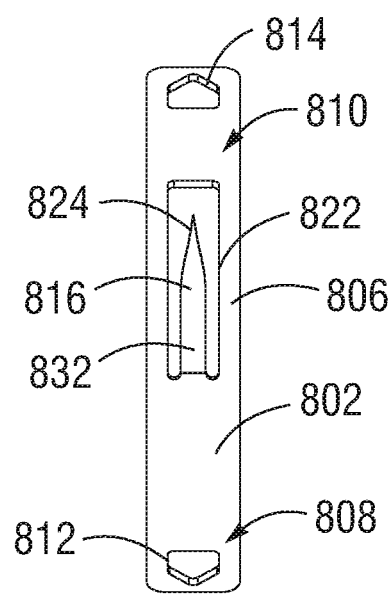
FIG. 46B is a front elevation view of the exterior strut member of FIG. 46A.

The prosthetic valve 800 can further comprise a plurality of first strut members 802 and a plurality of second strut members 804 disposed around and coupled to the exterior of the frame 16. FIGS. 46A and 46B illustrate a representative embodiment of a first strut member 802 in greater detail. The strut member 802 can comprise a main body 806 having a first end portion 808 and a second end portion 810. The first end portion 808 can comprise an opening 812, and the second end portion 810 can comprise an opening 814. The openings 812 and 814 can facilitate attachment of the strut members 802 to the frame 16 by, for example, suturing. The first strut 802 can also comprise a tissue-engaging member 816 having a base portion 832 coupled to the main body 806 and a sharp or pointed free end portion 824. In the illustrated embodiment, the base portion 832 of the tissue-engaging member 816 is coupled to the main body 806 in an opening 822 defined in the main body. The tissue-engaging member 816 is configured such that the pointed free end portion 824 extends radially outwardly from the opening 822, and is angled in the direction of the outflow end 820 of the prosthetic valve when the prosthetic valve is in the expanded configuration.

Figure 43:
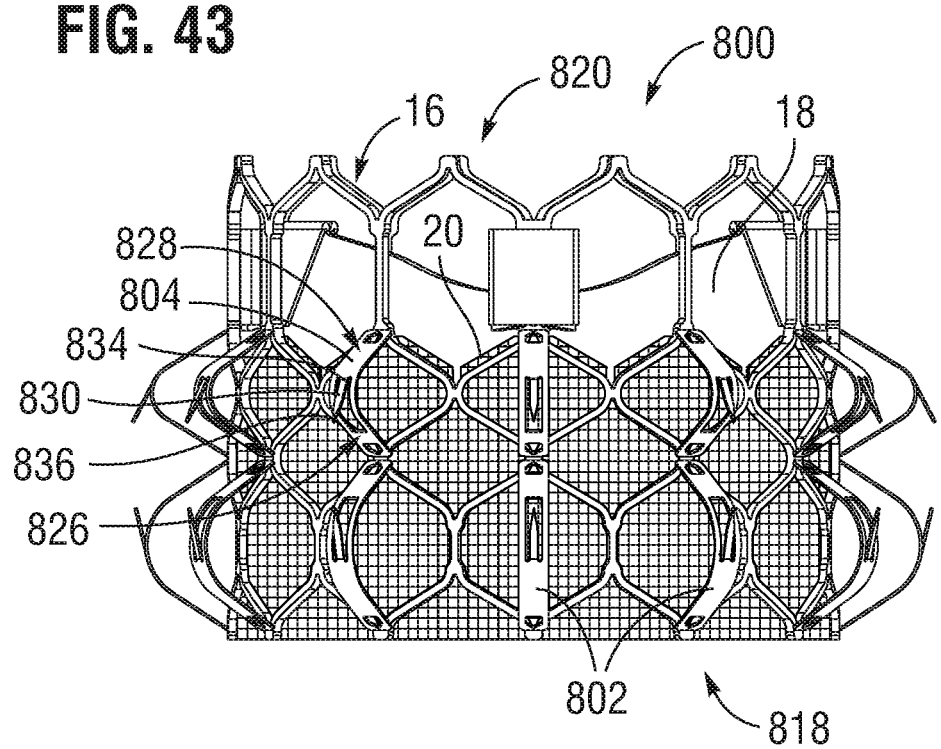
FIG. 43 is a side elevation view of the prosthetic heart valve of FIG. 41 with the sealing members removed for purposes of illustration.
Figure 44:
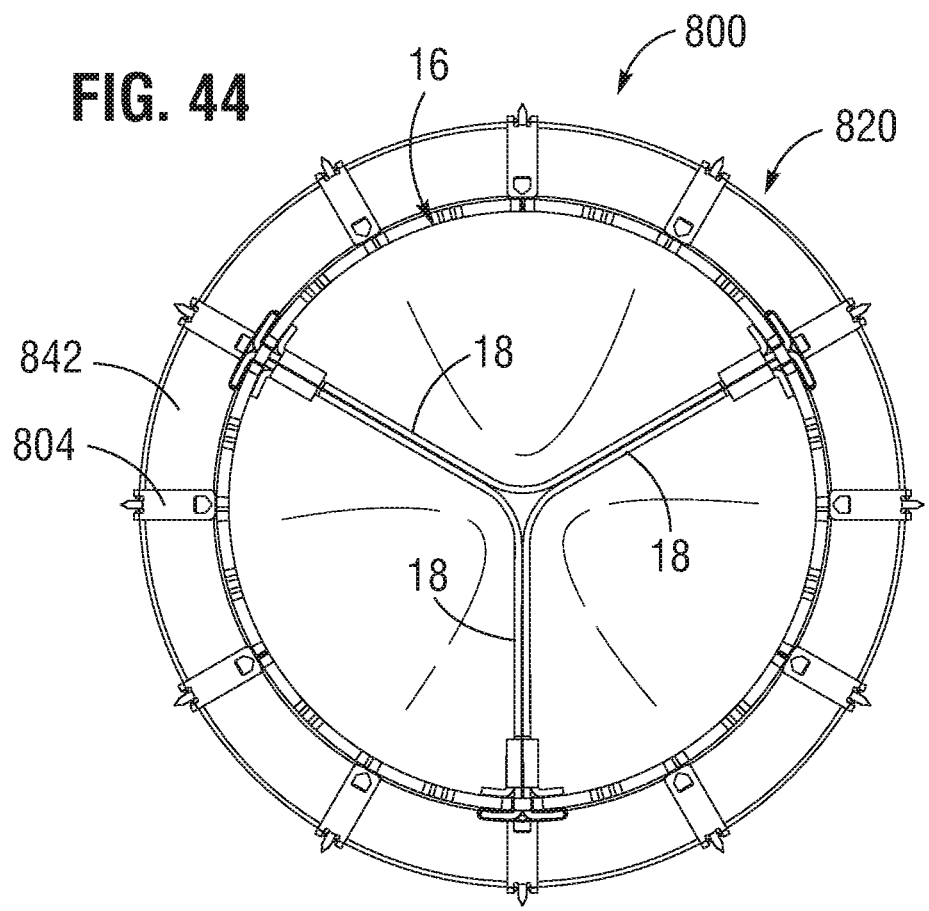
FIG. 44 is a top plan view of the outflow end of the prosthetic heart valve of FIG. 41.
Figure 45:
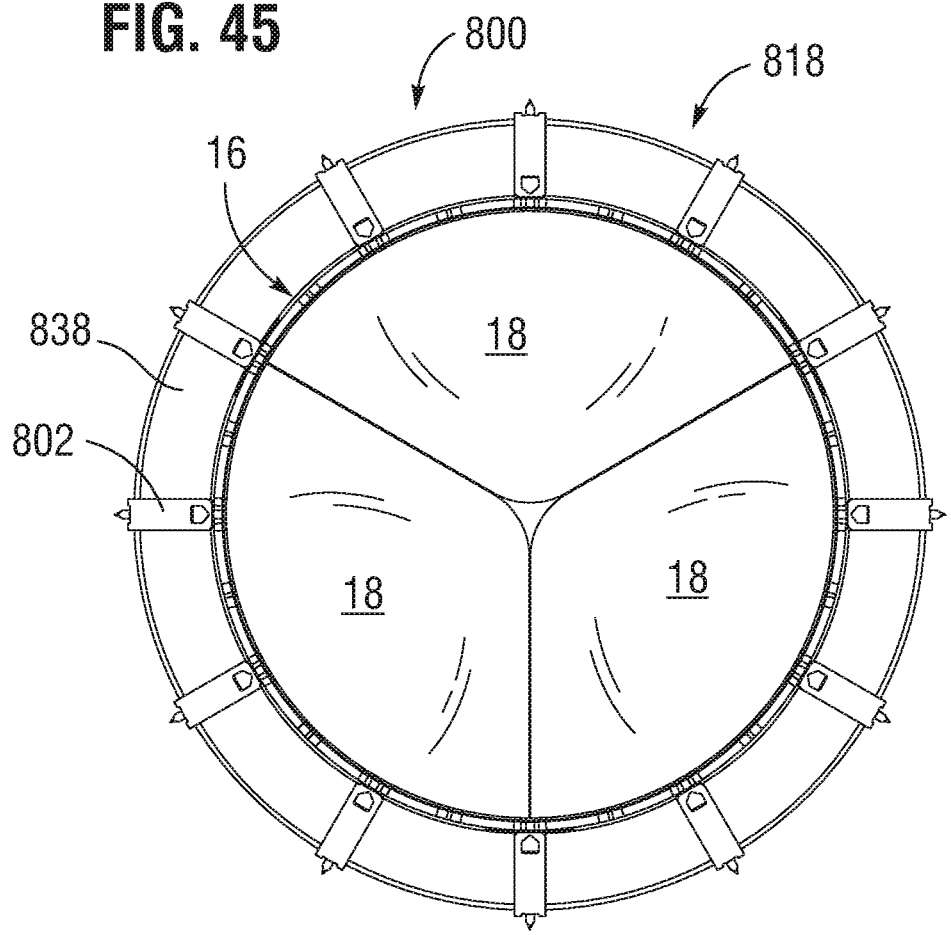
FIG. 45 is a bottom plan view of the inflow end prosthetic heart valve of FIG. 41.

The second struts 804 can be configured similarly to the first struts 802, and can include first end portions 826, second end portions 828, and tissue-engaging members 830 (see FIG. 43). The tissue-engaging members 830 can comprise base portions 834 coupled to the struts 804 and free end portions 836, and can extend radially outwardly from the struts 804 in the direction of the inflow end 818 of the prosthetic valve when the prosthetic valve is in the expanded configuration.

In the illustrated embodiment, the first strut members 802 can extend between the first row I (FIG. 5) of struts 22 of the frame 16 and the second row II of struts 22 (e.g., the junction between the second row II and the third row III). The struts 804 can extend between the second row II of struts 22 (FIG. 5) (e.g., the junction between the second row II and the third row III) of the frame 16 and the fourth rung IV of struts 22. The struts 802 and the struts 804 can have respective lengths configured such that when the prosthetic valve 800 is in the expanded configuration, the struts 802 and the struts 804 bow radially outwardly from the frame 16. In the expanded state, the tissue-engaging members 816 can extend radially away from the struts 802 in a direction toward the outflow end 820, and at an angle to the struts 802. The tissue-engaging members 830 of the struts 804 can extend radially away from the struts 804 in a direction toward the inflow end 818, and at an angle to the struts 804. The struts 802 and 804 can be coupled to the frame 16 by, for example, sutures extending through the respective openings in the end portions of the struts, or by any other attachment method.

FIGS. 47A-47C illustrate expansion of the prosthetic valve 800 from the collapsed configuration in FIG. 47A, through a partially expanded state in FIG. 47B, to a fully expanded state in FIG. 47C. As shown in FIG. 47A, the struts 802 and the struts 804 can be configured to lie flat against the frame 16 when the prosthetic valve 800 is in the collapsed configuration. In the expanded configuration, the struts 802 and 804 can be configured to expand into the Valsava sinuses of the aortic root to prevent the prosthetic valve from becoming dislodged during valve operation. The tissue-engaging members 816 and 830 can also engage the tissue of the aortic root. By expanding into the aortic root and engaging the surrounding tissue, the struts 802 and 804 can be especially advantageous in treating aortic insufficiency in patients where there is not significant calcification of the native aortic valve against which to anchor a traditional transcatheter heart valve, and/or patients in which the aortic root is dilated.

In the illustrated embodiment, the first struts 802 and the second struts 804 can be paired with each other at the same circumferential location on the frame 16 (e.g., aligned with the outflow apices of the frame 16). In other words, the second end portions 810 of the first struts 802 and the first end portions 826 of the second struts 804 can be aligned with each other, and can be coupled to the frame 16 at the same circumferential location on the frame 16. In other embodiments, the struts 802 and the struts 804 can be circumferentially offset from each other around the frame 16, and/or the number of struts 802 may differ from the number of struts 804, depending upon the particular characteristics desired.

Figure 41:
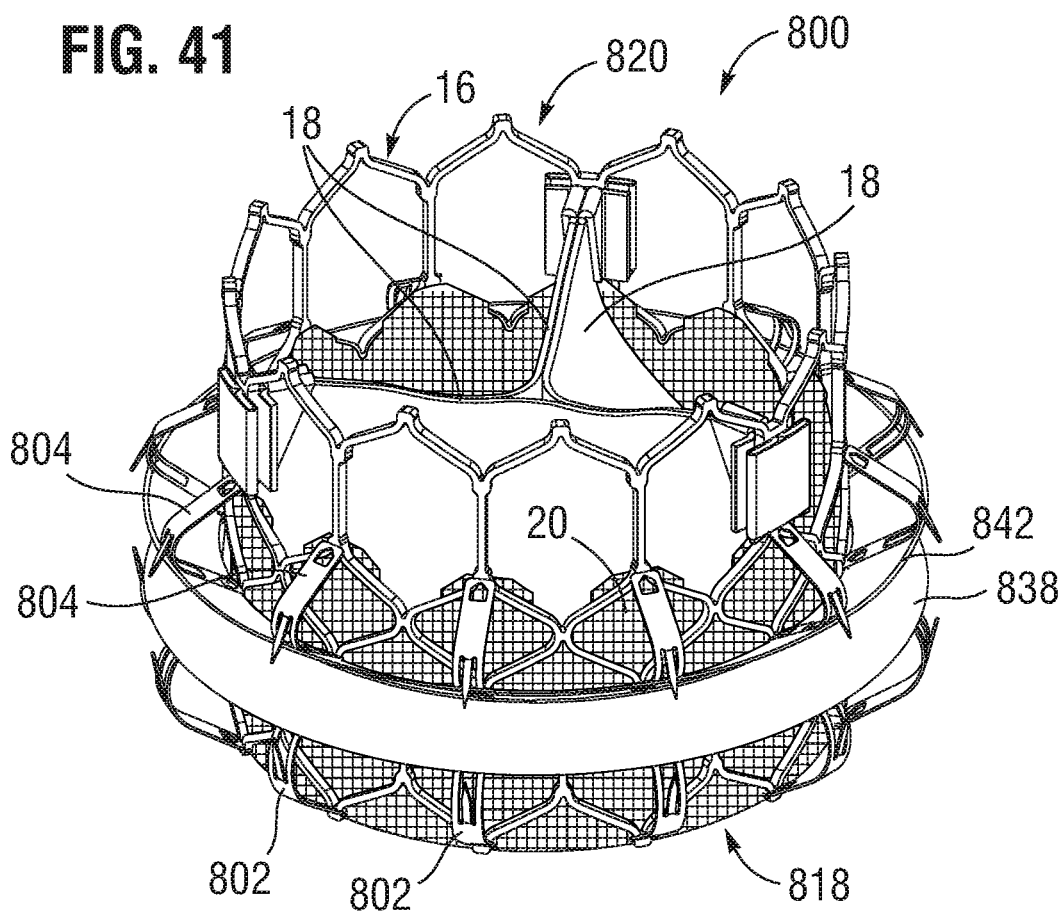
FIG. 41 is a perspective view of another embodiment of a prosthetic heart valve including an inner frame and a plurality of external strut members coupled to the inner frame, and sealing members coupled to the external strut members.
Figure 42:
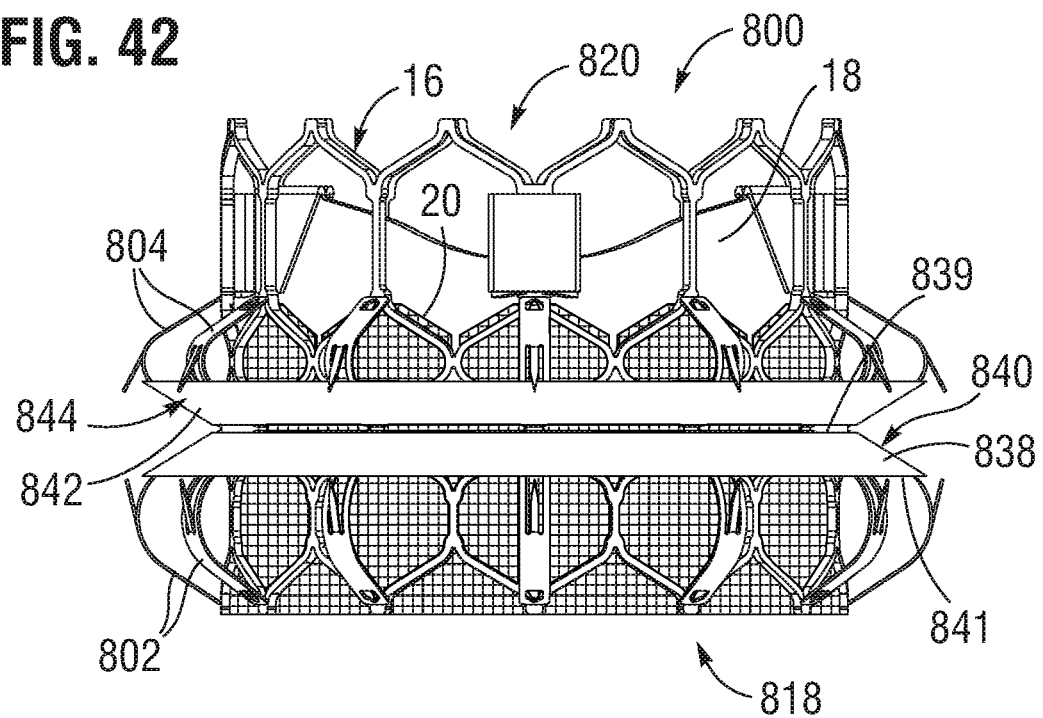
FIG. 42 is a side elevation view of the prosthetic heart valve of FIG. 41.

Referring to FIGS. 41 and 42, the prosthetic valve 800 can include a first annular skirt member 838 disposed around the frame 16 and coupled to the first struts 802. With reference to FIG. 42, in some embodiments the skirt 838 can be disposed on and/or coupled to the exterior surfaces of the struts 802 between, for example, the second end portions 810 and the bases 832 (FIGS. 46A and 46B) of the tissue-engaging members 816. In this manner, the skirt 838 can extend radially outward from the frame 16 and at an angle to the frame 16 such that an outer surface 840 of the skirt 838 is oriented proximally or in the downstream direction toward the outflow end 820 of the prosthetic valve when the prosthetic valve is in the expanded configuration. For example, in some embodiments the skirt 838 can be oriented at an angle of 30° to 60°, 40° to 50°, or 45° relative to the exterior surface of the frame 16. When the frame is in the expanded configuration, a first circumferential edge 839 of the skirt 838 can be disposed against or adjacent the exterior of the frame 16, and a second circumferential edge 841 can be disposed radially outward of the circumferential edge 839 (e.g., adjacent the apices of the struts 802).

The prosthetic valve can further include a second annular skirt member 842 disposed around the frame 16 and coupled to the second struts 804. The second skirt 842 can be disposed on and/or coupled to the exterior surfaces of the struts 804 between the bases 834 (FIG. 43) of the tissue-engaging members 830 and the first end portions 826 of the second struts 804. The skirt 842 can extend radially outward from the frame 16 and at an angle to the frame 16 such that an outer surface 844 of the skirt 842 is oriented distally or in the upstream direction toward the inflow end 818 of the prosthetic valve in the expanded configuration, and angled toward the surface 840 of the skirt 838. For example, the skirt 842 can be oriented at substantially the same angle to the frame 16 as the skirt 838, but in the opposite direction toward the inflow end 818. The skirts 838 and 842 can help to seal against the surrounding tissue to reduce or prevent perivalvular leakage around the prosthetic valve. In other embodiments, the skirt 838 and/or the skirt 842 can extend over or cover the apices of the respective struts 802 and 804. In yet other embodiments, the prosthetic heart valve 800 can comprise a sealing member such as a skirt that covers both sets of struts 802 and 804, and which can be urged outwardly into a curved shape by the struts when the frame is expanded.

In the illustrated embodiment, the skirts 838 and 842 can be configured as strips of material. The skirts 838 and 842 can comprise a woven fabric, a non-woven fabric such as a knitted fabric or felt material, and/or a polymeric film or substrate. In some embodiments, the skirt 838 can be configured different from the skirt 842, and/or can comprise different materials. The skirts may also be different sizes and/or shapes, depending upon the particular requirements of the system. A single sealing member can also be positioned between the struts 802 and 804 and attached to the struts 802, 804 such that the sealing member folds about its circumferential midline as the struts 802 and 804 move into the curved shape.

Figures 48, 49:
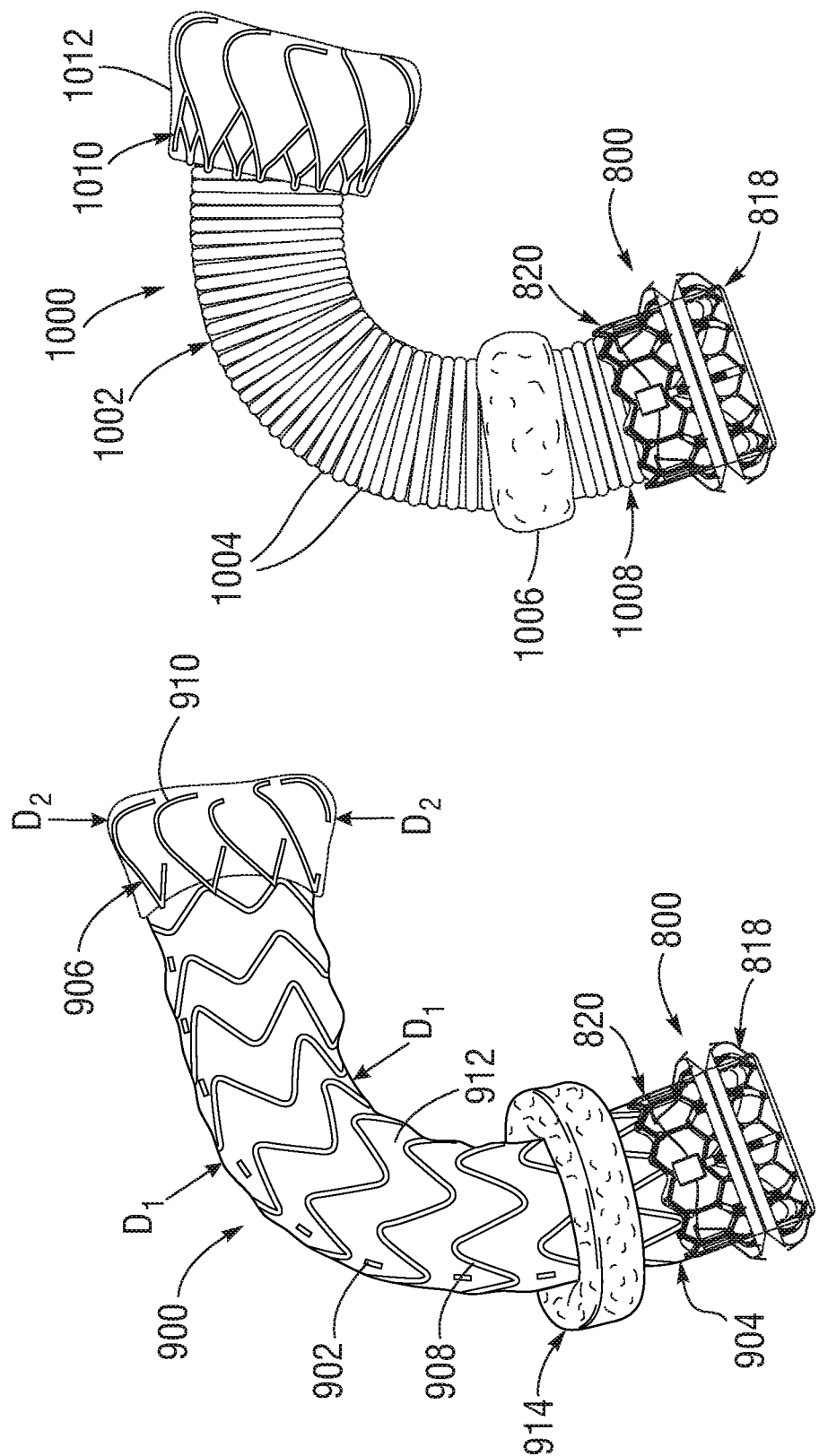
FIG. 48 is a perspective view of a prosthetic implant including the prosthetic heart valve of FIG. 41 and a conduit, according to one embodiment.
FIG. 49 is a perspective view of a prosthetic implant including the prosthetic heart valve of FIG. 41 and a conduit, according to another embodiment

In some embodiments, the prosthetic valve embodiments described herein can be used in combination with any of a variety of conduits or conduit grafts, such as endovascular grafts, stent grafts, etc., for example, to repair a blood vessel downstream of the prosthetic valve. A representative embodiment of a prosthetic device comprising a prosthetic valve 800 and a conduit 900 is illustrated in FIG. 48. In particular embodiments, the prosthetic valve 800 is configured to be implanted within or adjacent the native aortic valve and the conduit 900 is configured to be implanted in the ascending aorta.

The conduit 900 can comprise a tubular main body 902 having a first (e.g., inflow) end portion 904 and a second (e.g., outflow) end portion 906. In the embodiment of FIG. 48, the main body 902 can comprise a stent frame 908 and a tubular textile covering 912. In certain embodiments, the stent frame and, thus, the main body 902, can be movable between a collapsed delivery configuration and an expanded functional configuration. In the expanded state, the main body 902 can have a diameter $D_1$. The second end portion 906 can comprise a stent frame 910, which can have a diameter $D_2$ that is larger than the diameter $D_1$ of the main body 902 when the conduit is in the expanded state to aid in anchoring the conduit in a blood vessel, as further described below.

The first end portion 904 can be configured to interface with the outflow end 820 of the prosthetic valve 800 such that the prosthetic valve and the conduit are in fluid communication with one another. For example, in certain embodiments, the outflow end 820 of the prosthetic valve 800 can be coupled to the first end portion 904 of the conduit 900 by, for example, suturing, loops or extension portions extending through the struts of the prosthetic valve 800, by any of various mechanical couplings such as locking rings, or by any other coupling means. In certain embodiments, the prosthetic valve 800 can be at least partially received within the lumen of the conduit 900. The conduit 900 can comprise a sealing feature or sealing member generally indicated at 914. The sealing feature 914 can be disposed circumferentially around the main body 902, although only a portion of the sealing feature 914 is shown in FIG. 48. In certain embodiments, the sealing member 914 can be positioned downstream of the prosthetic valve 800. The sealing feature 914 can be configured to form a seal with the walls of a vessel into which the conduit 900 is implanted (e.g., the aortic root or the ascending aorta). The sealing feature 914 can comprise, for example, voluminous fabrics such as velour, one or more fabric skirts, a stent or frame (e.g., comprising a fabric covering), or combinations thereof.

FIG. 49 illustrates another embodiment of a conduit 1000 that can be used in combination with the prosthetic valves described herein, such as the prosthetic valve 800. The main body 1002 can comprise corrugations or ridges 1004 that increase the flexibility of the conduit and allow the conduit to increase or decrease in length. The conduit 1000 can also comprise a sealing feature 1006 at or near the inflow end 1008 of the conduit. The sealing feature 1006 can be configured similarly to any of the sealing features described above with reference to FIG. 48. The outflow end 1010 of the conduit can also comprise a frame or portion 1012 having a diameter greater than the diameter of the main body of the conduit to facilitate anchoring the outflow end 1010 in a body lumen. In certain embodiments, the outflow portion 1010 can comprise a sealing feature similar to the seal 1006 in place of, or in addition to, the frame 1012.

Figure 50:
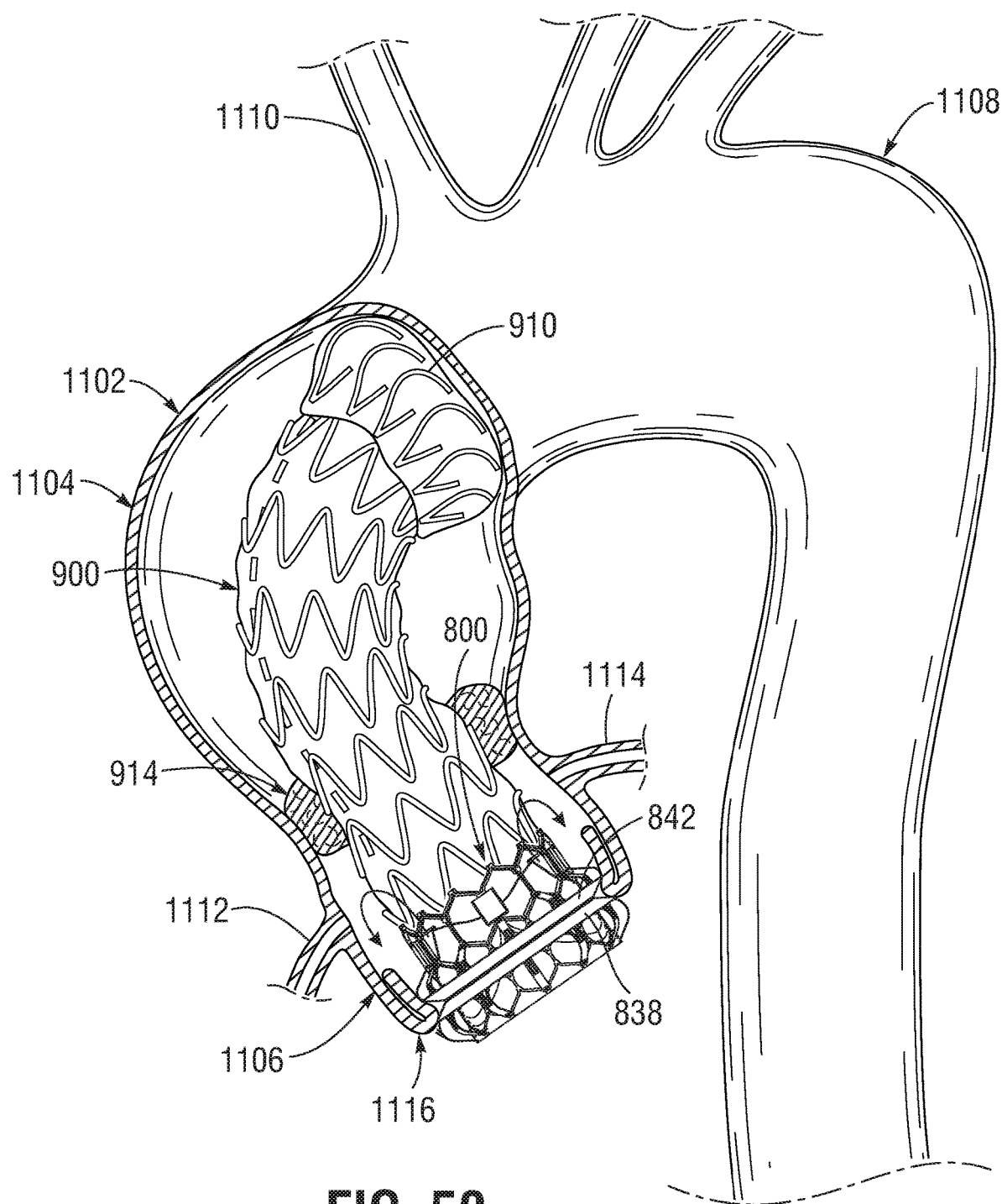
FIG. 50 is a partial cross-sectional view of an aorta illustrating the prosthetic implant of FIG. 48 implanted in the native aortic valve.

FIG. 50 illustrates the prosthetic valve 800 and the conduit 900 coupled together and implanted within the ascending aorta 1102 to isolate and bypass an aneurysm 1104 of the ascending aorta. In the illustrated configuration, the struts 802 and 804 (FIG. 43) can bow, curve, or extend radially outwardly from the frame 16 to anchor the prosthetic valve 800 in the aortic root 1106. In certain embodiments, the prosthetic valve 800 can be disposed in the aortic annulus 1116 such that the aortic annulus is positioned between the skirts 838 and 842. In certain embodiments, the prosthetic valve 800 can press the native leaflets toward or against the walls of the aortic root 1106, such as the walls of the Valsava sinuses. Meanwhile, the frame 910 of the conduit 900 can anchor the outflow end 906 of the conduit in the aortic arch 1108 at a location, for example, proximate the brachiocephalic artery 1110. The sealing feature 914 can form a seal between the main body 902 of the conduit 900 and the walls of the aorta to isolate the aneurysm 1104. The stent frame 910 at the proximal end of the conduit 900 can also form a seal with the aortic wall to isolate the aneurysm 1104. In certain embodiments, the outflow end portion 906 can include a sealing feature similar to the sealing feature 914.

In certain embodiments, a portion of the blood flowing through the prosthetic valve 800 can flow through the conduit 900 to the aortic arch, and a portion of the blood can flow into the aortic root 1106 (e.g., through openings between the frame struts of the prosthetic valve or openings along the first end portion 904 of the conduit) to perfuse the coronary arteries 1112 and 1114. In other embodiments, the conduit 900 and/or the prosthetic valve 800 can include conduits or stents (not shown) that extend at least partially into the coronary arteries 1112 and 1114, and/or that are anastomosed to the coronary arteries. In yet other embodiments, the sealing feature 914 can be configured as a stent frame similar to the frame 910, and/or the frame 910 can be configured as a voluminous fabric and/or as a skirt.

Figure 51:
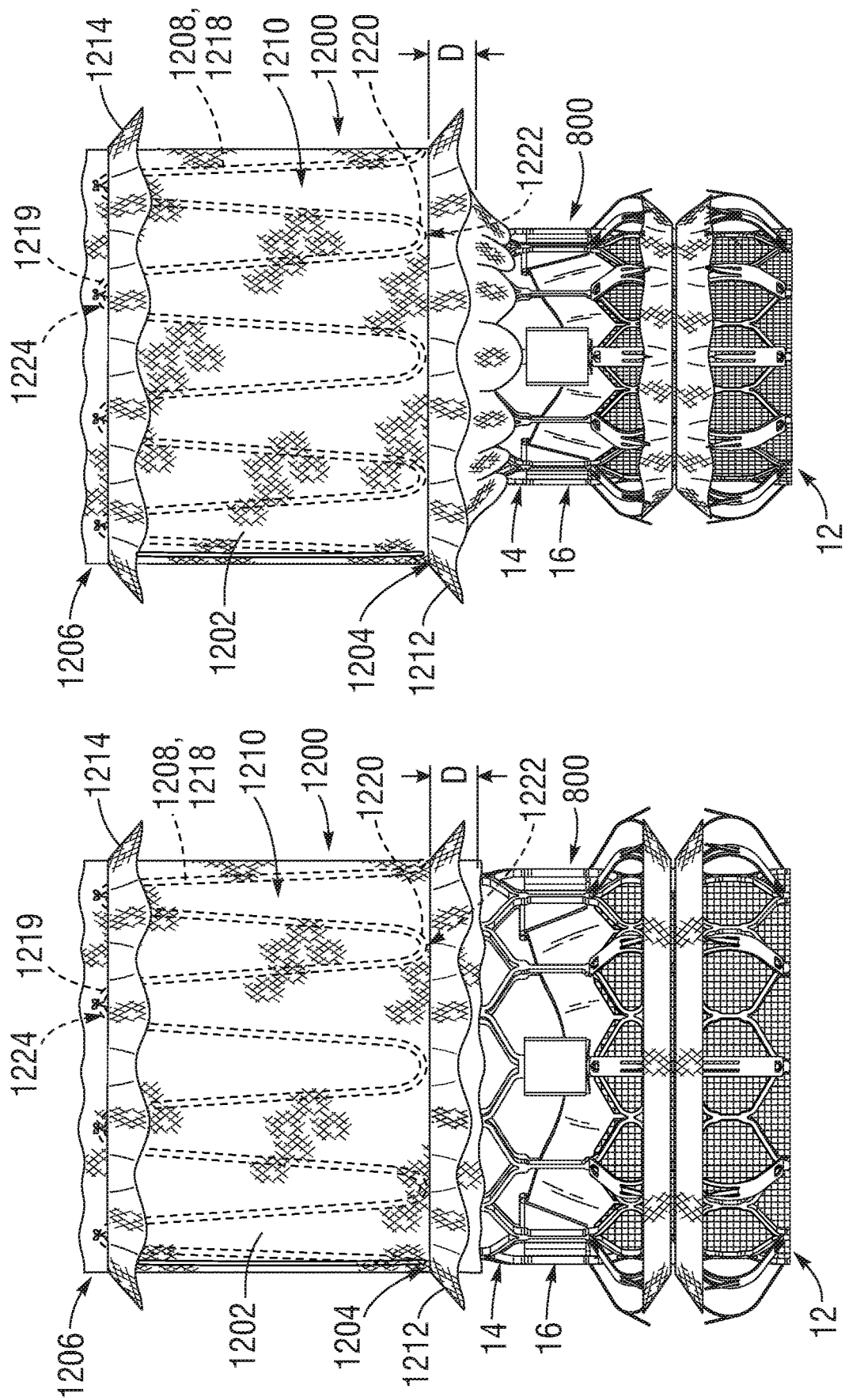
FIGS. 51A and 51B are side elevation views of a prosthetic device including a prosthetic valve of FIG. 41 coupled to a conduit, according to another embodiment.

FIGS. 51A and 51B illustrate another embodiment of a prosthetic device comprising a prosthetic valve 800 coupled to a conduit 1200, which can be configured for implantation within the native aortic valve and the ascending aorta. The conduit 1200 can comprise a tubular main body 1202 having a first (e.g., inflow) end portion 1204 and a second (e.g., outflow) end portion 1206. The main body 1202 can comprise a stent frame 1208 including one or more strut members 1218 curved so as to comprise a plurality of axially spaced-apart peaks 1219 and valleys 1220 in the manner of a sine wave. The valleys 1220 can be located at an inflow end 1222 of the frame 1208, and the peaks 1218 can be located at an outflow end 1224 of the frame. In certain embodiments, the stent frame 1208 and, thus, the main body 1202, can be movable between a collapsed delivery configuration and an expanded, functional configuration, similar to the prosthetic valve 800. The stent frame 1208 can comprise any of the self-expanding or plastically-expandable materials described herein.

The conduit 1200 can further include one or more textile coverings 1210 disposed around the frame 1208 (e.g., on the inside and/or the outside of the frame). The conduit 1200 illustrated in FIGS. 51A and 51B is shorter than the conduit 900 of FIG. 48, but can have any suitable length and/or curvature depending upon the particular body lumen and/or species into which the device is intended for implantation. For example, multiple conduits 1200 can be coupled to each other serially such that they define a common lumen in order to provide an implant with a specified length.

The conduit 1200 can include a first sealing feature or sealing member configured as a skirt 1212 disposed circumferentially around the inflow portion 1204. The conduit can further include a second sealing feature or sealing member configured as a skirt 1214 disposed circumferentially around the outflow end portion 1206. When implanted in the aorta, the skirts 1212 and 1214 can be configured to form a seal with the walls of the aorta to isolate and bypass a portion of the aorta, such as an aneurysm similar to the aneurysm shown in FIG. 50. In some embodiments, the skirts 1212 and 1214 may be integrally formed with the covering 1210, or may be separately formed and secured to the covering 1210 (e.g., by stitching or suturing). For example, in the illustrated embodiment the skirts 1212 and 1214 are sutured to the covering 1210 along one circumferential edge, and are free at the other circumferential edge so that the skirts can extend radially outwardly from the conduit 1200 to engage and form a seal with the walls of the aorta. In certain embodiments, the covering 1210 and the skirts 1212, 1214 can comprise a woven fabric, such as a woven PET fabric.

The conduit 1200 can be coupled to the prosthetic valve 800 by any of various coupling means including sutures, extensions looped through the frame struts of the prosthetic valve 800, etc. In certain embodiments, the conduit 1200 can be flexibly coupled to the prosthetic valve 800. For example, in the illustrated embodiment, the inflow end 1222 of the frame 1208 can be axially spaced apart in the downstream direction from the outflow end 14 of the frame 16 of the prosthetic valve 800 such that the two frames are separated by a distance D. The covering 1210 can extend across the distance D between the frame 1208 and the frame 16. This can allow the frames 16 and 1208 to be crimped and/or expanded independently of each other, as illustrated in FIG. 51B.

Figure 52:
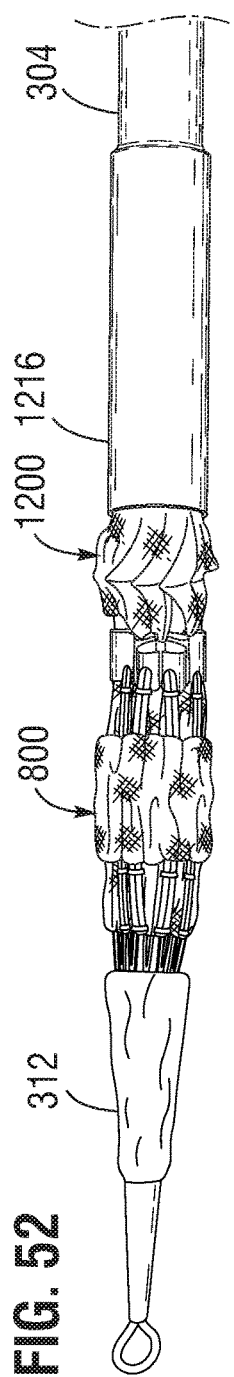
FIG. 52 is a perspective view illustrating the prosthetic device of FIGS. 51A and 51B crimped on a balloon catheter of a delivery apparatus.

In certain embodiments, the configuration of the frame 1208 illustrated in FIGS. 51A and 51B can be particularly suited for manufacture from Nitinol or another self-expanding material, although plastically-expandable materials may also be used. FIG. 52 illustrates the prosthetic device 800 and the conduit 1200 crimped on the balloon 312 at the distal end of the balloon catheter 304 of the delivery apparatus of FIG. 24. In embodiments in which the conduit 1200 is made from a self-expandable material, the conduit 1200 can be encapsulated in a polymeric covering or capsule 1216 that retains the conduit 1200 in the collapsed delivery configuration. When the device is deployed, the capsule 1216 can be opened, withdrawn, or removed from over the conduit 1200, allowing the conduit 1200 to expand to its functional size.

Figure 53:
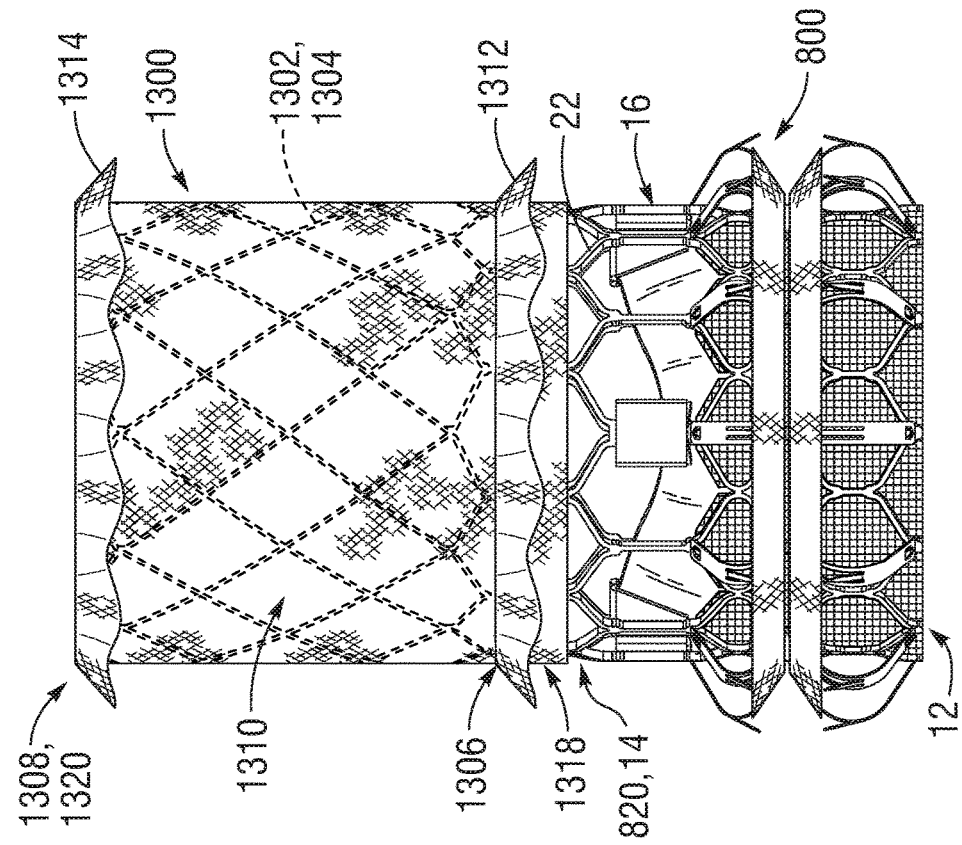
FIG. 53 is a side elevation view of another embodiment of a prosthetic device including the prosthetic valve of FIG. 41 coupled to a conduit.

FIG. 53 illustrates another embodiment of a prosthetic device including a conduit 1300 coupled to a prosthetic valve 800. The conduit 1300 can comprise a tubular main body having a first (e.g., inflow) end portion 1318 in fluid communication with the outflow end 820 of the prosthetic valve 800, and a second (e.g., outflow) end portion 1320 opposite the inflow end portion 1318. The conduit 1300 can include a frame 1302 comprising a plurality of angled, interconnected strut members 1304, and having an inflow end 1306 and an outflow end 1308. In the illustrated example, the inflow end 1306 of the frame 1302 can be axially spaced apart from the outflow end 14 of the frame 16 of the prosthetic valve 800 in a downstream direction, similar to the conduit 1200 above.

A covering 1310 can extend around the outside of the frame 1302, and between the inflow end 1306 of the frame 1302 and the outflow end 14 of the frame 16. In certain embodiments, the covering 1310 can be sutured to the strut members 22 of the frame 16 of the prosthetic valve 800 to couple the conduit 1300 and the prosthetic valve 800 together. In other embodiments, the covering 1310 can comprise loops (e.g., fabric or suture loops) or other securing means to couple the conduit 1300 to the frame 16. Sealing features configured as skirts 1312 and 1314 can extend circumferentially around the conduit 1300. The skirt 1312 can be located at the inflow end 1318 of the conduit 1300 (e.g., adjacent the inflow end 1306 of the frame 1302), and the skirt 1314 can be located at the outflow end 1308 of the frame 1302. In the illustrated configuration, the skirts 1312 and 1314 are sutured to the covering 1310 along one circumferential edge, and are free at the other circumferential edge so that the skirts can extend radially outwardly from the conduit 1300 to engage and form a seal with the walls of the aorta.

The configuration of the frame 1302 illustrated in FIG. 53 can be particularly suited for manufacture from plastically-expandable materials such as cobalt-chromium or stainless steel, although self-expanding materials may also be used. In embodiments where the frame 1302 is made from a plastically-expandable material, the conduit 1300 can be expanded to its functional size by a balloon or another expansion device. For example, in certain configurations, the prosthetic valve 800 and the conduit 1300 can be crimped over the balloon 312 of the balloon catheter 304 of FIG. 24, and the balloon 312 may be used to expand both the prosthetic valve 800 and the conduit 1300. In embodiments where the frame 1302 comprises a plastically-expandable material, the prosthetic valve 800 and the conduit 1300 can be enclosed in a loader or container similar to the loader 310 of FIG. 26 for insertion into the body through an introducer sheath.

Figure 54:
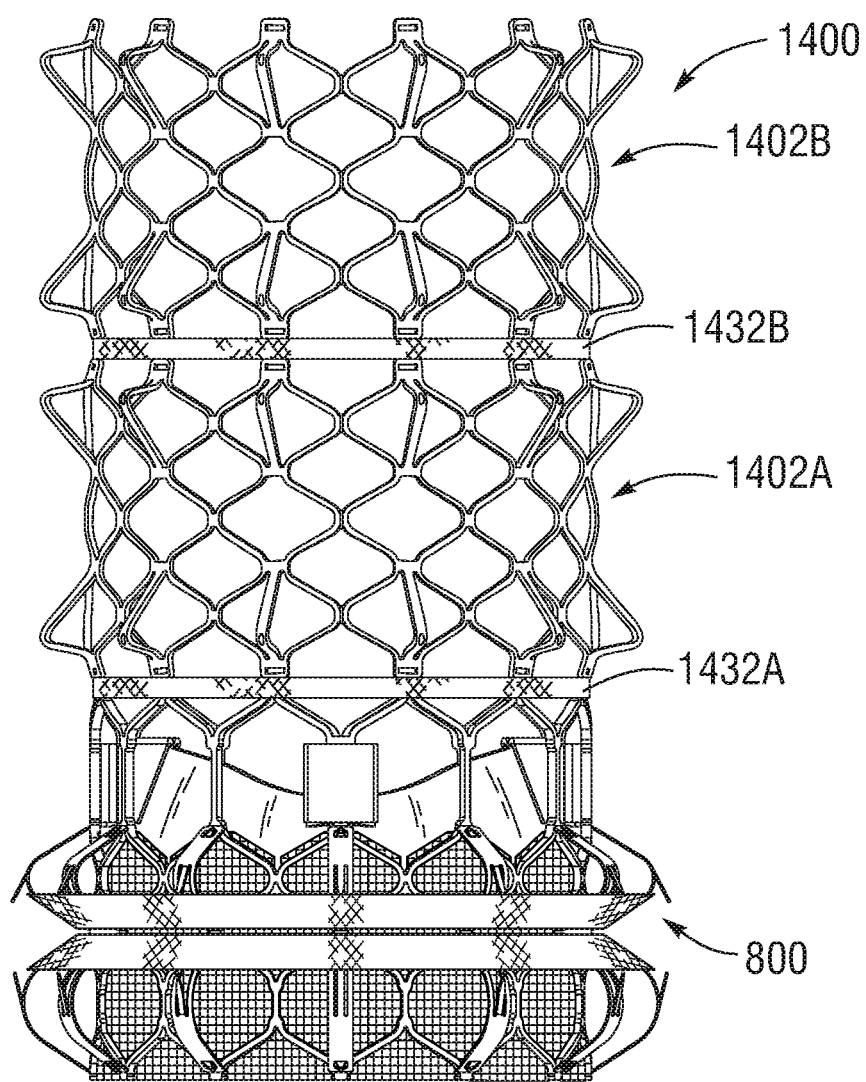
FIG. 54 is a side elevation view of another embodiment of a prosthetic implant including the prosthetic valve of FIG. 41 coupled to a conduit including a plurality of expandable frames.

FIG. 54 illustrates another embodiment of a prosthetic device including a prosthetic heart valve configured as the prosthetic heart valve 800, and a radially expandable and collapsible conduit 1400 comprising a plurality of frames 1402 arranged coaxially with each other, and with the prosthetic valve 800. In the illustrated embodiment, the conduit 1400 comprises two frames 1402A and 1402B. However, the conduit 1400 can comprise any number of frames 1402, such as a single frame, or more than two frames, depending upon the particular length desired.

FIG. 55 illustrates a representative frame 1402 in greater detail. The frame 1402 can have a cylindrical shape, and can comprise a plurality of interconnected, angled strut members 1404. The frame 1402 can have an inflow end 1406 and an outflow end 1408. The struts 1404 can define a plurality of apices 1410 at the inflow end 1406 where respective strut members are joined, and can define a plurality of apices 1412 at the outflow end 1408 where respective struts are joined. The frame 1402 can further comprise a plurality of strut members 1414 arrayed circumferentially around the inflow end 1406 of the frame, and a plurality of strut members 1416 arrayed circumferentially around the outflow end 1408 of the frame. In the illustrated embodiment, the longitudinal axes 1418 of the strut members 1414 and 1416 are oriented parallel to the longitudinal axis 1420 of the frame 1402. The struts 1414 can be coupled to the apices 1410 at one end, can extend axially along the frame 1402 across one or more frame openings 1426 defined by the struts 1404, and can be coupled to strut junctions 1422 at the other end. The struts 1416 can be coupled to the apices 1412 at one end, can extend axially along the frame 1402 across one or more frame openings 1426, and can be coupled to strut junctions 1424 at the opposite end. In certain embodiments, the struts 1414 and 1416 can be integrally formed with the frame 1402 (e.g., by laser cutting the frame 1402 from a tube), or can be separately formed and secured to the frame 1402.

FIG. 56A illustrates the frame 1402 in the collapsed configuration. The struts 1414 and 1416 can have lengths configured such that when the frame 1402 is in the collapsed configuration, the struts 1414 and 1416 are straight, or substantially straight, and can lie in close proximity to the struts 1404. When expanded, the frame 1402 can shorten, which can cause the struts 1414 and 1416 to bow, arch, or curve radially outwardly from the frame 1402, as illustrated in FIGS. 56B and 56C.

In other embodiments, the struts 1414, the struts 1416, or combinations thereof can be oriented at an angle to the longitudinal axis 1420 of the frame. For example, one or both sets of struts 1414 and/or 1416 can be oriented such that the struts extend circumferentially around the frame 1402 (e.g., at a 90° angle to the longitudinal axis 1420). In certain embodiments, the orientation of the struts 1414 and/or the orientation struts 1416 can vary or alternate on a strut-by-strut basis around the circumference of the frame. For example, a strut 1414 can be oriented longitudinally, followed by a strut 1414 oriented circumferentially, followed by a strut 1414 oriented longitudinally, etc. Any of the struts 1414 and/or 1416 can also extend across the openings 1426 diagonally, or at any angle. The frame 1402 may also include more or fewer struts 1414 and/or 1416 than shown. The frame 1402 can also include additional rows of struts configured to bow or curve radially outwardly as the frame foreshortens during expansion. For example, each row of frame openings 1426 can comprise corresponding struts configured to curve radially outwardly in the expanded configuration. Any of the frame configurations described herein can also comprise struts oriented at different angles and configured to bend, bow, or expand radially outwardly from the frame.

Returning to FIG. 55, the frame 1402 can include an exterior covering schematically illustrated at 1428. The covering 1428 can extend over the struts 1414 and 1416. When the frame 1402 is expanded, the struts 1414, 1416, and the covering 1428, can contact the walls of the aorta to form a seal, and can aid in holding the conduit in place. In certain embodiments, the covering 1428 can comprise a woven or non-woven fabric, a polymeric coating applied by electrospinning or dip-coating, or any other suitable material. Where a conduit 1400 includes multiple frame units 1402, the covering 1428 can be sized to cover all of the frames 1402, or each frame can comprise a separate covering, depending upon the particular characteristics desired.

The frame 1402 can also include a tubular inner covering schematically illustrated at 1430. The covering 1430 can be configured to promote laminar blood flow through the frame 1402, and can comprise a woven or non-woven fabric, an electrospun or dip-coated polymeric layer, etc. Where a conduit 1400 includes multiple frame units 1402, the covering 1430 can be sized to extend between all of the frames 1402, or each frame can comprise a separate covering.

Returning to FIG. 54, the prosthetic valve 800 and the first frame 1402A can be coupled or interconnected by a flexible coupling means, such as a fabric or flexible polymer layer generally indicated at 1432A. The frames 1402A and 1402B can be coupled together by a similar coupling 1432B. In certain embodiments, the couplings 1432A and 1432B can be portions of the exterior covering 1428 and/or the interior covering 1430 that extend between the frames 1402A and 1402B, and/or between the frame 1402A and the prosthetic valve 800. In other embodiments, the coupling 1432A and/or the coupling 1432B can be a separate piece of material.

The flexible couplings 1432A and 1432B can allow the prosthetic valve 800, the frame 1402A, and the frame 1402B to be expanded and/or collapsed independently of one another, similar to the embodiment of FIGS. 51A, 51B, and 53 above. For example, FIGS. 57A-57E illustrate implantation of a prosthetic device similar to the device of FIG. 54 in a porcine aorta 1434 during a porcine animal trial. The prosthetic device of FIGS. 57A-57E includes a prosthetic valve 800 and a conduit 1400 including a single frame 1402 sized for implantation in a porcine aorta. In other embodiments, including embodiments for use in human patients, the conduit may include more than one frame.

Figure 57A:
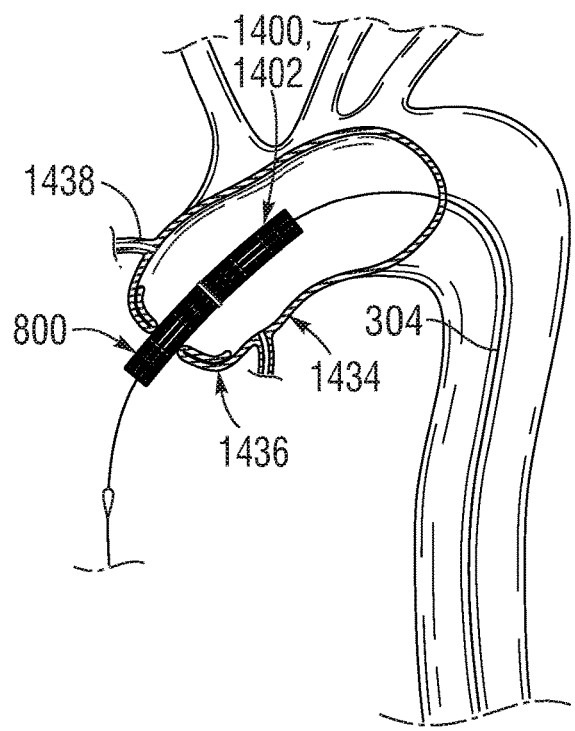
FIGS. 57A-57E illustrate deployment of a prosthetic device including the prosthetic heart valve of FIG. 41 and a conduit, the conduit including an independently expandable frame, in a porcine aorta.
Figure 57B:
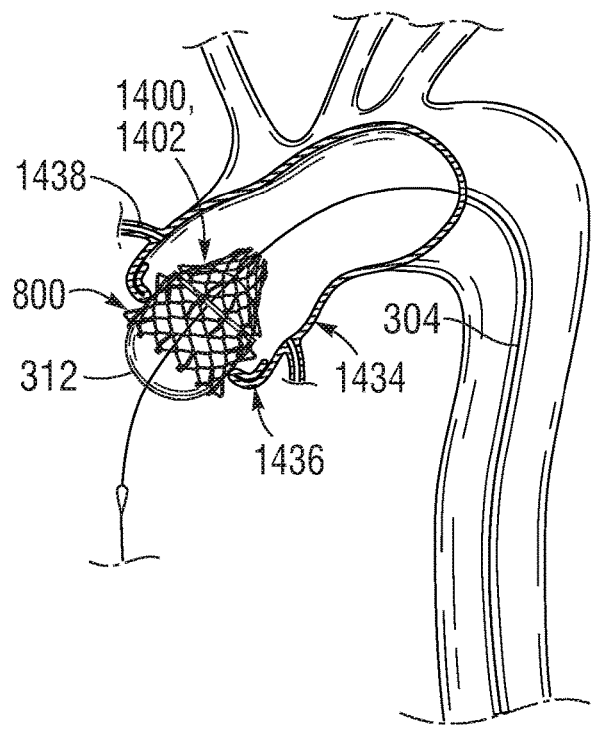
Figure 57C:
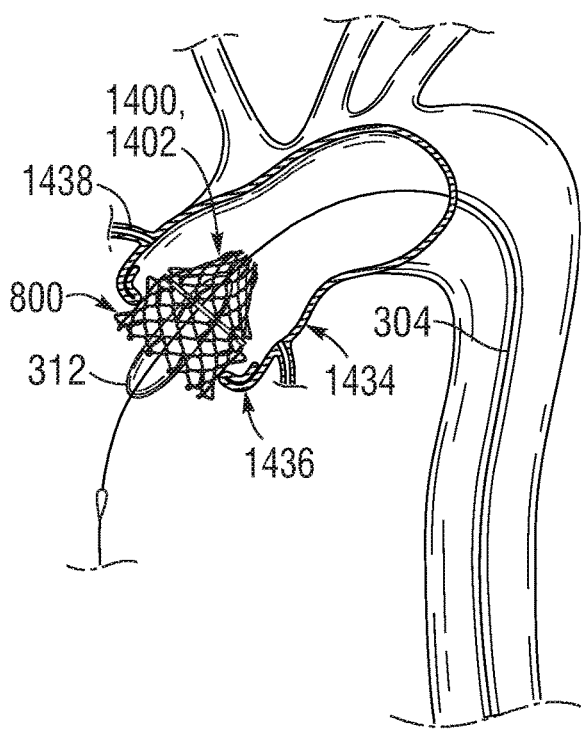
Figure 57D:
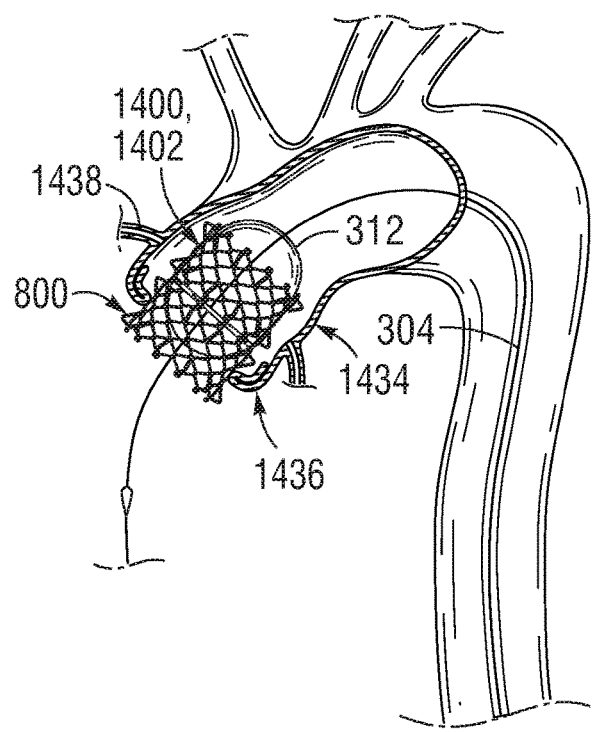
Figure 57E:
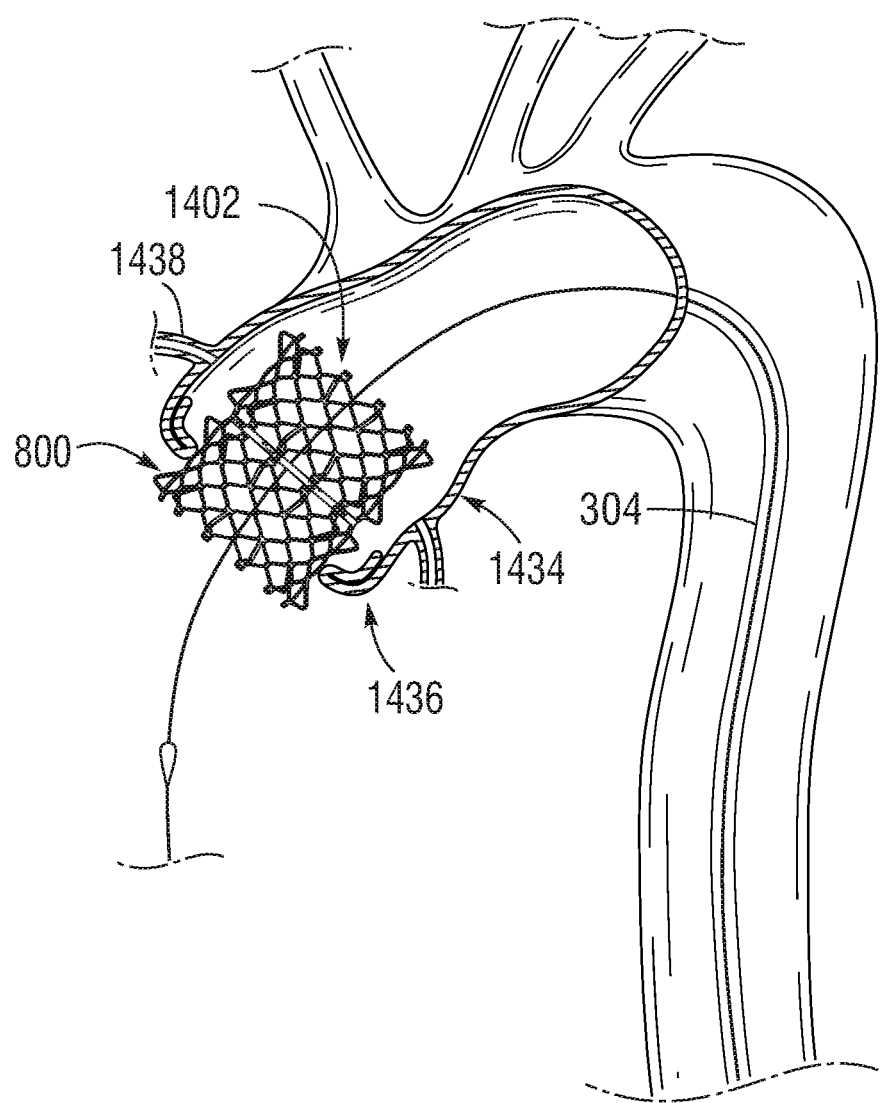

In FIG. 57A, the prosthetic valve 800 and the frame 1402 are shown collapsed on a balloon catheter 304, with the prosthetic valve 800 located in the aortic annulus generally indicated at 1436, and the frame 1402 located in the ascending aorta. FIG. 57B illustrates expansion of the prosthetic valve 800 with a balloon 312. As the prosthetic valve 800 expands, the struts 802 and 804 (FIG. 41) can curve radially outwardly from the frame 16 to anchor the prosthetic valve against the surrounding tissue. In the illustrated embodiment, inflation of the balloon 312 to expand the prosthetic valve 800 can also cause partial expansion of the inflow end portion of the frame 1402. FIG. 57C illustrates deflation of the balloon 312, and proximal retraction of the balloon catheter 304 to position the balloon 312 within the frame 1402. FIG. 57D illustrates inflation of the balloon 312 a second time to expand the frame 1402 in the ascending aorta. Expansion of the frame 1402 can cause corresponding motion of the struts 1414 and 1416 into the curved shape. FIG. 57E illustrates the prosthetic valve 800 and the conduit 1400 fully deployed. When fully deployed, the prosthetic valve 800 can regulate blood flow into the aorta from the left ventricle. Referring to FIG. 57E, a portion of the blood flow through the prosthetic valve 800 can flow through openings in the frame of the prosthetic valve to perfuse the coronary arteries 1438, and a portion of the blood flow can flow through the conduit 1400 to bypass at least a portion of the ascending aorta. For conduits including more than one frame, the balloon 312 can be deflated, proximally or distally repositioned, and re-inflated to expand the frames of the prosthetic valve and/or of the conduit in any order.

In certain embodiments, the strut members configured to curve radially outwardly from the frame of any of the frame embodiments described herein can comprise mechanisms or means for inducing bending at select locations or regions along the lengths of the struts. For example, in certain embodiments the struts may comprise living hinges about which the struts can bend as the frame foreshortens. In certain embodiments, the struts can comprise areas of reduced thickness to induce bending at that location. In other embodiments the struts can comprise any of a variety of joints, hinges, or pivotable connections about which the struts can bend into the curved shape. Although the prosthetic heart valve frame embodiments described herein are presented in the context of plastically-expandable valves, it should be understood that the disclosed frame embodiments can also be implemented with various other types of prosthetic heart valves such as self-expandable valves and mechanically-expandable valves. Examples of self-expandable prosthetic heart valves can be found in U.S. Pat. Nos. 8,652,202, 9,155,619, and 9,867,700, which are incorporated herein by reference. Examples of mechanically-expandable prosthetic heart valves can be found in U.S. Publication No. 2018/0153689 and U.S. Publication No. 2019/0105153, which are incorporated herein by reference. Additional examples of plastically-expandable prosthetic heart valves can be found in U.S. Pat. No. 9,393,110, and U.S. Publication No. 2018/0028310, which are incorporated herein by reference. The frame embodiments described herein can also be used in valves intended for implantation at any of the native annuluses of the heart (e.g., the aortic, pulmonary, mitral, and tricuspid annuluses), and can be configured for implantation within existing prosthetics valves (so called "valve-in-valve" procedures). The frame embodiments can also be used in combination with other types of devices implantable within other body lumens outside of the heart, or heart valves that are implantable within the heart at locations other than the native valves, such as trans-atrial or trans-ventricle septum valves, stent grafts, etc.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the prosthetic valve illustrated in FIG. 3 is shown in the orientation associated with implantation in the mitral valve, and so the upper end of the valve is its inflow end and the lower end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims.

The invention claimed is:

1. A prosthetic heart valve that is radially collapsible to a collapsed configuration and radially expandable to an expanded configuration, comprising:
   an annular inner frame comprising a plurality of angled first strut members, the inner frame being configured to foreshorten from a first length corresponding to the collapsed configuration to a second length corresponding to the expanded configuration when the prosthetic heart valve is expanded to the expanded configuration;
   a leaflet structure situated at least partially within the inner frame; and
   an outer frame disposed radially outward of the inner frame and coupled to the inner frame, the outer frame being configured to collapse with the inner frame to the collapsed configuration and expand with the inner frame to the expanded configuration, the outer frame comprising a plurality of second strut members;
   wherein at least respective portions of the second strut members are configured to bend radially outwardly into a curved shape as the inner frame and the outer frame move from the collapsed configuration to the expanded configuration; and
   wherein the prosthetic heart valve further comprises a skirt member disposed between the second strut members and the inner frame and secured to the second strut members.

2. The prosthetic heart valve of claim 1, wherein:
   the second strut members comprise first and second end portions; and
   the first and second end portions of the second strut members are coupled to the outer inner frame such that the first and second end portions move toward each other as the outer frame expands to bend the second strut members into the curved shape.

3. The prosthetic heart valve of claim 1, wherein:
   the inner frame comprises an inflow end and an outflow end; and
   the second strut members extend from the inflow end of the inner frame to the outflow end.

4. The prosthetic heart valve of claim 1, wherein the outer frame further comprises circumferentially-extending strut members that interconnect the second strut members.

5. The prosthetic heart valve of claim 1, wherein:
   the inner frame comprises an inflow end and an outflow end; and
   the second strut members are situated around the inner frame, and each of the second strut members branches into two third strut members adjacent the inflow end of the inner frame.

6. The prosthetic heart valve of claim 5, wherein the third strut members extending from a given second strut member curve radially away from the inner frame and are coupled to third strut members of adjacent second strut members.

7. The prosthetic heart valve of claim 6, wherein when the prosthetic heart valve is in the expanded configuration, the second strut members form a first portion of the outer frame having a convex exterior surface, and the third strut members form a second portion of the outer frame comprising an annular flange.

8. The prosthetic heart valve of claim 7, wherein the second strut members comprise apices spaced radially away from the inner frame when the prosthetic heart valve is in the expanded configuration.

9. The prosthetic heart valve of claim 6, further comprising a skirt member secured to the third strut members.

10. The prosthetic heart valve of claim 1, wherein the second strut members comprise tissue-engaging members configured to extend radially outwardly from the second strut members when the second strut members are in the curved shape.

11. A method, comprising:
    introducing the prosthetic heart valve of claim 1 into a patient's vasculature in the radially collapsed configuration;
    advancing the prosthetic heart valve to a treatment site; and
    radially expanding the prosthetic heart valve such that the inner frame foreshortens and the second strut members of the outer frame bend into the curved shape.

12. A prosthetic heart valve that is radially collapsible to a collapsed configuration and radially expandable to an expanded configuration, comprising:
    an annular frame comprising a plurality of angled first strut members, the frame being configured to foreshorten from a first length corresponding to the collapsed configuration to a second length corresponding to the expanded configuration when the prosthetic heart valve is expanded to the expanded configuration;
    a leaflet structure situated at least partially within the frame; and
    a plurality of second strut members extending longitudinally along at least a portion of the frame and coupled to the frame;
    wherein the second strut members are configured to bend radially outwardly as the frame moves from the collapsed configuration to the expanded configuration such that at least one of the second strut members forms a first apex and a second apex spaced radially outwardly from the frame when the prosthetic heart valve is in the expanded configuration, and wherein the second apex is spaced radially outwardly from the frame by a greater distance than the first apex.

13. The prosthetic heart valve of claim 12, wherein at least a portion of the plurality of second strut members comprise tissue-engaging members configured to extend away from the second strut members when the prosthetic heart valve is in the expanded configuration.

14. The prosthetic heart valve of claim 13, wherein the tissue-engaging members extend from apices of the second strut members.

15. A prosthetic heart valve that is radially collapsible to a collapsed configuration and radially expandable to an expanded configuration, comprising:
    an annular frame comprising a plurality of angled first strut members, the frame being configured to foreshorten from a first length corresponding to the collapsed configuration to a second length corresponding to the expanded configuration when the prosthetic heart valve is expanded to the expanded configuration;

a leaflet structure situated at least partially within the frame;

a plurality of second strut members extending longitudinally along at least a portion of the frame and coupled to the frame, the second strut members being arranged circumferentially around the frame in a first row and configured to bend radially outwardly from the frame into a curved shape as the frame moves from the collapsed configuration to the expanded configuration; and a plurality of third strut members extending longitudinally along at least a portion of the frame and coupled to the frame, the third strut members being arranged circumferentially around the frame in a second row and configured to bend radially outwardly from the frame into a curved shape as the frame moves from the collapsed configuration to the expanded configuration;

wherein the second strut members of the first row are circumferentially offset from the third strut members of the second row.

16. The prosthetic heart valve of claim 15, wherein the second strut members at least partially overlap with the third strut members in an axial direction when the prosthetic heart valve is in the expanded configuration.

17. The prosthetic heart valve of claim 15, wherein the third strut members comprise reduced width portions configured to induce bending of the third strut members at the reduced width portions.

18. The prosthetic heart valve of claim 15, wherein at least a portion of the plurality of second strut members comprise tissue-engaging members configured to extend away from the second strut members when the prosthetic heart valve is in the expanded configuration.

19. The prosthetic heart valve of claim 1, wherein:

the inner frame comprises an inflow end and an outflow end; and the second strut members of the outer frame comprise apices when the inner frame is in the expanded configuration, and the apices define a shoulder of the outer frame that is closer to the inflow end of the inner frame than to the outflow end of the inner frame.

20. The prosthetic heart valve of claim 1, wherein the second strut members of the outer frame are sutured to the inner frame.

* * * * *